US010441617B2

(12) United States Patent
Lewis et al.

(10) Patent No.: US 10,441,617 B2
(45) Date of Patent: *Oct. 15, 2019

(54) BREEDING, PRODUCTION, PROCESSING AND USE OF MEDICAL CANNABIS

(71) Applicant: BIOTECH INSTITUTE, LLC, Westlake Village, CA (US)

(72) Inventors: Mark Anthony Lewis, Westlake Village, CA (US); Michael Dane Backes, Westlake Village, CA (US)

(73) Assignee: Biotech Institute, LLC, Westlake Village, CA (US)

( * ) Notice: Subject to any disclaimer, the term of this patent is extended or adjusted under 35 U.S.C. 154(b) by 370 days.

This patent is subject to a terminal disclaimer.

(21) Appl. No.: 14/216,650

(22) Filed: Mar. 17, 2014

(65) Prior Publication Data

US 2014/0298511 A1 Oct. 2, 2014

Related U.S. Application Data

(60) Provisional application No. 61/801,528, filed on Mar. 15, 2013.

(51) Int. Cl.
*A01H 5/02* (2018.01)
*A01H 5/10* (2018.01)
*A61K 36/185* (2006.01)

(52) U.S. Cl.
CPC ............ *A61K 36/185* (2013.01); *A01H 5/02* (2013.01); *A01H 5/10* (2013.01)

(58) Field of Classification Search
CPC .............. A01H 5/12; A01H 5/02; A01H 5/10
See application file for complete search history.

(56) References Cited

U.S. PATENT DOCUMENTS

| | | | |
|---|---|---|---|
| 4,279,824 A | 7/1981 | McKinney | |
| 6,403,126 B1 | 6/2002 | Webster et al. | |
| 6,630,507 B1 | 10/2003 | Hampson et al. | |
| 7,968,594 B2 | 6/2011 | Guy et al. | |
| 9,095,554 B2 * | 8/2015 | Lewis | A01H 1/04 |
| 9,370,164 B2 | 6/2016 | Lewis et al. | |
| 9,642,317 B2 | 5/2017 | Lewis et al. | |
| 2004/0049059 A1 | 3/2004 | Mueller | |
| 2008/0103193 A1 | 5/2008 | Castor et al. | |
| 2008/0241339 A1 | 10/2008 | Mitchell et al. | |
| 2009/0035396 A1 | 2/2009 | De Meijer | |
| 2010/0216872 A1 | 8/2010 | Letzel et al. | |
| 2011/0098348 A1 | 4/2011 | De Meijer | |
| 2012/0311744 A1 | 12/2012 | Sirkowski | |
| 2013/0109747 A1 | 5/2013 | Whittle | |
| 2014/0243405 A1 | 8/2014 | Whalley | |
| 2014/0245494 A1 | 8/2014 | Cohen | |
| 2014/0245495 A1 | 8/2014 | Cohen | |
| 2014/0287068 A1 | 9/2014 | Lewis et al. | |
| 2015/0359188 A1 * | 12/2015 | Lewis | A01H 1/04 |
| | | | 800/266 |
| 2015/0366154 A1 | 12/2015 | Lewis et al. | |
| 2016/0324091 A1 | 11/2016 | Lewis et al. | |
| 2017/0202170 A1 | 7/2017 | Lewis et al. | |
| 2018/0064055 A1 | 3/2018 | Lewis et al. | |
| 2018/0284145 A1 | 10/2018 | Giese et al. | |

FOREIGN PATENT DOCUMENTS

| | | |
|---|---|---|
| GB | 2459125 | 10/2009 |
| WO | WO 2011/110866 A1 | 9/2011 |
| WO | WO 2015/065544 A1 | 5/2014 |
| WO | WO 2014/145490 A2 | 9/2014 |
| WO | WO 2016/105514 A1 | 6/2016 |
| WO | WO 2016/123160 A1 | 8/2016 |

OTHER PUBLICATIONS

ElSohly, M.A., et al., Journal of Forensic Sciences, 1984; vol. 29, No. 2, pp. 500-514.*
Fishedick, J.T. et al., Pytochemistry 2010; vol. 71, pp. 2058.2073.*
De Meijer et al., 2003, The Inheritance of Chemical Phenotype in *Cannabis sativa* L. Genetics, 163:335-346.
De Meijer et al., 2005, The Inheritance of Chemical Phenotype in *Cannabis sativa* L. (II) Cannabigerol Predominant Plants. Euphytica, 145:189-198.
De Meijer et al., 2009, The Inheritance of chemical phenotype in *Cannabis sativa* L. (III) Variation in Cannabichromene Proportion Euphytica, 165:293-311.
De Meijer et al., 2009, The Inheritance of Chemical Phenotype in *Cannabis sativa* L. (IV) Cannabinoid-Free Plants, Euphytica, 168:95-112.
2011, Taming THC: potential cannabis synergy and phytocannabinoid-terpenoid entourage effects, British Journal of Pharmacology, 163:1344-1364.
Russo et al. (2006, A tale of two cannabinoids: the therapeutic rationale for combining tetrahydrocannabinol and cannabidiol, Medical Hypothesis, 2006, 66:234-246).
Hazekamp and Fischedick 2010. "Metabolic fingerprinting of *Cannabis sativa* L., cannabinoids and terpenoids for chemotaxonomic and drug standardization purposes" Phytochemistry 2058-73.
McPartland and Russo 2001 Cannabis and Cannabis Extracts: Greater Than the Sum of Their Parts? Journal of Cannabis Therapeutics vol. 1, No. 3/4,2001, pp. 103-132.
RG Pertwee. 2008 "The diverse CB1 and CB2 receptor pharmacology of three plant cannabinoids: delta 9 tetrahydrocannabinol, cannabidiol and delta 9 tetrahydrocannabivarin" Br. J Pharmacol. 153(2):199-215.
CBD Crew "About Us" Printed copy provided as published on Apr. 10, 2012. URL: http://cbdcrew.org/about-us/.
CBD Crew "Varieties" Printed copy provided as published on Mar. 20, 2012. URL: http://cbdcrew.org/varieties/.
International PCT Search Report for PCT/US2014/046694, dated Jan. 5, 2015.

(Continued)

*Primary Examiner* — Russell Kallis
(74) *Attorney, Agent, or Firm* — Cooley LLP

(57) ABSTRACT

The invention provides compositions and methods for the breeding, production, processing and use of medical *cannabis*.

10 Claims, 6 Drawing Sheets

(56) References Cited

OTHER PUBLICATIONS

International PCT Search Report for PCT/US14/30267, dated Nov. 7, 2014.
Seedsman Listing of "Sweet and Sour Widow", on May 21, 2013, http://web.archive.org/web/20130521045347/http://www.seedsman.com/en/cbd-sweet-n-sour-widow-regular-5-seeds.
Analytical 360 analysis of Sweet & Sour Widow CBD on Nov. 2, 2013. http://analytical360.com/m/expired/131803.
Harm Van Bakel et al., "The draft genome and transcriptome of *Cannabis sativa*", Genome Biology, Oct. 20, 2011.
Agilent Technologies, Inc. "Consideration for Selecting GC/MS or LC/MS for Metabiomics", Feb. 24, 2007.
Waksmundzka-Hajnos and Monika, "High Performance Liquid Chromatography in Phytochemical Analysis (Chromatograhic Science Series)." Published May 14, 2012. p. 582 provided.
The Werc Shop Terpene Profiling Services, Aug. 26, 2012. http://web.archive.org/web/20120826071723/http://thewercshop.com/services/terpene-profiling-services.
G. of Vancouver Island Seed Company, "How to make Clones", Cannabis Culture Magazine published on Tuesday, Apr. 29, 2009. Available online at http://www.cannabisculture.com/content/how-make-clones.
Fishedick, J. et al., "Metabolic fingerprinting of *Cannabis sativa* L., cannabinoids and terpenoids for chemotaxonomic and drug standardization purposes" Phytochemistry 2010, vol. 71., pp. 2058-2073.
Russo, E.B., "Taming THC: potential cannabis synergy and phytocannabinoid-terpenoid entourage effects" The British Journal of Pharmacology, 2011, pp. 1344-1364, vol. 613.
CBD Crew Web Pub; (Critical Mass sample available from Northwest Canna Connection; Feb. 26, 2014, pp. 1-5, http://analytical360.com/m/expired/197158.
Satyal, P. et al. "Chemotyping and Determination of Antimicrobial Insecticidal, and Cytotoxic Properties of Wild Grown *Cannabis sativa* from Nepal" Journal of Medicinally Active Plants, Dec. 2014, vol. #3, Issue 1, pp. 9-16.
CBD Crew Sweet and Sour Widow analysis published Nov. 2, 2013, pp. 1-5. http://analytical360.com/m/expired/131803.
CBD Crew Analysis Report; (Critical Mass, Fundacion CANNA; Mar. 21, 2012), pp. 1-2, http://cbdcrew.org/varieties/cbd-critical-mass/.
Analytical 360 Analysis of Sweet n' Sour Widow on May 8, 2014, http://analytical360.com/m/expired/230612.
Analytical 360 Analysis of Critical Mass on Aug. 25, 2014, http://analytical360.com/m/expired/276599.
Kojoma, M. et al., "DNA polymorphisms in the tetrahydrocannabinolic acid (THCA) synthase gene in "drug-type" and "fiber-type" *Cannabis sativa* L", Forensic Science International, Jun. 2, 2006, pp. 132-140, vol. 159, No. 2-3, Elsevier Scientific Publishers Ireland Ltd.
Bertoli, A. et al., "Fibre hemp inflorescences: From crop-residues to essential oil production", Industrial Crops and Products, Nov. 1, 2010, pp. 329-337, vol. 32, No. 3.
Solon, Olivia, "Medical Marijuana Without the High", May 7, 2012, retrieved from the internet: www.wired.com.
CBD-crew front page on Nov. 22, 2014. www.cbdcrew.org.
Casano et al., "Variations in Terpene Profiles of Different Strains of *Cannabis sativa* L." Acta Horticulturae, vol. 925, pp. 115-121, 2011.
CBD Crew variety "Sweet and Sour Widow" retrieved from the internet: https://web.archive.org/web/20120409021918/http://cbdcrew.org/varieties/cbd-sweet-and-sour-widow/, retrieved on Mar. 10, 2017, 2 pages.
De Meijer and Hammond, "The inheritance of chemical phenotype in *Cannabis sativa* L. (V): regulation of the propyl-/pentyl cannabinoid ratio, completion of a genetic model." Euphytica (2016); 210: 291-307.
Halent Laboratories "Test Results for Dougie's Farm H0-21", Test ID# 2960-1, Feb. 13, 2014, 5 pages.

Halent Labs Chemical Analysis for "Pineapple Purps" retrieved from the internet: http://steephilllab.com/thcv-the-sports-car-of-cannabinoids/, retrieved on Mar. 17, 2017, 1 page.
International Preliminary Report on Patentability for International Application No. PCT/US2014/030267 dated Sep. 15, 2015, 10 pages.
International Preliminary Report on Patentability for International Application No. PCT/US2014/046694 dated May 3, 2016, 11 pages.
Steep Hill Halent Cannabis Analytics and Research: "Dougs Varin Decarb THCV Std.", Steep Hill Labs, Inc., Reported Jun. 10, 2014, retrieved from the internet: http://steephilllab.com/wp-content/uploads/2014/07/DougsVarinKief_Decarbed.pdf, retrieved on Mar. 17, 2017, 3 pages.
Steep Hill Halent Cannabis Analytics and Research. "Dougs Varin THCVA Std.", Steep Hill Labs, Inc., Reported Jun. 10, 2014, retrieved from the internet: http://steephilllab.com/wp-content/uploads/2014/07/DougsVarinKief.pdf, retrieved on Mar. 17, 2017, 3 pages.
Written Opinion for International Application No. PCT/US2014/030267 dated Nov. 7, 2014, 9 pages.
Written Opinion for International Application No. PCT/US2014/046694 dated May 1, 2015, 10 pages.
Analytical 360 Analysis of CBD Crew Nordle on Apr. 3, 2014, http://archive.analytical360.com/m/archived/214253, 3 pages.
Analytical 360 Analysis of Girl Scout Cookie (Patient Solutions) on Jun. 23, 2014, https://web.archive.org/web/20140628182810/http://analytical360.com/m/flowers/251990, 3 pages.
Analytical 360 Analysis of Omrita Rx on Feb. 20, 2014, http://archive.analytical360.com/m/archived/192732, 3 pages.
"CBD Strains From Europe Grown out in California." O'Shaughnessy's News Services (Winter/Spring 2013), The Journal of Cannabis in Clinical Practice. Also available online at: www.beyondthc.com/wp-content/uploads/2013/03/PCBD-update-22-26.pdf.
"CBD: A Patient's Guide to Medical Cannabis." by Leinow & Birnbaum, North Atlantic Books, Berkeley, California (2017), Chapter 9 Alphabetized list of High-CBD Strains, pp. 250-252, 10 pages.
"Terpenoids, 'minor' cannabinoids contribute to 'entourage effect' of Cannabis-based medicines." by Gardner, O'Shaughnessy's News Services, The Journal of Cannabis in Clinical Practice (Autumn 2011), p. 1 and 19-21, 4 pages, Available online at http://www.beyondthc.com/wp-content/uploads/2012/08/EntourageEffect.pdf.
"The Release of Omrita Rx3." O'Shaughnessy's News Service (Autumn 2011), p. 15, 1 page, Also available online at http://www.beyondthc.com/wpcontent/uploads/2012/07/CBDiary2.pdf.
CBD Crew Strain, "CBD Nordle" Sep. 6, 2014 and retrieved from the internet at http://web.archive.org/web/20140906010255/http://cbdcrew.org:80/lab-results/cbd-nordle/ 2 pages.
Pertwee, RG., "Emerging strategies for exploiting cannabinoid receptor agonists as medicines." Br J Pharmacol. (2009); 156 (3): 397-411.
Gieringer, D., "Cannabis "Vaporization": A Promising Strategy for Smoke Harm Reduction." Journal of Cannabis Therapeutics (2001); 1 (3-4): 153-170.
Klingeren and Ham, "Antibacterial activity of $\Delta^9$-tetrahydrocannabinol and cannabidiol", Antonie van Leeuwenhoek (1976); 42 (1-2): 9-12.
Analytical 360, Test results for "Nordle", Jun. 22, 2013 (Jun. 22, 2013), retrieved from the internet: http://archive.analytical360.com/m/archived/79871, retrieved on May 29, 2019.
Analytical 360, Test results for "Nordle", Jan. 8, 2014 (Jan. 8, 2014), retrieved from the Internet: http://archive.analytical360.com/m/archived/166950, retrieved on May 29, 2019.
Booth et al., "Terpene synthases from *Cannabis sativa*," PLoS ONE (2017) 12(3): e0173911, 20 pages.
Grotenherman et al., "The therapeutic potential of cannabis and cannabinoids", Dtsch Arztebl Int., vol. 109, No. 29-30, pp. 495-501, 2012.
Hazekamp and Fischedick, "Cannabis—from cultivar to chemovar", Drug Testing and Analysis, vol. 4, pp. 660-667, 2012, published online Feb. 24, 2012 (Feb. 24, 2012).
Hillig, "A chemotaxonomic analysis of terpenoid variation in Cannabis," Biochemical Systematics and Ecology (2004), 32:875-891.

(56) References Cited

OTHER PUBLICATIONS

Ito et al., "The sedative effect of inhaled terpinolene in mice and its structure-activity relationships," Journal of Natural Medicines, 2013, vol. 67, Issue 4, pp. 833-837, published online Jan. 22, 2013 (Jan. 22, 2013).

Okumura et al., "Terpinolene, a component of herbal sage, downregulates AKT1 expression in K562 cells", Oncology Letters, vol. 3, pp. 321-324, 2012.

* cited by examiner

BREEDING, PRODUCTION, PROCESSING AND USE OF MEDICAL CANNABIS

CROSS-REFERENCE TO RELATED APPLICATIONS

This application claims the benefit of U.S. provisional application No. 61/801,528 filed on Mar. 15, 2013 which is hereby incorporated by reference in its entirety including all descriptions, references, figures, and claims for all purposes.

FIELD OF THE INVENTION

The invention relates to *cannabis* plants for medical use, compositions and methods for making and using said *cannabis* plants and compositions derived thereof.

BACKGROUND OF THE INVENTION

*Cannabis*, more commonly known as marijuana, is a genus of flowering plants that includes at least three species, *Cannabis sativa*, *Cannabis indica*, and *Cannabis ruderalis*. The use of *cannabis* for social and medical purposes has been known for almost of all humanity's recorded history. *Cannabis* is most commonly administered via inhalation or consumption of marijuana-infused food and drink.

Since 1972 marijuana has been classified as a Schedule I drug under the U.S. Controlled Substances Act because the U.S. Federal Government considers it to have "no accepted medical use." In stark contrast to this position, 18 of the 50 U.S. states and the District of Columbia have recognized the medical benefits of *cannabis* and have decriminalized its medical use. The 18 U.S. states where medical marijuana has been decriminalized as of the filing date of the present application are as follows: Alaska, Arizona, California, Colorado, Connecticut, Delaware, Hawaii, Maine, Massachusetts, Michigan, Montana, Nevada, New Jersey, New Mexico, Oregon, Rhode Island, Vermont and Washington. The residency requirements, approved list of conditions/diseases, and the other laws/rules regarding the possession and cultivation of medical marijuana generally differ by state.

Despite the official position of the U.S. Federal Government and as recognized by the states that have legalized it, *cannabis* has been shown to provide substantial and varied medical benefits. *Cannabis* is regularly used by a wide cross-section of society to treat a variety of maladies, conditions and symptoms including, but not limited to, the following: nausea, glaucoma, lack of appetite, mucous membrane inflammation, epilepsy, leprosy, fever, obesity, asthma, urinary tract infections, coughing, anorexia associated with weight loss in AIDS patients, pain, and multiple sclerosis.

*Cannabis* intoxication (i.e., euphoria, relaxation) can occur and other side effects may also accompany its use, particularly with higher doses, specific *cannabis* varieties and/or over prolonged periods of usage. Undesirable side effects of using the available THC-predominant *cannabis* varieties can include, but are not limited to, the following: decreased short-term memory, dry mouth, impaired visual perception and motor skills, erectile dysfunction, lowers fertility, red (i.e., blood shot) eyes, increased anxiety, occasional infarction, stroke, paranoia, acute psychosis, lowered mental aptitude, hallucinations, bizarre behavior, irrational panic attacks, irrational thoughts and various other cognitive and social problems.

Some of the negative or undesirable side effects from using available *cannabis* varieties for medical purposes are related to the plant's content of the chemical $\Delta^9$-tetrahydrocannabinol (THC). A major hurdle to the more wide-spread acceptance of *cannabis* and its legalization is that the land races and commercially available *cannabis* genotypes (of drug varieties) contain relatively high concentrations of THC. There is a real need for *cannabis* varieties for potential medical use that produce modulated THC concentrations and varying concentrations of other pharmacologically active substances that reduce the negative side effects of THC and increase the medical benefits realized from its use. The inventions described herein meet that long-felt need.

SUMMARY OF THE INVENTION

According to the methods and compositions of the present invention, plants, plant parts, plant tissues and plant cells are produced to contain pentyl, propyl, C-4, C-1 and monomethylether constituents of cannabinoid families, including but not limited to acidic and neutral forms of the cannabigerol, cannabichromene, cannabidiol, delta-9-tetrahydrohydrocannabinol, delta-8-tetrahydrohydrocannabinol, cannabielsoin, cannabinol and cannabinodiol cannabinoid classes; and, cis and trans terpenoids, including but not limited to myrcene, limonene, linalool, ocimene, beta-pinene, alpha-pinene, beta-caryophyllene, alpha-caryophyllene, delta-3-carene, gamma-bisabolene, alpha-farnesene, beta-fenchol, guajol, alpha-guaiene, terpinolene, beta-eudesmol, alpha-bergamotene, epi-alpha-bisabolol and caryophyllene oxide ranging from 0.1% of dry weight of inflorescences, plant parts, plant tissues and plant cells to 35% of inflorescences and/or 95% of plant parts, plant parts, plant tissues and plant cells.

The present invention provides medical *cannabis* plants, plant parts, plant tissues and plant cells which provide a way to deliver a consistent and more medicinally tolerable and effective ratio of cannabinoids ("CBD") to patients (e.g., <THC:>CBD than in presently-available *cannabis* varieties).

The present invention provides Medical *Cannabis* plants, plant parts, plant cells and plant tissues which have an amount, percentage and/or ratio of cannabinoids that is greater than or other than THCA/THC.

The present invention provides Medical *Cannabis* plants, plant parts, plant tissues and plant cells having an alternative cannabinoid (e.g., THCV, CBDV, etc.) to THCA/THC.

In some embodiments, the present invention provides Medical *Cannabis* plants, plant parts, tissues and cells having a THC content that is ≥2.0% but ≤90.0% based on the dry weight of plant inflorescences; and, a CBD content based on the dry weight of plant inflorescences that is ≥1.5%. Thus, the medical *cannabis* plants, plant parts, plant tissues and plant cells of the present invention will have a THC content selected from the group consisting of 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% and 90%; and, a CBD content selected from the group consisting of 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92%, 93%, 94%, 95%, 96%, 97%, 98%, 99.5%, 99.8%, 99.9% and 100%.

In some embodiments, the present invention provides Medical *Cannabis* plants, plant parts, tissues and cells having a THC:CBD ratio of 8:1 and approaching 1:1. By comparison, the THC:CBD ratio of the currently available *cannabis* varieties is 20:1 and approaches 25:1, 30:1, 35:1, 40:1 and higher THC to CBD ratios. Thus, the medical *cannabis* plants, plant parts, plant tissues and plant cells of the present invention will have a THC ratio selected from the group consisting of 8:1, 7:1, 6:1, 5:1, 4:1, 3:1, 2:1 and 1:1.

The present invention provides Classes of *Cannabis* Varieties developed by selection from landraces of mixed *cannabis* genotypes and resulting from further breeding, wherein these Classes of *Cannabis* Varieties can provide useful patient treatment and also are used as breeding material to develop Medical *Cannabis* plants and varieties according to the present invention.

The present invention provides Medical *Cannabis* plants and varieties with increased organoleptic appeal as a result of having specified, predetermined terpene and sesquiterpene profiles and content. In some embodiments of the present invention, the increased organoleptic appeal of the Medical *Cannabis* is inherited in-whole or in-part as a result of using the Classes of *Cannabis* Varieties in the breeding program to develop the Medical *Cannabis* plants. For, example, in some embodiments, Classes of *Cannabis* Varieties with specific terpene and sesquiterpene profiles and content are bred with certain *cannabis* varieties with specific CBD profiles and content to develop Medical *Cannabis* Varieties with the desired combined attributes of the two types of *cannabis* plants.

The present invention also provides methods to determine higher THC adequate to down-regulate the entire CB system. This method uses the 'down-regulation' as therapy for hyper-endocannabinoid systems and to help increase the therapeutic margin. Additionally, the present invention provides for a potential role of dosage and its influence on biosynthesis and build-up of cholesterol; a healthy means of supplementing the endocannabinoid system when consuming an ultra low-cholesterol diet.

The present invention also provides methods for determining the terpene profiles at which 'dosages' are suitable for outcomes related to mood elevation and/or sedation (i.e., high limonene for energy, high myrcene for sleep aid, etc.). Furthermore, according to the present invention, terpenes such as beta-caryophyllene are used in pain studies (anti-inflammatory via PGE) and linalool is used for anxiety (anti-anxiety and sedative).

DETAILED DESCRIPTION OF THE INVENTION

Figure 1:
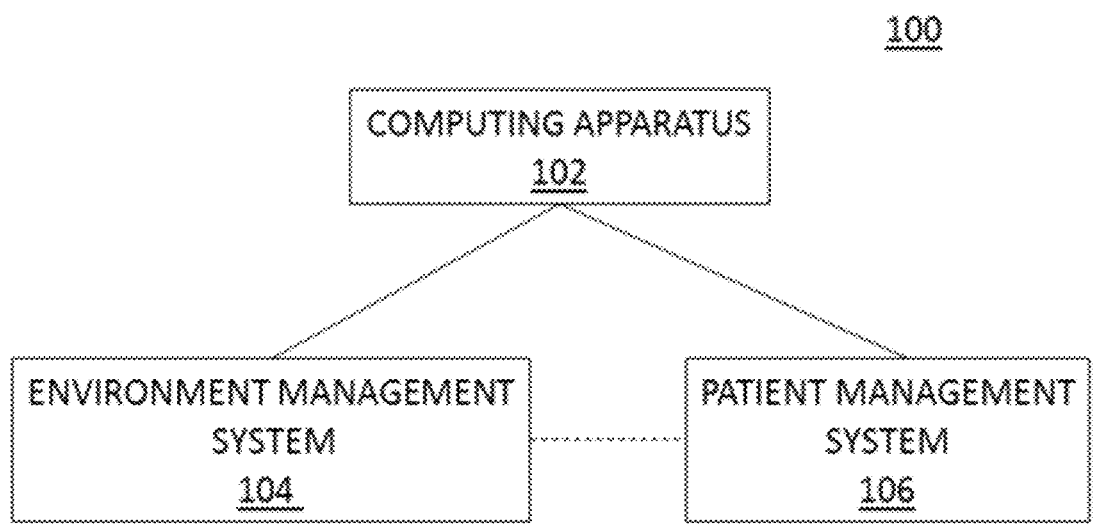
FIG. 1—illustrates a system 100 for feedback-based cultivation of the herbal medicines described herein.

All publications, patents and patent applications, including any drawings and appendices, are herein incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

The invention provides *cannabis* plants. As used herein, the term "plant" refers to plants in the genus of *Cannabis* and plants derived thereof.

The invention provides plant parts. As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein, a "landrace" refers to a local variety of a domesticated plant species which has developed largely by natural processes, by adaptation to the natural and cultural environment in which it lives. The development of a landrace may also involve some selection by humans but it differs from a formal breed which has been selectively bred deliberately to conform to a particular formal, purebred standard of traits.

The *International Code of Zoological Nomenclature* defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species.

The invention provides plant cultivars. As used herein, the term "cultivar" means a group of similar plants that by structural features and performance (i.e., morphological and physiological characteristics) can be identified from other varieties within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "inbreeding" refers to the production of offspring via the mating between relatives. The plants resulting from the inbreeding process are referred to herein as "inbred plants" or "inbreds."

The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

The invention provides samples. As used herein, the term "sample" includes a sample from a plant, a plant part, a plant cell, or from a transmission vector, or a soil, water or air sample.

The invention provides offspring. As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The invention provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

The invention provides donor plants and recipient plants. As used herein, "donor plants" refer to the parents of a variety which contains the gene or trait of interest which is desired to be introduced into a second variety (e.g., "recipient plants").

In some embodiments, the present invention provides methods for obtaining plant genotypes comprising recombinant genes. As used herein, the term "genotype" refers to the genetic makeup of an individual cell, cell culture, tissue, organism (e.g., a plant), or group of organisms.

In some embodiments, the present invention provides homozygotes. As used herein, the term "homozygote" refers to an individual cell or plant having the same alleles at one or more loci.

In some embodiments, the present invention provides homozygous plants. As used herein, the term "homozygous" refers to the presence of identical alleles at one or more loci in homologous chromosomal segments.

In some embodiments, the present invention provides hemizygotes. As used herein, the term "hemizygotes" or "hemizygous" refers to a cell, tissue, organism or plant in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterozygotes. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest which is under control of the synthetic regulatory element.

The invention provides methods for obtaining plant lines comprising recombinant genes. As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

The invention provides open-pollinated populations. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

The invention provides self-pollination populations. As used herein, the term "self-crossing", "self pollinated" or "self-pollination" means the pollen of one flower on one plant is applied (artificially or naturally) to the ovule (stigma) of the same or a different flower on the same plant.

The invention provides ovules and pollens of plants. As used herein when discussing plants, the term "ovule" refers to the female gametophyte, whereas the term "pollen" means the male gametophyte.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

The invention provides methods for obtaining plants comprising recombinant genes through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

The invention provides transformants comprising recombinant genes. As used herein, the term "transformant" refers to a cell, tissue or organism that has undergone transformation. The original transformant is designated as "T0" or "$T_0$." Selfing the T0 produces a first transformed generation designated as "T1" or "$T_1$."

In some embodiments, the present invention provides plant varieties comprising the recombinant genes. As used herein, the term "variety" refers to a subdivision of a species, consisting of a group of individuals within the species that are distinct in form or function from other similar arrays of individuals.

In some embodiments, the present invention provides organisms with recombinant genes. As used herein, an "organism" refers any life form that has genetic material comprising nucleic acids including, but not limited to, prokaryotes, eukaryotes, and viruses. Organisms of the present invention include, for example, plants, animals, fungi, bacteria, and viruses, and cells and parts thereof.

Cannabis

Cannabis has long been used for fibre (hemp), for seed and seed oils, for medicinal purposes, and as a recreational drug. Industrial hemp products are made from Cannabis plants selected to produce an abundance of fiber. Some Cannabis strains have been bred to produce minimal levels of THC, the principal psychoactive constituent responsible for the psychoactivity associated with marijuana. Marijuana consists of the dried flowers of Cannabis plants selectively bred to produce high levels of THC and other psychoactive cannabinoids. Various extracts including hashish and hash oil are also produced from the plant.

Cannabis is an annual, dioecious, flowering herb. The leaves are palmately compound or digitate, with serrate leaflets. Cannabis normally has imperfect flowers, with staminate "male" and pistillate "female" flowers occurring on separate plants. It is not unusual, however, for individual plants to bear both male and female flowers. Although monoecious plants are often referred to as "hermaphrodites," true hermaphrodites (which are less common) bear staminate and pistillate structures on individual flowers, whereas monoecious plants bear male and female flowers at different locations on the same plant.

Cannabis is diploid, having a chromosome complement of 2n=20, although polyploid individuals have been artificially produced. The first genome sequence of Cannabis, which is estimated to be 820 Mb in size, was published in 2011 by a team of Canadian scientists.

All known strains of Cannabis are wind-pollinated and the fruit is an achene. Most strains of Cannabis are short day plants, with the possible exception of C. sativa subsp. sativa var. spontanea (=C. ruderalis), which is commonly described as "auto-flowering" and may be day-neutral.

The genus Cannabis was formerly placed in the Nettle (Urticaceae) or Mulberry (Moraceae) family, and later, along with the Humulus genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

Cannabis plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the cannabis plant (Rudolf Brenneisen, 2007, Chemistry and Analysis of Phytocannabinoids and Other Cannabis Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from Cannabis sativa L", Pharmacology Biochemistry and Behavior 95 (4): 434-42; incorporated herein by reference). The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

The cannabinoids in cannabis plants include, but are not limited to, $\Delta^9$-Tetrahydrocannabinol ($\Delta^9$-THC), $\Delta^8$-Tetrahydrocannabinol ($\Delta^8$-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta^9$-Tetrahydrocannabivarin (THCV), cannabichromevarin (CBCV), and cannabigerovarin (CBGV). See Holley et al. (Constituents of Cannabis sativa L. XI Cannabidiol and cannabichromene in samples of known geographical origin, J. Pharm. Sci. 64:892-894, 1975) and De Zeeuw et al. (Cannabinoids with a propyl side chain in Cannabis, Occurrence and chromatographic behavior, Science 175:778-779), each of which is herein incorporated by reference in its entirety for all purposes.

Cannabis plants also produce many types of terpenoids, including, but not limited to, limonene, myrcene, a-pinene, linalool, b-caryophyllene, caryophyllene oxide, nerolidol and phytol.

U.S. Pat. No. 6,630,507, assigned on the patent face to The United States of America, is directed to methods of treating diseases caused by oxidative stress by administering therapeutically effective amounts of a CBD that has substantially no binding to the N-methyl-D-aspartate (NMDA) receptor, wherein the CBD acts as an antioxidant and neuroprotectant.

In one embodiment, the present invention provides medical cannabis plants, which are distinct from the traditional recreational marijuana plants.

As used herein, 'medical cannabis' or 'Medical Cannabis' refer to cannabis plants, lines, varieties and cultivars having a THC oil content based on the dry weight of plant inflorescences of greater than or equal to 2.0% but less than or equal to 90% (i.e., THC of ≥2.0% and ≤90%) and having a CBD oil content based on the dry weight of plant inflorescences equal to or greater than 1.5% (i.e., CBD of ≥1.5%); or, alternatively, having a THC:CBD ratio of 8:1 and approaching 1:1 based on the dry weight of plant inflorescences.

As a result of the present invention, select *cannabis* varieties can be used as a physician-recommended form of medicine or herbal therapy without causing any side effects, or with reduced general or specific side effects when compared to recreational marijuana plants. Methods for administration of medical *cannabis* include, but are not limited to, vapor inhalation, smoking (e.g., dried buds), drinking, eating extracts, and taking capsules.

Cannabis Chemistry

Cannabinoids are a class of diverse chemical compounds that activate cannabinoid receptors. Cannabinoids produced by plants are called phytocannabinoids, a.k.a., natural cannabinoids, herbal cannabinoids, and classical cannabinoids. At least 85 different cannabinoids have been isolated from the *cannabis* plants (El-Alfy et al., 2010, "Antidepressant-like effect of delta-9-tetrahydrocannabinol and other cannabinoids isolated from Cannabis sativa L", Pharmacology Biochemistry and Behavior 95 (4): 434-42; Brenneisen, supra) Typical cannabinoids isolated from *cannabis* plants include, but are not limited to, Tetrahydrocannabinol (THC), Cannabidiol (CBD), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol Monomethyl Ether). In the *Cannabis* plant, cannabinoids are synthesized and accumulated as cannabinoid acids (e.g., cannabidiolic acid (CBDA)). When the herbal product is dried, stored, or heated, the acids decarboxylize gradually or completely into neutral forms (e.g., CBDA→CBD).

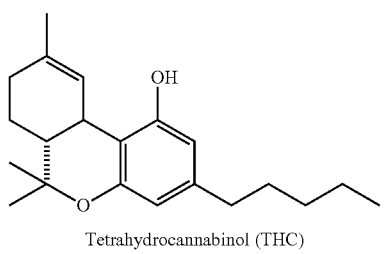

Tetrahydrocannabinol (THC)

As known as delta-9-tetrahydrocannabinol (Δ9-THC), THC is the principal psychoactive constituent (or cannabinoid) of the *cannabis* plant. The initially synthesized and accumulated form in plant is THC acid (THCA).

THC has mild to moderate analgesic effects, and *cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003). "Drugs of abuse and the elicitation of human aggressive behavior". *Addictive Behaviors* 28: 1533-1554).

The pharmacological actions of THC result from its partial agonist activity at the cannabinoid receptor $CB_1$, located mainly in the central nervous system, and the $CB_2$ receptor, mainly expressed in cells of the immune system (Pertwee, 2006, "The pharmacology of cannabinoid receptors and their ligands: An overview". *International Journal of Obesity* 30: S13-S18.) The psychoactive effects of THC are primarily mediated by its activation of CB1G-protein coupled receptors, which result in a decrease in the concentration of the second messenger molecule cAMP through inhibition of adenylate cyclase (Elphick et al., 2001, "The neurobiology and evolution of cannabinoid signalling". *Philosophical Transactions of the Royal Society B: Biological Sciences* 356 (1407): 381-408.) It is also suggested that THC has an anticholinesterase action which may implicate it as a potential treatment for Alzheimer's and Myasthenia (Eubanks et al., 2006, "A Molecular Link Between the Active Component of Marijuana and Alzheimer's Disease Pathology". Molecular Pharmaceutics 3 (6): 773-7.)

In the *cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulone in hops. See Fellermeier et al., (1998, "Prenylation of olivetolate by a hemp transferase yields cannabigerolic acid, the precursor of tetrahydrocannabinol". *FEBS Letters* 427 (2): 283-5); de Meijer et al. I, II, III, and IV (I: 2003, Genetics, 163:335-346; II: 2005, *Euphytica,* 145:189-198; III: 2009, *Euphytica,* 165:293-311; and IV: 2009, *Euphytica,* 168:95-112.) Non-limiting examples of THC variants include:

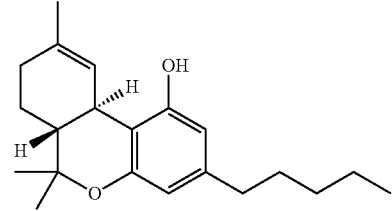

Δ⁹-Tetrahydrocannabinol

Δ⁹-THC-C₅

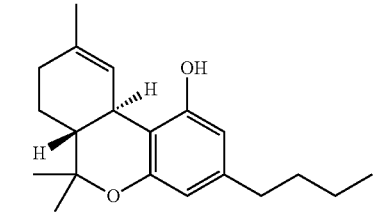

Δ⁹-Tetrahydrocannabinol-C₄

Δ⁹-THC-C₄

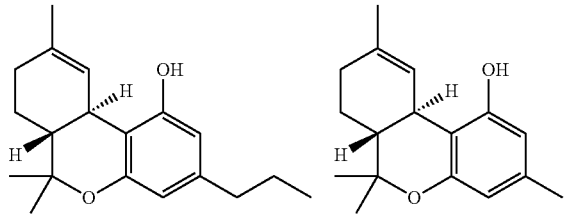

Δ⁹-Tetrahydrocannabivarin     Δ⁹-Tetrahydrocannabiorcol

Δ⁹-THCV-C₃              Δ⁹-THCO-C₁

-continued

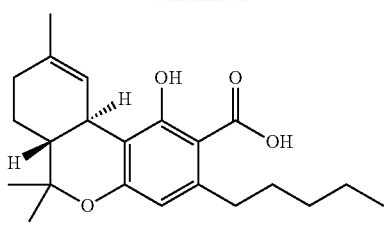

Δ⁹-Tetrahydrocannabinolic acid A

Δ⁹-THCA-C₅ A

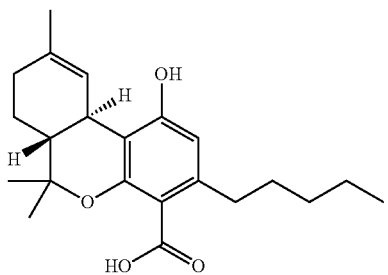

Δ⁹-Tetrahydrocannabinolic acid B

Δ⁹-THCB-C₅ B

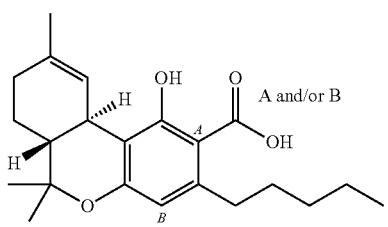

Δ⁹-Tetrahydrocannabinolic acid-C₄
A and/or B

Δ⁹-THCA-C₄
A and/or B

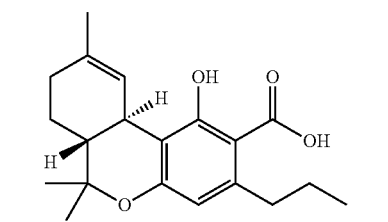

Δ⁹-Tetrahydrocannabivarinic acid A

Δ⁹-THCVA-C₃ A

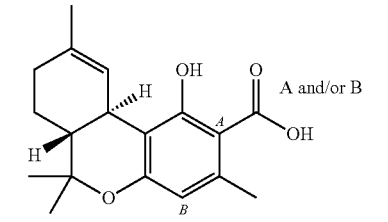

Δ⁹-Tetrahydrocannabiorcolic acid
A and/or B

Δ⁹-THCOA-C₁
A and/or B

-continued

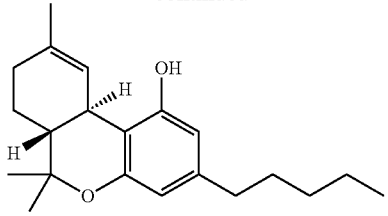

(-)-Δ⁸-trans-(6aR, 10aR)-Δ⁸-Tetrahydrocannabinol

Δ⁸-THC-C₅

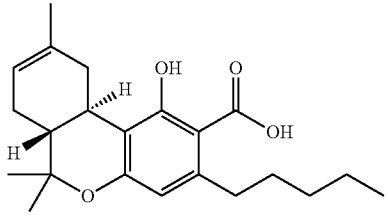

(-)-Δ⁸-trans-(6aR, 10aR)-Tetrahydrocannabinolic acid A

Δ⁸-THCA-C₅ A

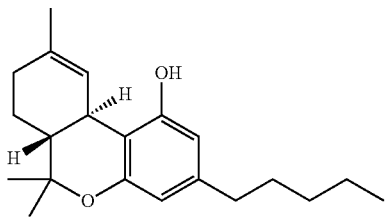

(-)-(6aS, 10aR)-Δ⁹-Tetrahydrocannabinol (-)-cis-Δ⁹-THC-C₅

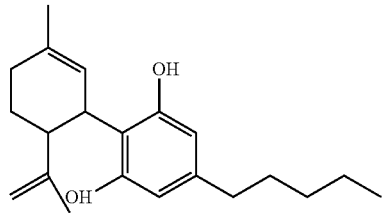

Cannabidiol (CBD)

CBD is a cannabinoid found in *cannabis*. It is a major constituent of the plant. Cannabidiol has displayed sedative effects in animal tests (Pickens, 1981, "Sedative activity of *cannabis* in relation to its delta'-trans-tetrahydrocannabinol and cannabidiol content". *Br. J. Pharmacol.* 72 (4): 649-56). Some research, however, indicates that CBD can increase alertness, and attenuate the memory-impairing effect of THC. (Nicholson et al., June 2004, "Effect of Delta-9-tetrahydrocannabinol and cannabidiol on nocturnal sleep and early-morning behavior in young adults" *J Clin Psychopharmacol* 24 (3): 305-13; Morgan et al., 2010, "Impact of cannabidiol on the acute memory and psychotomimetic effects of smoked *cannabis*: naturalistic study, *The British Journal of Psychiatry*, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, "Cannabidiol—recent advances". *Chemistry & Biodiversity* 4 (8): 1678-1692.) Recent studies have shown cannabidiol to be as effective as atypical antipsychotics in treating schizophrenia (Zuardi et al., 2006, "Cannabidiol, a *Cannabis sativa* constituent, as an antipsychotic drug" *Braz. J. Med. Biol. Res.* 39 (4): 421-429.). Studies have also shown that it may relieve symptoms of dystonia (Consroe, 1986, "Open label evaluation of cannabidiol in dystonic movement disorders". *The International journal of neuroscience* 30 (4): 277-282). CBD reduces growth of aggressive human breast cancer cells in vitro and reduces their invasiveness (McAllister et al., 2007, "Cannabidiol as a novel inhibitor of Id-1 gene expression in aggressive breast cancer cells". *Mol. Cancer Ther.* 6 (11): 2921-7.)

Cannabidiol has shown to decrease activity of the limbic system (de Souza Crippa et al., "Effects of Cannabidiol (CBD) on Regional Cerebral Blood Flow". *Neuropsychopharmacology* 29 (2): 417-426.) and to decrease social isolation induced by THC (Malon et al., "Cannabidiol reverses the reduction in social interaction produced by low dose Δ9-tetrahydrocannabinol in rats". Pharmacology Biochemistry and Behavior 93 (2): 91-96.) It's also shown that Cannabidiol reduces anxiety in social anxiety disorder (Bergamaschi et al., 2003, "Cannabidiol Reduces the Anxiety Induced by Simulated Public Speaking in Treatment-Naïve Social Phobia Patients". *Neuropsychopharmacology* 36 (6): 1219-1226). Cannabidiol has also been shown as being effective in treating an often drug-induced set of neurological movement disorders known as dystonia (Snider et al., 1985, "Beneficial and Adverse Effects of Cannabidiol in a Parkinson Patient with Sinemet-Induced Dystonic Dyskinesia". *Neurology*, (Suppl 1): 201.) Morgan et al. reported that strains of *cannabis* which contained higher concentrations of Cannabidiol did not produce short-term memory impairment vs. strains which contained similar concentrations of THC (2010, "Impact of cannabidiol on the acute memory and psychotomimetic effects of smoked *cannabis*: naturalistic study: naturalistic study [corrected." ]. *British Journal of Psychiatry* 197 (4): 285-90.)

Cannabidiol has no affinity for $CB_1$ and $CB_2$ receptors but acts as an indirect antagonist of cannabinoid agonists. CBD is an antagonist at the putative new cannabinoid receptor, GPR55. Cannabidiol has also been shown to act as a 5-HT1A receptor agonist, an action which is involved in its antidepressant, anxiolytic, and neuroprotective effects. Cannabidiol is also an allosteric modulator at the Mu and Delta opioid receptor sites.

*Cannabis* produces CBD-carboxylic acid through the same metabolic pathway as THC, until the last step, where CBDA synthase performs catalysis instead of THCA synthase. See Marks et al. (2009, "Identification of candidate genes affecting Δ9-tetrahydrocannabinol biosynthesis in *Cannabis sativa*". Journal of Experimental Botany 60 (13): 3715-3726.) and Meijer et al. I, II, III, and IV. Non-limiting examples of CBD variants include:

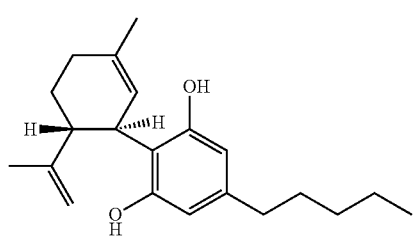

(-)-Cannabidiol

CBD—$C_5$

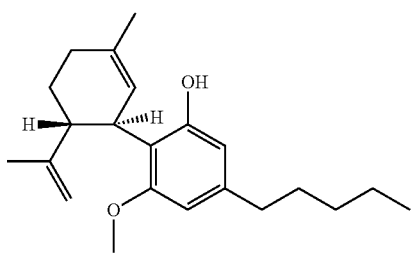

Cannabidiol momomethyl ether

CBDM—$C_5$

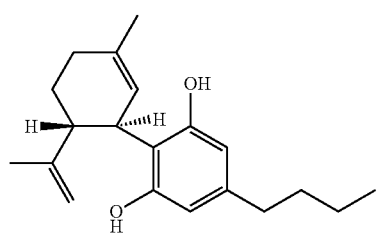

Cannabidiol-$C_4$

CBD—$C_4$

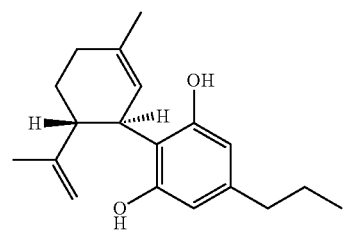

(-)-Cannabidivarin

CBDV—$C_3$

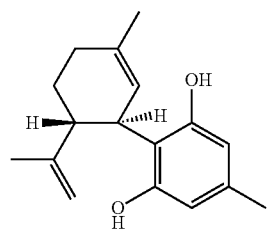

Cannabidiorcol

CBD—$C_1$

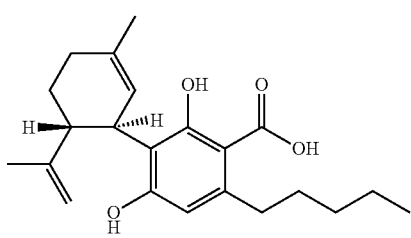

Cannabidiolic acid

CBDA—$C_5$

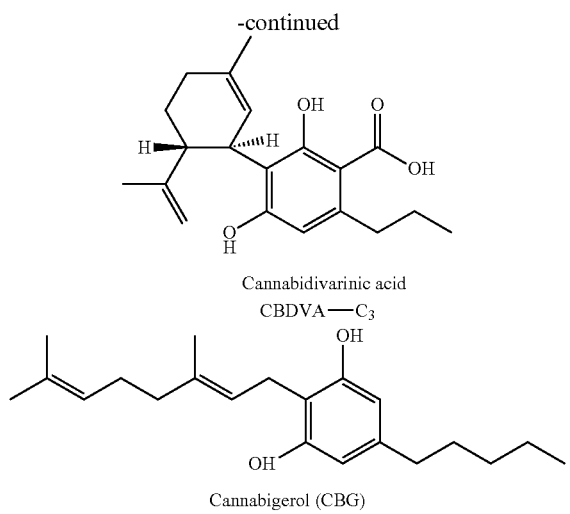

Cannabidivarinic acid
CBDVA—C$_3$

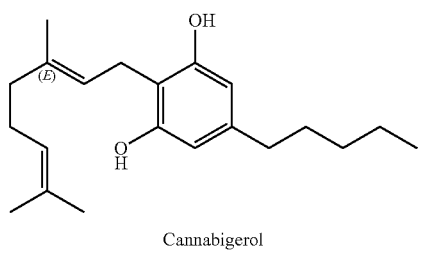

Cannabigerol (CBG)

CBG is a non-psychoactive cannabinoid found in the *Cannabis* genus of plants. Cannabigerol is found in higher concentrations in hemp rather than in varieties of *Cannabis* cultivated for high THC content and their corresponding psychoactive properties. Cannabigerol has been found to act as a high affinity α2-adrenergic receptor agonist, moderate affinity 5-HT1A receptor antagonist, and low affinity CB$_1$ receptor antagonist. It also binds to the CB$_2$ receptor. Cannabigerol has been shown to relieve intraocular pressure, which may be of benefit in the treatment of glaucoma. Non-limiting examples of CBG variants include:

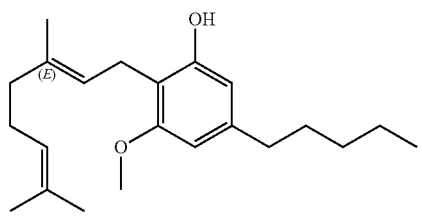

Cannabigerol
(E)-CBG-C$_5$

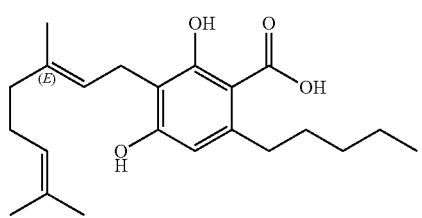

Cannabigerol monomethyl ether
(E)-CBGM-C$_5$ A

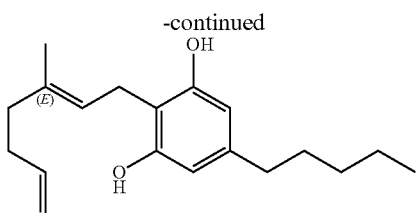

Cannabinerolic acid A
(Z)-CBGA-C$_5$ A

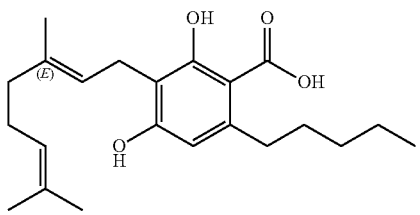

Cannabigerovarin
(E)-CBGV-C$_3$

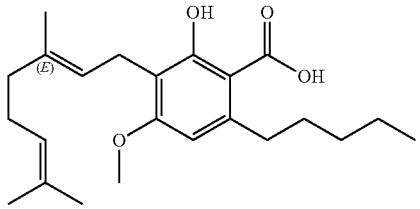

Cannabigerolic acid A
(E)-CBGA-C$_5$ A

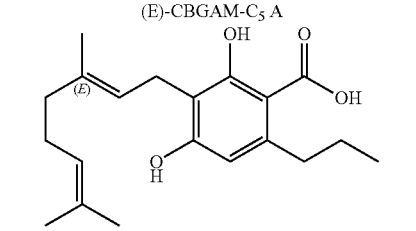

Cannabigerolic acid A monomethyl ether
(E)-CBGAM-C$_5$ A

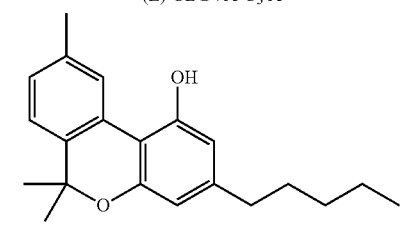

Cannabigerovarinic acid A
(E)-CBGVA-C$_3$ A

Cannabinol (CBN)

CBN is a psychoactive substance cannabinoid found in *Cannabis sativa* and *Cannabis indica/afghanica*. It is also a metabolite of tetrahydrocannabinol (THC). CBN acts as a weak agonist of the CB1 and CB2 receptors, with lower affinity in comparison to THC. Non-limiting examples of CBN variants include

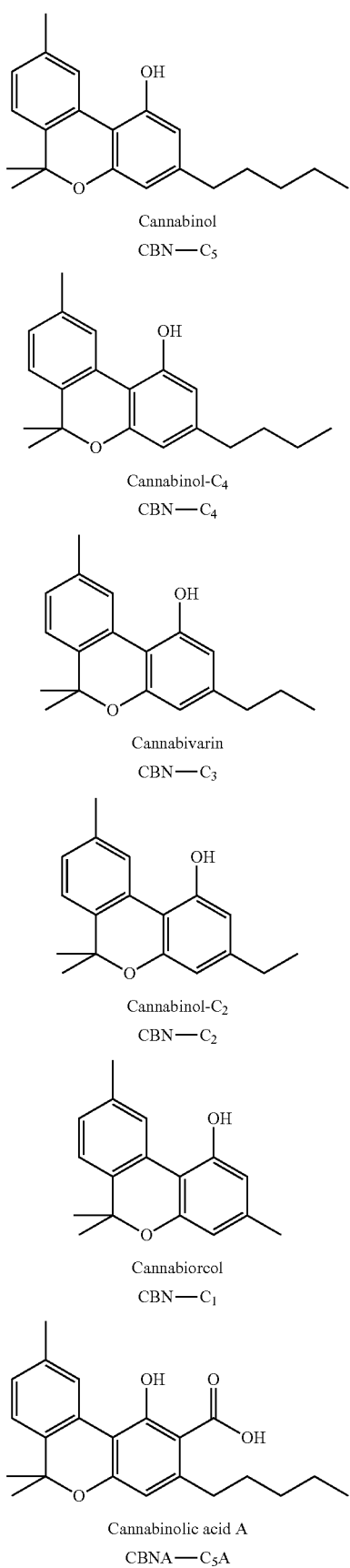

Cannabinol
CBN—C$_5$

Cannabinol-C$_4$
CBN—C$_4$

Cannabivarin
CBN—C$_3$

Cannabinol-C$_2$
CBN—C$_2$

Cannabiorcol
CBN—C$_1$

Cannabinolic acid A
CBNA—C$_5$A

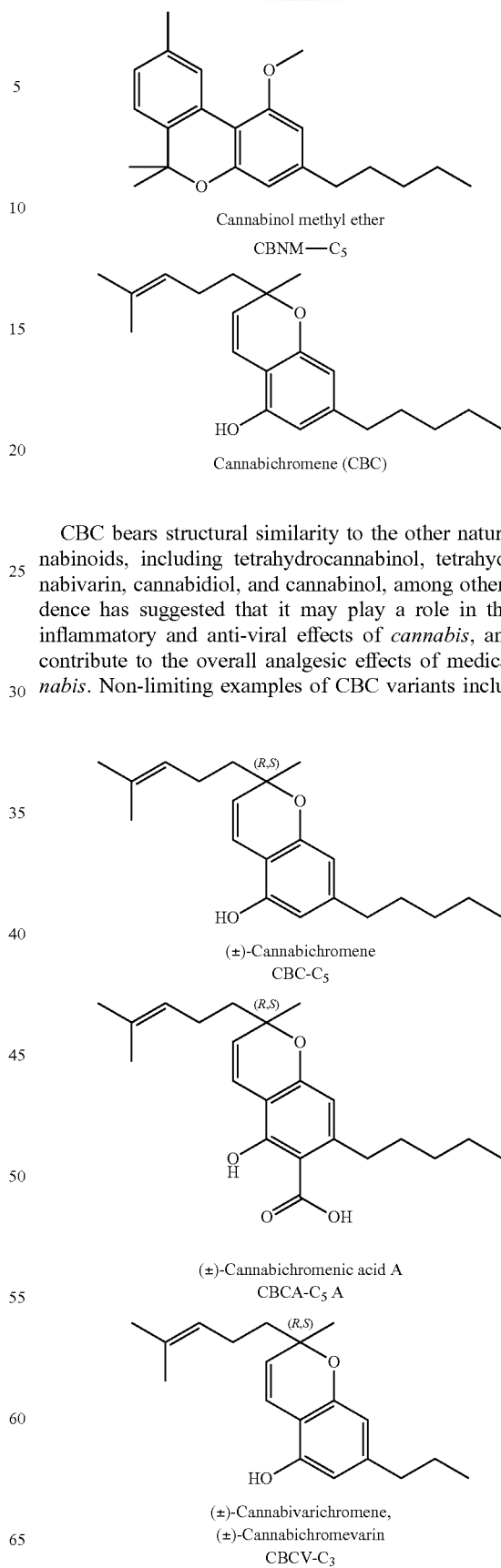

Cannabinol methyl ether
CBNM—C$_5$

Cannabichromene (CBC)

CBC bears structural similarity to the other natural cannabinoids, including tetrahydrocannabinol, tetrahydrocannabivarin, cannabidiol, and cannabinol, among others. Evidence has suggested that it may play a role in the anti-inflammatory and anti-viral effects of *cannabis*, and may contribute to the overall analgesic effects of medical *cannabis*. Non-limiting examples of CBC variants include:

(±)-Cannabichromene
CBC-C$_5$ (±)-Cannabichromenic acid A
CBCA-C$_5$A (±)-Cannabivarichromene,
(±)-Cannabichromevarin
CBCV-C$_3$

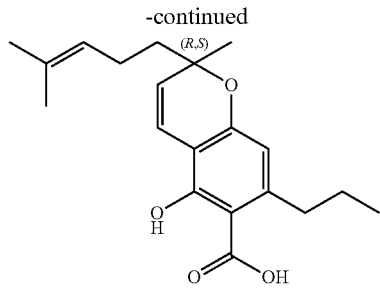

(±)-Cannabichromevarinic
acid A
CBCVA-C₃ A

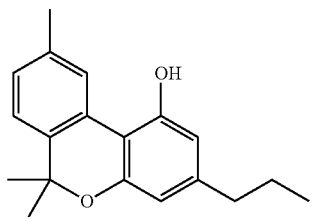

Cannabivarin (CBV)

Cannabivarin, also known as cannabivarol or CBV, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

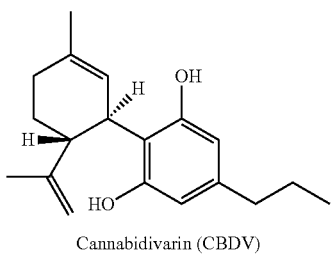 [SMILES: C=C(C)[C@@H]1CCC(C)=C[C@H]1c1c(O)cc(CCC)cc1O]

Cannabidivarin (CBDV)

CBDV is a non-psychoactive cannabinoid found in *Cannabis*. It is a homolog of cannabidiol (CBD), with the side-chain shortened by two methylene bridges (CH2 units). Plants with relatively high levels of CBDV have been reported in feral populations of *C. indica* (=*C. sativa* ssp. indica var. kafiristanica) from northwest India, and in hashish from Nepal.

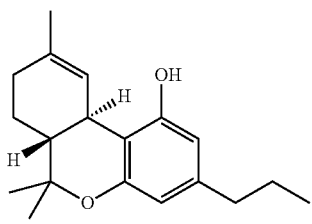

Tetrahydrocannabivarin (THCV, THV)

THCV, or THV is a homologue of tetrahydrocannabinol (THC) having a propyl (3-carbon) side chain. This terpenophenolic compound is found naturally in *Cannabis*, sometimes in significant amounts. Plants with elevated levels of propyl cannabinoids (including THCV) have been found in populations of *Cannabis sativa* L. ssp. indica (=*Cannabis indica* Lam.) from China, India, Nepal, Thailand, Afghanistan, and Pakistan, as well as southern and western Africa. THCV has been shown to be a CB1 receptor antagonist, i.e. it blocks the effects of THC.

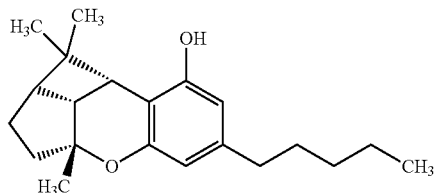

Cannabicyclol (CBL)

Cannabicyclol (CBL) is a non-psychotomimetic cannabinoid found in the *Cannabis* species. CBL is a degradative product like cannabinol. Light converts cannabichromene to CBL. Non-limiting examples of CBL variants include:

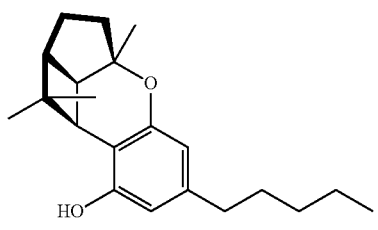

(±)-(1aS,3aR,8bR,8cR)-
Cannabicyclol
CBL-C₅

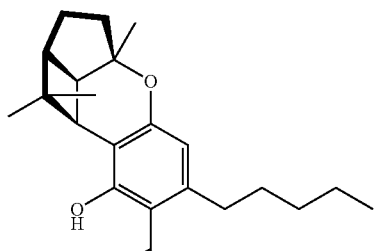

(±)-(1aS,3aR,8bR,8cR)-
Cannabicyclolic acid A
CBLA-C₅ A

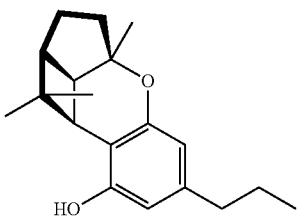

(±)-(1aS,3aR,8bR,8cR)-
Cannabicyclovarin
CBLV-C₃

-continued

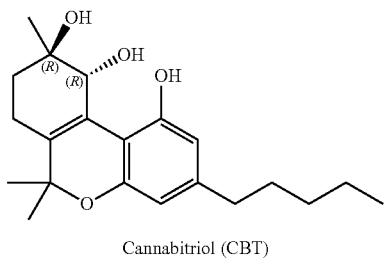

Cannabitriol (CBT)

Non-limiting examples of CBT variants include:

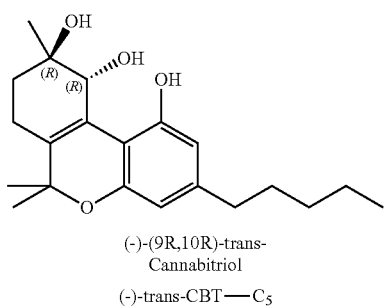

(−)-(9R,10R)-trans-
Cannabitriol
(−)-trans-CBT—C$_5$

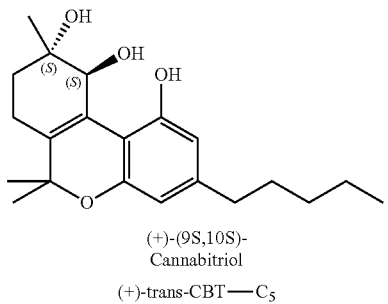

(+)-(9S,10S)-
Cannabitriol
(+)-trans-CBT—C$_5$

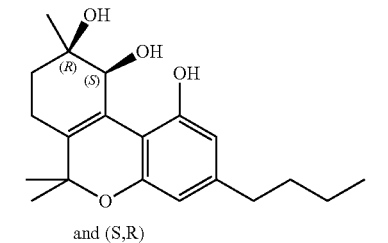

and (S,R)

(±)-
(9R,10S/9S,10R)-
Cannabitriol
(±)-cis-CBT—C$_5$

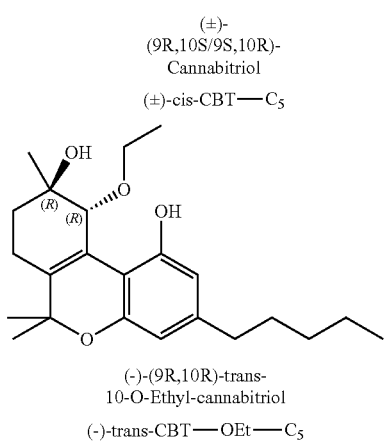

(−)-(9R,10R)-trans-
10-O-Ethyl-cannabitriol
(−)-trans-CBT—OEt—C$_5$

-continued

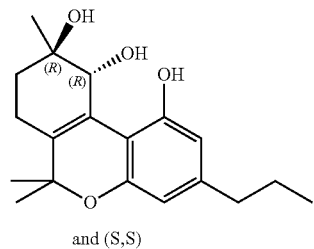

and (S,S)

(±)-
(9R,10R/9S,10S)-
Cannabitriol-C$_3$
(±)-trans-CBT—C$_3$

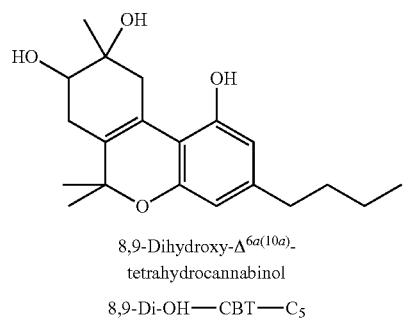

8,9-Dihydroxy-Δ$^{6a(10a)}$-
tetrahydrocannabinol
8,9-Di-OH—CBT—C$_5$

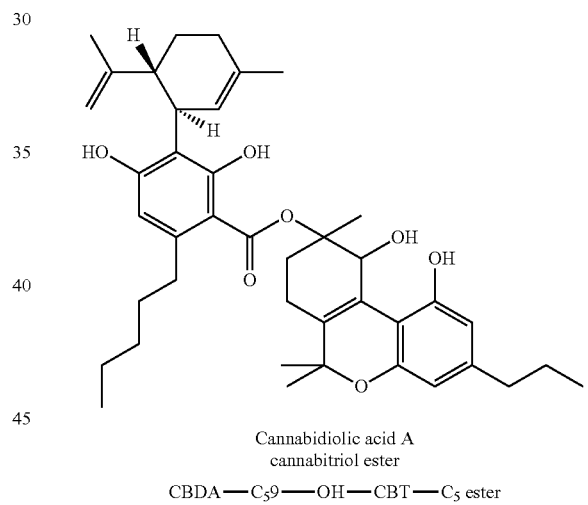

Cannabidiolic acid A
cannabitriol ester
CBDA—C$_5$9—OH—CBT—C$_5$ ester

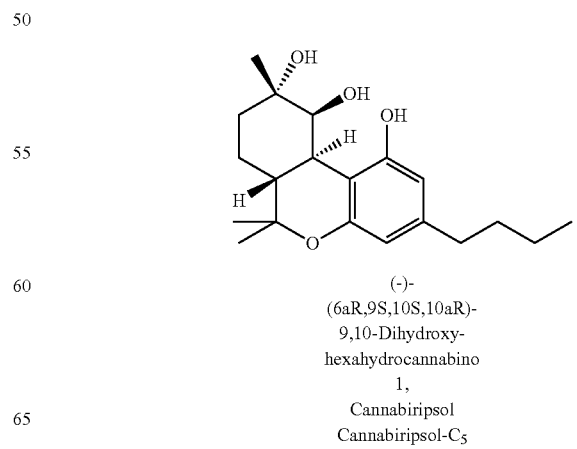

(−)-
(6aR,9S,10S,10aR)-
9,10-Dihydroxy-
hexahydrocannabino
1,
Cannabiripsol
Cannabiripsol-C$_5$ 23
-continued

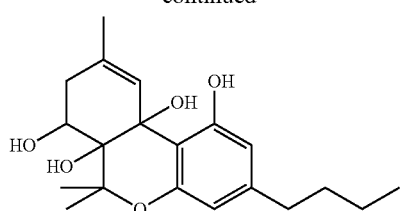

(-)-6a,7,10a-
Trihydroxy-
Δ⁹-
tetrahydrocannabinol
(-)-Cannabitetrol

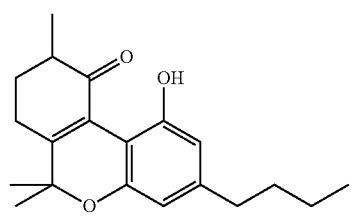

10-Oxo-Δ$^{6a(10a)}$-
tetrahydrocannabinol
OTHC

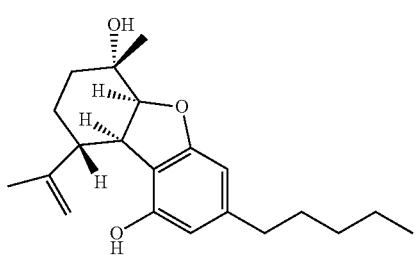

Cannabielsoin-type (CBE)

Non-limiting examples of CBE variants include:

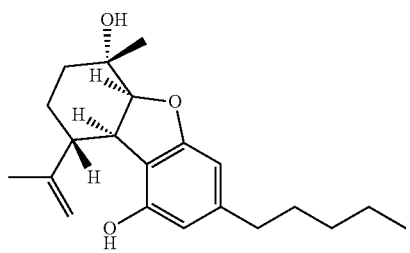

(5aS, 6S, 9R, 9aR)-Cannabielsoin
CBE-C$_5$

24
-continued

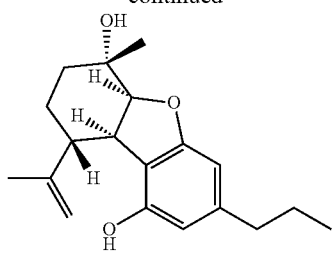

(5aS, 6S, 9R, 9aR)-C$_3$-Cannabielsoin
CBE-C$_3$

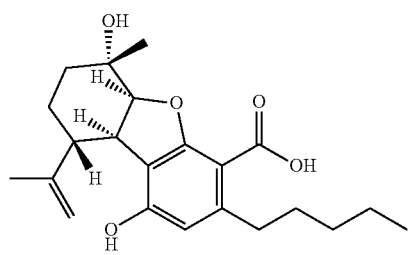

(5aS, 6S, 9R, 9aR)-Cannabielsoic acid A
CBEA-C$_5$ A

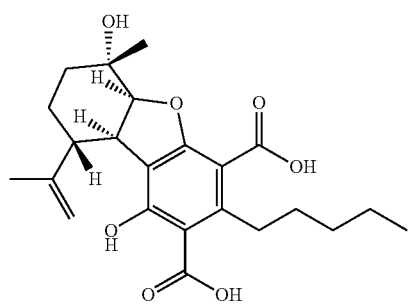

(5aS, 6S, 9R, 9aR)-Cannabielsoic acid B
CBEA-C$_5$ B

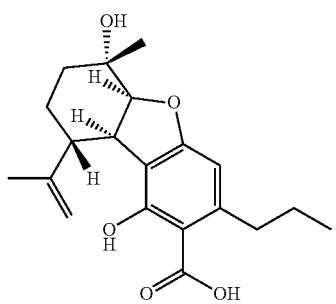

(5aS, 6S, 9R, 9aR)-C$_3$-Cannabielsoic acid B
CBEA-C$_3$ B

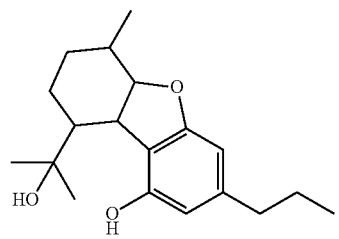

Cannabiglendol-C$_3$
OH-iso-HHCV-C$_3$

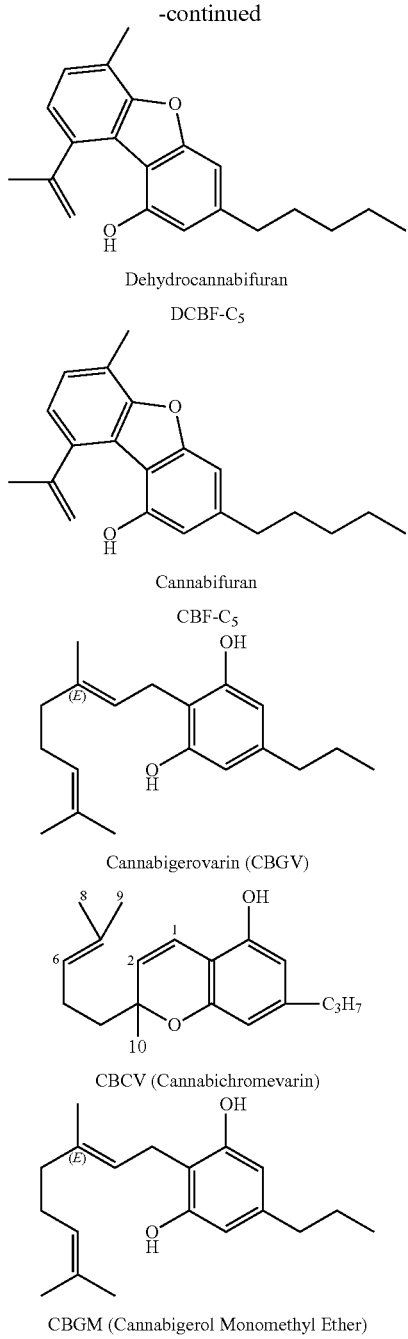

Dehydrocannabifuran
DCBF-C$_5$

Cannabifuran
CBF-C$_5$

Cannabigerovarin (CBGV)

CBCV (Cannabichromevarin)

CBGM (Cannabigerol Monomethyl Ether)

Biosynthetic pathway of cannabinoids has been studied. See Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112), each of which is herein incorporated by reference in its entirety for all purposes. According to the current model, phenolic precursors such as geranyl pyrophosphate (GPP) and polyketide, olivetolic acid (OA) are condensed by geranyl pyrophosphate olivetolate geranyltransferase (GOT) to form Cannabigerol acid (CBGA). Alternatively, GPP and divarine acid are condensed by GOT to form Cannabigerovarinic acid (CBGVA). CBGA or CBGAV is transformed to (1) CBC by CBC synthase or CBCV by CBCV synthase; (2) THC by THC synthase or THCV by THCV synthase; or (3) CBD by CBD synthase or CBDV by CBDV synthase.

More details of cannabinoids synthesis and the properties and uses of these cannabinoids are described in Russo (2011, Taming THC: potential *cannabis* synergy and phytocannabinoid-terpenoid entourage effects, *British Journal of Pharmacology*, 163:1344-1364), Russo et al. (2006, A tale of two cannabinoids: the therapeutic rationale for combining tetrahydrocannabinol and cannabidiol, *Medical Hypothesis*, 2006, 66:234-246), Celia et al. (Impact of cannabidiol on the acute memory and psychotomimetic effects of smoked *cannabis*: naturalistic study, *The British Journal of Psychiatry*, 201, 197:285-290), de Mello Schier et al., (Cannabidiol, a *Cannabis sativa* constituent, as an anxiolytic drug, *Rev. Bras. Psiquiatr*, 2012, 34(S1):5104-5117), and Zhornitsky et al. (Cannabidiol in Humans—the Quest for Therapeutic Targets, *Pharmaceuticals*, 2012, 5:529-552), each of which is herein incorporated by reference in its entirety for all purposes.

Terpenes and Terpenoids in *Cannabis* Plants

Terpenes are a large and diverse class of organic compounds, produced by a variety of plants. They are often strong smelling and thus may have had a protective function. Terpenes are derived biosynthetically from units of isoprene, which has the molecular formula $C_5H_8$. The basic molecular formulae of terpenes are multiples of that, $(C_8H_8)_n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids.

Terpenoids, a.k.a. isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in traditional herbal remedies and are under investigation for antibacterial, antineoplastic, and other pharmaceutical functions. Well-known terpenoids include citral, menthol, camphor, salvinorin A in the plant *Salvia divinorum*, and the cannabinoids found in *Cannabis*. Nonelimiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids).

*Cannabis* plants produce at over 120 different terpenes at different levels in their trichomes. Age, maturation and time of day can affect the amount and ratios of terpenes. Climate and weather also affect terpenes flavonoid production. In addition to many circulatory and muscular effects, some terpenes interact with neurological receptors. A few terpenes produced by *cannabis* plants also bind weakly to Cannabinoid receptors. Some terpenes can alter the permeability of cell membranes and allow in either more or less THC, while other terpenes can affect serotonin and dopamine chemistry as neurotransmitters.

*Cannabis* usually contains a significant amount of a terpene called beta-caryophyllene (BCP), which contributes to the aroma and flavor. Besides BCP, the terpenes produced by *cannabis* plants include, but are not limited to, borneol, caryophyllene, cineole/eucalyptol, Delta-3-carene, limonene, linalool, myrcene (e.g., β-myrcene), pinene, pulegone, sabinene, terpineol, α-pinene, β-caryophyllene, caryophyllene oxide, nerolidol, and phytol. *Cannabis* terpenes display unique therapeutic effects that may contribute meaningfully to the entourage effects of *cannabis*-based medicinal extracts. Phytocannabinoid-terpenoid interactions have been observed which can produce synergy with respect to treatment of pain, inflammation, depression, anxiety, addiction, epilepsy, cancer, fungal and bacterial infections (including methicillin-resistant *Staphylococcus aureus*), see Russo (2011, Taming THC: potential *cannabis* synergy and phytocannabinoid-terpenoid entourage effects, *British Journal of Pharmacology,* 163:1344-1364).

Geranyl pyrophosphate (GPP), which is used by *cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

*Cannabis* Plants

Contemporary illicit "recreational" marijuana cultivars have been exclusively bred and selected primarily for their THC acid content, secondarily for their terpenoid aroma and flavor chemistry, and rarely for their production of the other cannabinoid acids, such as CBDA.

CBD reduces or ameliorates some undesirable effects of THC including intoxication, sedation and tachycardia, while contributing analgesic, anti-emetic, and anti-carcinogenic properties (Russo and Guy, 2006, Medical Hypotheses (2006) 66, 234-246). Patients that have overmedicated with high-THC *cannabis* can suffer hallucinations and panic that persist for up to six hours. Subsequent to this paper, evidence has emerged that CBD may contribute anti-anxiety effects to *cannabis* varieties with THC. See "*Cannabidiol, a Cannabis sativa constituent, as an anxiolytic drug.*" (Rev Bras Psiquiatr. 2012; 34(Supl1):S104-S117) Also evidence has emerged that CBD can ameliorate the memory impairment caused by THC. See Morgan, Celia J A, et al. "Impact of cannabidiol on the acute memory and psychotomimetic effects of smoked *cannabis*: naturalistic study." *The British Journal of Psychiatry* 197.4 (2010): 285-290.

While THC can be responsible for a range of poorly tolerated side effects, it has considerable medicinal value, including mood elevation/euphoriant, analgesic, anti-emetic, anti-inflammatory/antioxidant, bronchodilatory, anti-pruritic, and anti-spasmodic effects, etc. While CBD can reduce the side effects of THC, CBD delivers a range of its own medicinal effects including neuroprotective, anti-oxidant/anti-inflammatory, anticonvulsant, anti-tumor, antibiotic against MRSA, etc. See Russo, Ethan B. "Taming THC: potential *cannabis* synergy and phytocannabinoid—terpenoid entourage effects." *British Journal of Pharmacology* 163.7 (2011): 1344-1364.

However, an ideal ratio for CBD:THC may be challenging to achieve because of the complex interactions of both drugs with various receptors. A recent review by two Canadian researchers illustrates just a few of these challenges, which states that "overall, the human data regarding CBD's potential to reverse the cognitive perturbations and psychotomimetic symptoms induced by delta-9-THC are difficult to interpret due to the possibility of a pharmacokinetic interaction between CBD and delta-9-THC (or other molecules) following oral/oromucosal administration."

When ratio of CBD/delta-9-THC is around 8.1, the CBD displays antagonistic effects. When the ration is 1.8, CBD enhanced the effects of delta-9-THC (Zuardi et al. I, Pharmacological interaction between 9-tetrahydrocannabinol and cannabidiol, two active constituents of *Cannabis sativa*. Ciênc. Cult. 1984, 36, 386-394; Zuardi et al. II, Interaction between cannabidiol (CBD) and Δ(9)-tetrahydrocannabinol (THC): Influence of administration interval and dose ratio between the cannabinoids. Psychopharmacology (Berl.) 2012, 219, 247-249). Moreover, there is evidence that combination of CBD (1-10 mg/kg IP over 21 days) with equivalent doses of delta-9-THC increased blood and brain levels of the latter, decreased levels of 11-OH-THC and THC-COOH, and augmented the anxiogenic and locomotor suppressant effects and social interaction deficits seen with delta-9-THC. (Klein et al., Cannabidiol potentiates Δ9-tetrahydrocannabinol (THC) behavioral effects and alters THC pharmacokinetics during acute and chronic treatment in adolescent rats. *Psychopharmacology* (Berl.) 2011, 218, 443-457.)

Interestingly, CBD did not change the THC-induced decrease in $CB_1$ receptor binding and none of the treatments altered 5-HT1A binding, suggesting that pharmacokinetic factors may have played a role." See Zhornitsky, Simon, and Stéphane Potvin. "Cannabidiol in Humans—The Quest for Therapeutic Targets." *Pharmaceuticals* 5.5 (2012): 529-552.

THC is produced primarily by narrow and broad-leafleted drug *cannabis* varieties. CBD is produced primarily by narrow and broad leafleted fiber *cannabis* varieties, commonly known as hemp. Where individual plants are harvested and consumed, breeding for drug *cannabis* favors selection for THC content. Where fields of drug landrace *cannabis* are cultivated solely for extraction, cultivars seem to maintain a significantly higher percentage of cannabinoids other than THC, including CBD. See Clarke, R C et al. "*Cannabis*: Evolution and Ethnobotany" University of California Press 2013 (in press).

Almost 99% of *cannabis* sold by dispensaries in California for medical purposes contains less than 1% CBD. (personal communication with SC Laboratories and Halent Laboratory, 2013). Interbreeding drug and hemp varieties of *cannabis* can produce cultivars that produce both THC and CBD, in amounts that far exceed landrace *cannabis* drug or fiber varieties. See Clarke, R C et al. "*Cannabis*: Evolution and Ethnobotany" University of California Press 2013 (in press).

Importantly to the use of medical *cannabis*, the terpenoid constituents responsible for the appealing aroma and flavor constituents found in the marijuana (i.e., illicit drug) variety parent are typically lost in these crosses. These aroma and flavor terpenoids are also synergistic with THC and CBD, modulating and enhancing the effects of cannabinoids. Myrcene content in drug *cannabis* can increase sedation. Limonene can reduce anxiety. Pinene is stimulating and enhances memory. But to-date, these terpenoid attributes have not been available in high-CBD varieties. See Russo, Ethan B. "Taming THC: potential *cannabis* synergy and phytocannabinoid-terpenoid entourage effects." *British Journal of Pharmacology* 163.7 (2011): 1344-1364.

The present invention provides medical *cannabis* plants. In some embodiments, the CBD level in dried *cannabis* plants of the present invention is higher compared to that of a dried recreational *cannabis* plants, such as the strain 'White Widow.' In some embodiments, the THC level in the dried *cannabis* plants of the present invention is lower compared to that of a dried recreational *cannabis* plants, such as the strain 'White Widow.' The *cannabis* strain 'White Widow' was developed in The Netherlands from a cross between *sativa* and indica. The strain is known for its abundance of white trichomes and high potency. 'White Widow' won the *Cannabis* Cup in 1995 and is publicly available in most Amsterdam "coffeeshops."

In some embodiments, the higher CBD levels in the *cannabis* plants of the present invention modulate some/all of one or more commonly known/perceived side effects of THC. In some embodiments, the present invention also provides medical *cannabis* plant varieties with specific ratios of CBD to THC. The reduction of THC-related adverse effects will result in a better tolerated medicine.

The present invention provides medical *cannabis* plants with specific ratios of terpenes/terpenoids to CBD and/or THC. In some embodiments, the ratio confers synergistic interactions between terpenes/terpenoids and CBD or THC. In some embodiments, the ratios of the terpenes/terpenoids, CBD and/or THC vary between varieties thereby allowing the creation of mixtures of the varieties to achieve a desired level of one or more of these constituents. In some embodiments, the terpene/terpenoid levels in the *cannabis* plants of the present invention are increased or decreased when compared to that of a control *cannabis* variety. In some embodiments, the control *cannabis* variety is an existing variety, such as a recreational marijuana plant variety. The increased terpene/terpenoid content of the varieties of the present invention will be pleasing to patients aesthetically and also modify the effects towards either sedation or stimulation.

The present invention also provides *cannabis* plants having the same organoleptic appeal as recreational marijuana plant but with the pharmacological benefit of medical *cannabis* and without the threat of overdose or adverse reactions found when using pure/high THC marijuana.

The present invention also relates to variants, mutants and trivial modifications of the seeds, plant parts and/or whole plants of the *cannabis* plants of the present invention. Variants, mutants and trivial modifications of the seeds, plants, plant parts, plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity).

The present invention also relates to a mutagenized population of the *cannabis* plants of the present invention, and methods of using such populations. In some embodiments, the mutagenized population can be used in screening for new *cannabis* lines which comprises one or more all of the morphological, physiological, biological, and/or chemical characteristics of *cannabis* plants of the present invention. In some embodiments, the new *cannabis* plants obtained from the screening process comprise one or more or all of the morphological, physiological, biological, and/or chemical characteristics of *cannabis* plants of the present invention, and one or more additional or different new morphological, physiological, biological, and/or chemical characteristic.

The mutagenized population of the present invention can be used in Targeting Induced Local Lesions in Genomes (TILLING) screening method, which combines a standard and efficient technique of mutagenesis with a chemical mutagen (e.g., Ethyl methanesulfonate (EMS)) with a sensitive DNA screening-technique that identifies single base mutations (also called point mutations) in a target gene. Detailed description on methods and compositions on TILLING® can be found in Till et al. (Discovery of induced point mutations in maize genes by TILLING, BMC Plant Biology 2004, 4:12), Weil et al., (TILLING in Grass Species, Plant Physiology January 2009 vol. 149 no. 1 158-164), Comai, L. and S. Henikoff ("TILLING: practical single-nucleotide mutation discovery." Plant J 45(4): 684-94), McCallum et al., (Nature Biotechnology, 18: 455-457, 2000), McCallum et al., (Plant Physiology, 123: 439-442, 2000), Colbert et al., (Plant Physiol. 126(2): 480-484, 2001), U.S. Pat. No. 5,994,075, U.S. Patent Application Publication No. 2004/0053236A1, and International Patent Application Publication Nos. WO 2005/055704 and WO 2005/048692, each of which is hereby incorporated by reference for all purposes.

The present invention also provides any compositions or any products made from or isolated from the plants of the present invention. In some embodiments, the compositions/products comprises extract of the plants, wherein the extract contains more than 2% CBD and less than 98% THC. In some embodiments, the extract contains higher percentage of terpenes/terpenoids compared to extract isolated from a control *cannabis* plant variety (e.g., an existing variety, such as a recreational *cannabis* plant variety).

Methods of Using *Cannabis* Plants

The present invention provides methods of using the *cannabis* plants or any parts, any compositions, or any chemicals derived from said plants of the present invention.

In some embodiments, the plants can be used for medical purpose. In some embodiments, the plants can be used by patients having a disease. In some embodiments, the diseases includes, but are not limited to, Acquired Hypothyroidism, Acute Gastritis, Agoraphobia, AIDS Related Illness, Alcohol Abuse, Alcoholism, Alopecia Areata, Alzheimer's Disease, Amphetamine Dependency, Amyloidosis, Amyotrophic Lateral Sclerosis (ALS), Angina Pectoris, Ankylosis, Anorexia, Anorexia Nervosa, Anxiety Disorders, any chronic medical symptom that limits major life activities, any Chronic Medical Symptom that Limits Major Life Activities, Arteriosclerotic Heart Disease, Arthritis, Arthritis (Rheumatoid), Arthropathy, gout, Asthma, Attention Deficit Hyperactivity Disorder (ADD/ADHD), Autism/Asperger's, Autoimmune Disease, Back Pain, Back Sprain, Bell's Palsy, Bipolar Disorder, Brain Tumor, Malignant, Bruxism, Bulimia, Cachexia, Cancer, Carpal Tunnel Syndrome, Cerebral Palsy, Cervical Disk Disease, Cervicobrachial Syndrome, Chemotherapy Chronic Fatigue Syndrome, Chronic Pain, Chronic renal failure, Cocaine Dependence, Colitis, Conjunctivitis, Constipation, Crohn's Disease, Cystic Fibrosis, Damage to Spinal Cord Nervous Tissue, Darier's Disease, Degenerative Arthritis, Degenerative Arthropathy, Delirium Tremens, Dermatomyositis, Diabetes, Diabetic Neuropathy, Diabetic Peripheral Vascular Disease, Diarrhea, Diverticulitis, Dysthymic Disorder, Eczema, Emphysema, Emphysema, Endometriosis, Epidermolysis Bullosa, Epididymitis, Epilepsy, Felty's Syndrome, Fibromyalgia, Friedreich's Ataxia, Gastritis, Genital Herpes, Glaucoma, Glioblastoma Multiforme, Graves Disease, Cluster Headaches, Migraine Headaches, Tension Headaches, Hemophilia A, Henoch-Schonlein Purpura, Hepatitis C, Hereditary Spinal Ataxia, HIV/AIDS, Hospice Patients, Huntington's Disease, Hypertension, Hypertension, Hyperventilation, Hypoglycemia, Impotence, Inflammatory autoimmune-mediated arthritis, Inflammatory Bowel Disease (IBD), Insomnia, Intermittent Explosive Disorder (IED), Intractable Pain, Intractable Vomiting, Lipomatosis, Lou Gehrig's Disease, Lyme Disease, Lymphoma, Major Depression, Malignant Melanoma, Mania, Melorheostosis, Meniere's Disease, Motion Sickness, Mucopolysaccharidosis (MPS), Multiple Sclerosis (MS), Muscle Spasms, Muscular Dystrophy, Myeloid Leukemia, Nail-Patella Syndrome, Nightmares, Obesity, Obsessive Compulsive Disorder, Opiate Dependence, Osteoarthritis, Panic Disorder, Parkinson's Disease, Peripheral Neuropathy, Peritoneal Pain, Persistent Insomnia, Porphyria, Post Polio Syndrome (PPS), Post-traumatic arthritis, Post-Traumatic Stress Disorder (PTSD), Premenstrual Syndrome (PMS), Prostatitis, Psoriasis, Pulmonary Fibrosis, Quadriplegia, Radiation Therapy, Raynaud's Disease, Reiter's Syndrome, Restless Legs Syndrome (RLS), Rheumatoid Arthritis, Rheumatoid Arthritis, Rheumatoid Arthritis, Rosacea, Schizoaffective Disorder, Schizophrenia, Scoliosis, Sedative Dependence, Seizures, Senile Dementia, Severe Nausea, Shingles (Herpes Zoster), Sinusitis, Skeletal Muscular Spasticity, Sleep Apnea, Sleep Disorders, Spasticity, Spinal Stenosis, Sturge-Weber Syndrome (SWS), Stuttering, Tardive Dyskinesia (TD), Temporomandibular joint disorder (TMJ), Tenosynovitis, Terminal Illness, Thyroiditis, Tic Douloureux, Tietze's Syndrome, Tinnitus, Tobacco Dependence, Tourette's Syndrome, Trichotillomania, Viral Hepatitis, Wasting Syndrome, Whiplash, Wittmaack-Ekbom's Syndrome, Writers' Cramp, nausea, vomiting, premenstrual syndrome, unintentional weight loss, insomnia, and lack of appetite, spasticity, painful conditions, especially neurogenic pain, movement disorders, asthma, glaucoma, adrenal disease, inflammatory bowel disease, migraines, fibromyalgia, and related conditions, multiple sclerosis, spinal cord injuries. It exhibits antispasmodic and muscle-relaxant properties as well as stimulates appetite. Other studies state that *cannabis* or cannabinoids may be useful in treating alcohol abuse, amyotrophic lateral sclerosis, collagen-induced arthritis, asthma, atherosclerosis, bipolar disorder, colorectal cancer, HIV-Associated Sensory Neuropathy, depression, dystonia, epilepsy, digestive diseases, gliomas, hepatitis C, Huntington's disease, leukemia, skin tumors, methicillin-resistant *Staphylococcus aureus* (MRSA), Parkinson's disease, pruritus, posttraumatic stress disorder (PTSD), psoriasis, sickle-cell disease, sleep apnea, and anorexia nervosa.

In some embodiments, the plants of the present invention provide one or more medical benefits to a person in need without any side effects, or with reduced side effects compared to a traditional recreational marijuana plant variety. In some embodiments, the traditional recreational marijuana plant variety is the variety 'White Widow.' In some embodiments, the traditional recreational marijuana plant variety contains at least 98%, at least 98.5%, at least 99%, at least 99.5%, at least 99.6%, at least 99.7%, at least 99.8%, at least 99.9%, or 100% THC in the cannabinoid accumulation in the plant.

In some embodiments, the plants can be used for non-medical purposes. In some embodiments, the plants are used for producing food, oil, wax, resin, rope, cloth, pulp, fiber, nutrition, construction material, plastic and composite materials, paper, jewelry, water and soil purification materials, weed control materials, cultivation materials, textiles, clothing, biodegradable plastics, body products, health food and biofuel.

In some embodiments, the plants of the present invention can be used to produce new plant varieties. In some embodiments, the plants are used to develop new, unique and superior varieties or hybrids with desired phenotypes.

In some embodiments, selection methods, e.g., molecular marker assisted selection, can be combined with breeding methods to accelerate the process. Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, Publisher: READ BOOKS, 2007, ISBN1406737062, 9781406737066), each of which is incorporated by reference in its entirety for all purposes. *Cannabis* genome has been sequenced recently (Bakel et al., The draft genome and transcriptome of *Cannabis sativa*, *Genome Biology*, 12(10):R102, 2011). Molecular makers for *cannabis* plants are described in Datwyler et al. (Genetic variation in hemp and marijuana (*Cannabis sativa* L.) according to amplified fragment length polymorphisms, *J Forensic Sci.* 2006 March; 51(2):371-5.), Pinarkara et al., (RAPD analysis of seized marijuana (*Cannabis sativa* L.) in Turkey, Electronic Journal of Biotechnology, 12(1), 2009), Hakki et al., (Inter simple sequence repeats separate efficiently hemp from marijuana (*Cannabis sativa* L.), Electronic Journal of Biotechnology, 10(4), 2007), Datwyler et al., (Genetic Variation in Hemp and Marijuana (*Cannabis sativa* L.) According to Amplified Fragment Length Polymorphisms, J Forensic Sci, March 2006, 51(2):371-375), Gilmore et al. (Isolation of microsatellite markers in *Cannabis sativa* L. (marijuana), Molecular Ecology Notes, 3(1): 105-107, March 2003), Pacifico et al., (Genetics and marker-assisted selection of chemotype in *Cannabis sativa* L.), Molecular Breeding (2006) 17:257-268), and Mendoza et al., (Genetic individualization of *Cannabis sativa* by a short tandem repeat multiplex system, Anal Bioanal Chem (2009) 393:719-726), each of which is herein incorporated by reference in its entirety for all purposes.

In some embodiments, said method comprises (i) crossing any one of the plants of the present invention comprising the expression cassette as a donor to a recipient plant line to create a F1 population; (ii) selecting offspring that have expression cassette. Optionally, the offspring can be further selected by testing the expression of the gene of interest.

In some embodiments, complete chromosomes of the donor plant are transferred. For example, the transgenic plant with the expression cassette can serve as a male or female parent in a cross pollination to produce offspring plants, wherein by receiving the transgene from the donor plant, the offspring plants have the expression cassette.

In a method for producing plants having the expression cassette, protoplast fusion can also be used for the transfer of the transgene from a donor plant to a recipient plant. Protoplast fusion is an induced or spontaneous union, such as a somatic hybridization, between two or more protoplasts (cells in which the cell walls are removed by enzymatic treatment) to produce a single bi- or multi-nucleate cell. The fused cell that may even be obtained with plant species that cannot be interbred in nature is tissue cultured into a hybrid plant exhibiting the desirable combination of traits. More specifically, a first protoplast can be obtained from a plant having the expression cassette. A second protoplast can be obtained from a second plant line, optionally from another plant species or variety, preferably from the same plant species or variety, that comprises commercially desirable characteristics, such as, but not limited to disease resistance, insect resistance, valuable grain characteristics (e.g., increased seed weight and/or seed size) etc. The protoplasts are then fused using traditional protoplast fusion procedures, which are known in the art to produce the cross.

Alternatively, embryo rescue may be employed in the transfer of the expression cassette from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

In some embodiments, the recipient plant is an elite line having one or more certain desired traits. Examples of desired traits include but are not limited to those that result in increased biomass production, production of specific chemicals, increased seed production, improved plant material quality, increased seed oil content, etc. Additional examples of desired traits includes pest resistance, vigor, development time (time to harvest), enhanced nutrient content, novel growth patterns, flavors or colors, salt, heat, drought and cold tolerance, and the like. Desired traits also include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.). The recipient plant can also be a plant with preferred chemical compositions, e.g., compositions preferred for medical use or industrial applications.

In some embodiments, molecular markers are designed and made, based on the genome of the plants of the present application. In some embodiments, the molecular markers are selected from Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety for all purposes.

The molecular markers can be used in molecular marker assisted breeding. For example, the molecular markers can be utilized to monitor the transfer of the genetic material. In some embodiments, the transferred genetic material is a gene of interest, such as genes that contribute to one or more favorable agronomic phenotypes when expressed in a plant cell, a plant part, or a plant.

Details of existing *cannabis* plants varieties and breeding methods are described in Potter et al. (2011, World Wide Weed: Global Trends in *Cannabis* Cultivation and Its Control), Holland (2010, The Pot Book: A Complete Guide to *Cannabis*, Inner Traditions/Bear & Co, ISBN1594778981, 9781594778988), Green I (2009, The *Cannabis* Grow Bible: The Definitive Guide to Growing Marijuana for Recreational and Medical Use, Green Candy Press, 2009, ISBN 1931160589, 9781931160582), Green II (2005, The *Cannabis* Breeder's Bible: The Definitive Guide to Marijuana Genetics, *Cannabis* Botany and Creating Strains for the Seed Market, Green Candy Press, 1931160279, 9781931160278), Starks (1990, Marijuana Chemistry: Genetics, Processing & Potency, ISBN 0914171399, 9780914171393), Clarke (1981, Marijuana Botany, an Advanced Study: The Propagation and Breeding of Distinctive *Cannabis*, Ronin Publishing, ISBN 091417178X, 9780914171782), Short (2004, Cultivating Exceptional *Cannabis*: An Expert Breeder Shares His Secrets, ISBN 1936807122, 9781936807123), Cervantes (2004, Marijuana Horticulture: The Indoor/Outdoor Medical Grower's Bible, Van Patten Publishing, ISBN 187882323X, 9781878823236), Franck et al. (1990, Marijuana Grower's Guide, Red Eye Press, ISBN 0929349016, 9780929349015), Grotenhermen and Russo (2002, *Cannabis* and Cannabinoids: Pharmacology, Toxicology, and Therapeutic Potential, Psychology Press, ISBN 0789015080, 9780789015082), Rosenthal (2007, The Big Book of Buds: More Marijuana Varieties from the World's Great Seed Breeders, ISBN 1936807068, 9781936807062), Clarke, R C (*Cannabis*: Evolution and Ethnobotany 2013 (In press)), King, J (Cannabible Vols 1-3, 2001-2006), and four volumes of Rosenthal's Big Book of Buds series (2001, 2004, 2007, and 2011), each of which is herein incorporated by reference in its entirety for all purposes.

Plant Transformation

Plants of the present invention can be further modified by introducing into the plants one or more transgenes which when expressed lead to desired phenotypes. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. Nos. 5,204,253, 5,015,580). A third direct method uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptll), which confers resistance to kanamycin and related antibiotics (see, for example, Messing & Vierra, *Gene* 19: 259-268 (1982); Bevan et al., *Nature* 304:184-187 (1983)). However, many different antibiotics and antibiotic resistance genes can be used for transformation purposes (refer U.S. Pat. Nos. 5,034,322, 6,174,724 and 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631(1990), U.S. Pat. Nos. 4,795,855, 5,378,824 and 6,107,549). In addition, the dhfr gene, which confers resistance to the anticancer agent methotrexate, has been used for selection (Bourouis et al., *EMBO J.* 2(7): 1099-1104 (1983).

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; and International Patent Application Publication Nos. WO/2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species. A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated herein by reference in its entirety for all purposes.

Non-limiting examples of methods for transforming *cannabis* plants and *cannabis* tissue culture methods are described in Zweger (The Biotechnology of *Cannabis sativa*, April 2009); MacKinnon (Genetic transformation of *Cannabis sativa* Linn: a multi purpose fibre crop, doctoral thesis, University of Dundee, Scotland, 2003), MacKinnon et al. (Progress towards transformation of fibre hemp, Scottish Crop Research, 2000), and US 20120311744, each of which is herein incorporated by reference in its entirety for all purposes. The transformation can be physical, chemical and/or biological.

Breeding Methods

Classical breeding methods can be included in the present invention to introduce one or more recombinant expression cassettes of the present invention into other plant varieties, or other close-related species that are compatible to be crossed with the transgenic plant of the present invention.

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The numbers of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties.

A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

This invention is further illustrated by the following examples which should not be construed as limiting. The contents of all references, patents and published patent applications cited throughout this application, as well as the Figures are incorporated herein by reference.

Example 1. Development of Classes of Cannabis Varieties

One objective of the present invention was to survey landraces of cannabis to identify and establish classes of known cannabis plants, wherein the individual plants of the present invention (i.e., cultivars, varieties, strains, races) within a given class of cannabis have certain common physiological, chemical and/or morphological characteristics. Thus, according to the present invention, cannabis plants are grouped into named classes according to their primary/dominant flavor(s) in order to establish standard cannabis classes of plants herein referred to collectively as 'Classes of Cannabis Varieties.' In some instances, class names are indicative of the landrace plant type from which they originated.

As explained in greater detail below, individual cannabis plants were identified, tested and selected within each landrace to form varieties within each cannabis class. According to the present invention, more than one variety of cannabis may have been established within a single cannabis class. As explained further herein, selected candidate cannabis plants for a specific variety may have been subjected to further breeding and selection before being chosen as a cannabis variety for a particular class. The final selected varieties were designated as Classes of Cannabis Varieties. Therefore, as used herein, 'Classes of Cannabis Varieties' or 'variety Classes' or the like each refer to certain cannabis varieties originating out of landraces, wherein they were selected based on certain desirable phenotypical characteristics and morphological characteristics for a particular class of cannabis.

The following Table 1 provides the Class color, Class name and Class abbreviations ("ABRV") for each Class of the Classes of Cannabis Varieties provided by the present invention.

TABLE 1

Cannabis class name abbreviations.

| CLASS NAME | CLASS ABRV |
|---|---|
| GOLD | GOD |
| BRONZE | BRO, HAZ |
| WHITE | WHI |
| FUSCIA | CHM |
| ORANGE | ORA |
| RED | RED |
| YELLOW | YEL |
| SILVER | SIL |
| PURPLE | PUR |
| GRAY | GRA |
| JADE | JCK, JK |
| BLUE | BLU |
| BLACK | BLA |
| GREEN | GRE |
| MISC | MI |

The following Table 2 provides the variety names for each of the Classes of Cannabis Varieties provided by the present invention.

TABLE 2

Classes of cannabis varieties

| | | | | | | | | | |
|---|---|---|---|---|---|---|---|---|---|
| GO13 | JK21 | CBD2 | HAZZ | BLA14 | BLA19 | PUR24 | MI11 | GR26 | BLA44 |
| SIL4 | JK20 | CBD4 | BLU7 | BLA15 | BLA20 | PUR25 | MI12 | GR27 | BLA45 |
| PUR3 | JK16 | CBD5 | GRE2 | BLA16 | BLA21 | PUR26 | MI13 | GR28 | BLA46 |
| YEL3 | JK14 | PUR4 | WHI4 | BLA17 | BLA22 | PUR27 | MI14 | THV1 | BLA47 |
| GRE1 | JCK5 | PUR5 | WHI5 | BLA18 | BLA23 | PUR28 | MI15 | THV1 | BLA48 |
| WHI2 | BRO4 | PUR6 | WHI5 | BLA19 | BLA24 | PUR29 | MI16 | THV1 | BLA49 |
| WHI3 | ORA3 | HAZZ | PUR30 | BLA20 | BLA25 | IS01 | MI17 | THV1 | BLA50 |
| YEL4 | ORA2 | BLU7 | GRE30 | BLA21 | BLA26 | IS02 | MI18 | THV1 | BLA51 |
| GRA3 | BRO5 | GRE2 | WHI6 | BLA22 | BLA27 | IS03 | MI19 | THV1 | BLA52 |
| RED2 | SIL2 | WHI4 | GRE31 | BLA23 | BLA28 | IS04 | MI20 | THV1 | BLA44 |
| CBD3 | BLU1 | WHI5 | HAZ5 | BLA24 | BLA29 | IS05 | GR03 | THV1 | BLA45 |
| BLA1 | BLU2 | WHI5 | HAZ6 | BLA25 | BLA30 | IS06 | GR04 | THV1 | BLA46 |
| WHI7 | SIL3 | PUR30 | HAZ7 | BLA26 | BLA31 | IS07 | GR05 | THV1 | BLA47 |
| GOD1 | BLU3 | GRE30 | HAZ8 | BLA27 | BLA32 | IS08 | GR06 | THV1 | BLA48 |
| GOD2 | HAZ3 | WHI6 | GO14 | BLA28 | BLA33 | IS09 | GR07 | THV2 | BLA49 |
| GOD3 | HAZ2 | GRE31 | BLU8 | BLA29 | BLA34 | IS10 | GR08 | THV2 | BLA50 |
| GOD4 | ORA4 | HAZ5 | BLU9 | BLA30 | PUR7 | IS11 | GR09 | THV2 | BLA51 |
| GOD5 | GRA2 | HAZ6 | BLU10 | BLA31 | PUR8 | IS12 | GR10 | THV2 | BLA52 |
| BRO1 | CBD1 | HAZ7 | BLU11 | BLA32 | PUR9 | IS13 | GR11 | THV2 | |
| WHI1 | HAZ4 | HAZ8 | BLU12 | BLA33 | PUR10 | IS14 | GR12 | THV2 | |
| CHM1 | GOD6 | GO14 | BLU13 | BLA34 | PUR11 | IS15 | GR13 | THV2 | |
| ORA1 | GOD7 | BLU8 | BLA2 | PUR7 | PUR12 | IS16 | GR14 | THV2 | |
| CHM2 | GOD8 | BLU9 | BLA3 | PUR8 | PUR13 | IS17 | GR15 | THV2 | |
| RED1 | GOD9 | BLU10 | BLA4 | PUR9 | PUR14 | MI01 | GR16 | THV2 | |
| YEL1 | GO10 | BLU11 | BLA5 | PUR10 | PUR15 | MI02 | GR17 | BLA35 | |
| SIL1 | GO11 | BLU12 | BLA6 | PUR11 | PUR16 | MI03 | GR18 | BLA36 | |
| PUR1 | YEL2 | BLU13 | BLA7 | PUR12 | PUR17 | MI04 | GR19 | BLA37 | |
| GRA1 | CHM3 | CBD2 | BLA8 | PUR13 | PUR18 | MI05 | GR20 | BLA38 | |
| JCK4 | GO12 | CBD4 | BLA9 | PUR14 | PUR19 | MI06 | GR21 | BLA39 | |
| JCK8 | PUR2 | CBD5 | BLA10 | PUR15 | PUR20 | MI07 | GR22 | BLA40 | |
| JCK7 | BLU4 | PUR4 | BLA11 | PUR16 | PUR21 | MI08 | GR23 | BLA41 | |
| JK12 | BLU5 | PUR5 | BLA12 | BLA17 | PUR22 | MI09 | GR24 | BLA42 | |
| JK11 | BLU6 | PUR6 | BLA13 | BLA18 | PUR23 | MI10 | GR25 | BLA43 | |

The following Table 3 provides the predominant flavors of each Class of Classes of *Cannabis* Varieties according to the present invention.

TABLE 3

Cannabis class predominant flavors

| Class | Class Flavor |
|---|---|
| GOLD | Lemon/Pine |
| SILVER | Sandalwood/Coffee/Spice |
| BRONZE | Hash/Spice/Haze |
| PURPLE | Grape/Pine |
| BLUE | Blueberry/Pine |
| GREEN | Sweet Citrus/Cream/Skunk |
| RED | Cherry/Sweet |
| ORANGE | Mandarin/Orange/Lemon |
| YELLOW | Spruce/Spice/Pine |
| WHITE | Vanilla |
| GRAY | Generic Sweet Amsterdam |
| BLACK | Anise/Black Licorice |
| JACK | Sweet Myrcene/Pine |
| FUSHIA | Cherry |
| MISC | Various |

More detailed descriptions of the development and characteristics of the Classes of *Cannabis* Varieties of the present invention are provided below, including for the following plant traits:

Sugar Leaf—leaves surrounding buds (inflorescences) and that are covered with glandular trichomes.

Top of Top—apical most inflorescence body (very tip top of plant).

Low of Top—lowest auxiliary bud that is part of apical most inflorescence (bottom bud of tip top of plant).

Top Mix—ground up entire top bud (usually top 6" of plant).

Low Mix—ground up lower buds (under top canopy).

Standard Mix—ground-up combination of lowest, middle and top buds in order to determine an overall average for plant chemotype.

Max THC Wt. %—total possible amount of delta9-THC that can result from the combustion of THCA (about 70% conversions at best). For a detailed explanation of the methodology to determine Max THC Wt. % see Dussy et al. (2005) Isolation of $\Delta^9$-THCA-A from hemp and analytical aspects concerning the determination of $\Delta^9$-THC in *cannabis* products, Forensic Science International 149:3-10.

As shown further herein, the Classes of *Cannabis* Varieties of the present invention are used for medical purposes as is or are used in breeding schemes to develop new *cannabis* varieties within, between or among the various classes of Classes of *Cannabis* Varieties.

GO13

Description of Breeding Stock.

Inflorescences were obtained for a land race of Gold class varieties and seeds from these inflorescences were isolated and put into conditions proper for their germination. The seeds which germinated grew identically. However, upon flower onset, the seedlings were selected for the strongest limonene/Pine-Sol fragrance and narrowed to two phenotypes. Of these, the individual phenotype with the best user experience based on testing was selected to create GO13, a variety classified into the Gold Class.

Hypothesized Genetics.

*Cannabis indica* ssp. *afghanica* WLD "Purple Afghan" x *C. indica* ssp. indica var. indochinensis NLD "Lemon Thai" x *C. indica* ssp. kafiristanica NLDA.

Propagation and Vegetative Growth.

Cuttings from GO13 are marked by 3-finger leaflet sets with internode buds asymmetrically located on alternate sides on main shoot. In particular, the internode space of this variety tends to be greater than that of other gold class varieties and stems harden quicker. Roots nodes appear with 7-10 days and roots within 10-14 days. The GO13 grows extremely tall and thin with extreme stretching and asymmetrical bud and leaf sets. When root system is not limited or pruned, this variety of gold class varieties exhibits unparalleled vigor and stretch. Vegetative growth is marked by a deep blue-green (Munsell ID) hue with lime green thin stalks. Petioles are marked by purple pointillism increasing on sides exposed to light and the end closest to palm of the leaflet set. Root bodies are typically full and bright white. Stalks radiate a pungent smell of body odor or urine. Canopy extremely sparse and apical dominance can be disrupted easily with removal of apical meristem. Main stems also exhibit purpling, but inflorescences are not purple.

Onset of Flowering and Inflorescences.

Leaves are 3 and 5 leaflet patterns with 3 being predominant and overall decreasing to 1 and to none in the presence of female flowers.

Female flowers are spread out due to the large internode spacing. Upon flower set, buds and supporting structures (stems, leaves, etc.) are quickly covered with an extremely dense field of trichome bodies. Again, this variety tends to be more densely covered with trichome bodies than its parent and other gold class varieties. In fact, the inflorescences are very dense and have large calyxes covered in highly resinous glands that exhibit this variety's distinct lemon Pine-Sol scent after only 7-10 days. As inflorescences mature, the density compact sets give way to foxtailing and 'reaching' by individual calyxes, resulting in an overall increase in surface area dedicated to trichome production. In particular, the oily character of these flowers set this gold class apart from its parent and other gold class varieties. Textures are extremely sticky and fibrous. Stems do not 'break' they tear, but remain attached via intense fiber strands.

Description of Finished Flower.

GO13 consistently produces among the highest THCA levels of medical *cannabis* known in California and is often noted for an intense and crushing physical effect combined with a sublime and inspiring mental flight. Aromas of lemon peel, NASCAR, and Pine-Sol combine to produce a pure menthol exhalation when smoked. Noted for excellent appetite and sexual stimulation often accompanied by uninterrupted sleep.

Chemotype Description for Patient.

Relative potency: very strong. Headspace Terpenes: pinenes, myrcene, limonene, and linalool. Caryophyllene content: high.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days). Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying.

Yield Data.

Yield determined on a 'per plant' basis and determined by specified cultivation techniques employed. In this case, indoor Controlled Environment Agriculture (CEA) technique following the protocol described elsewhere herein. Flower onset was initiated with 12/12 day/night at approximately 12" in vegetative height. Total biomass ~150 g, finished flowers ~50 g, and/or ~50 g of seed per plant.

Potential Uses of this Line.

Potential uses of GO13 include but are not limited to medical applications, as a source for extractions of plant constituents and chemicals, for commercial raw materials, fiber and pulp.

Patient Testimonials/Comments and Visual Observations.

Patients rave about the flavor and 'oily' composition by comparison to other Gold class varieties. In fact, besides the extremely high potency from its combined cannabinoid/terpenoid 'entourage effects", this line of gold class has been noted by patients for being particularly effective for sexual and appetite stimulation.

Palatable CBDA varieties with ideal CBDA:THCA ratio can be developed from GO13 to reduce side-effects associated with extant recreational *cannabis* varieties related to GO13. Additionally reduced THCA varieties can be developed that are intended to reduce side-effects from extant recreational *cannabis* varieties related to GO13.

Flavor when smoked included distinct citrus and mentholated notes. Significant analgesia accompanies its deep range of effects, but with little sedation, but the "rising/falling" physical sensations associated with gold class. Some patients have compared its flavor to bergamot orange. Patients also remark on the "clarity" of this variety's psychoactivity, with less sedation and disorientation, and with considerable euphoria.

Its aroma has been characterized as a tangy, sharp, naphthalene aroma with orange notes and a sweet undertone. Also the range of pharmacologically active terpenoids that this variety produces provide a significant "entourage effect" that accompanies the effects of its THC content. While it stimulates appetite, it does not appear to encourage overeating.

Chemical Analysis.

Low MW Terpene Analysis (136). Sesquiterpene Analysis (204). Cannabinoid Analysis (>284).

Mass spectrometry data, chromatography data, and statistical data related to the chemical analysis are shown in the following Tables 4-6.

TABLE 4

Chemical analysis of plant samples for GO13.

| Plant Location | THC wt. % Ave | Max | THCA wt. % | CBD wt. % Ave | Max | CBDA wt. % | CBN wt. % | THC/CBD Ratio | Chromo ID |
|---|---|---|---|---|---|---|---|---|---|
| Sample #: see Chromo ID numbers in last column. | | | | | | | | | |
| Sugar leaf | 0.5 | 4.1 | 6.0 | 0.1 | 0.1 | 0.0 | 0.1 | 41 | VRC-007 |
| Top of top | 0.5 | 9.6 | 14.7 | 0.2 | 0.2 | 0.1 | 0.2 | 48 | VRC-008 |
| Low of top | 0.9 | 11.3 | 16.9 | 0.1 | 0.2 | 0.1 | 0.2 | 56.5 | VRC-009 |
| Top mix | 0.7 | 11.2 | 17.0 | 0.2 | 0.2 | 0.1 | 0.3 | 56 | VRC-17 |
| Standard mix | 1.0 | 11.3 | 16.8 | 0.2 | 0.2 | 0.1 | 0.2 | 56.5 | VRC-18 |
| Sample #: AS623 | | | | | | | | | |
| Standard mix | 0.8 | 11.3 | 16.8 | 0.2 | 0.2 | 0.1 | 0.1 | 56.5 | |
| Sample #: A8623 | | | | | | | | | |
| Standard Mix | 0.75 | 15.51 | 16.81 | 0.18 | 0.25 | 0.08 | ND | 61.07 | |

THC/CBD Ratio = Maximum THC wt %/Maximum CBD wt %.
Chromo ID = Chromatogram identification number for quantification of cannabinoids.
ND = Not determined.

TABLE 5

Chemical analysis of flower samples for GO13 for Sample #: 2876-7.1.

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.73 | ND | 18.55 | <0.1 | ND | <0.1 | <0.1 |
| Total content for unheated flower sample, mg/g | | | | | | |
| 7.3 | ND | 185.5 | <0.1 | ND | 0.6 | 0.1 |
| Estimated total content for ideally heated flower sample, % by wt. | | | | | | |
| ND | 12.1 | ND | ND | <0.1 | ND | <0.1 |

ND = Not determined.

Note:

Most of the acid cannabinoids (e.g., THCA) readily converts to their neutrals (THC) upon heating, giving different properties.

TABLE 6

The cannabinoid and terpene profiles, unheated, % by wt, or terpene content by retention time for Sample #: 2876-7.1

| Cannabinoid Profile % by wt | | Terpenoid Profile % by wt | | Terpene content by retention time | |
|---|---|---|---|---|---|
| THCA | 18.55 | terpinolene | 0.11 | 5.91 | alpha-pinene |
| Δ⁹-THC | 0.73 | myrcene | 0.86 | 6.4 | camphene |
| Δ⁸-THC | <0.03 | Limonene | <0.01 | 7.35 | beta-pinene |
| THCA-C4 | 0.04 | Linalool | 0.18 | 7.91 | myrcene |
| THCVA | 0.12 | Caryophyllene Oxide | <0.01 | 9.53 | carpenes/terpins |
| THCV | <0.03 | Beta-Caryophyllene | 0.31 | 9.34 | alpha-limonene |
| CBDA | 0.06 | Phytol | <0.01 | 10.15 | ocimene |
| CBD | <0.03 | alpha-pinene | 0.07 | 11.66 | terpinolene |
| CBCA | 0.03 | | | 12.39 | linalool |
| CBC | <0.03 | | | 16.41 | terpineol |
| CBGA | 0.32 | | | 22-30 | sesquiterpenes/caryophyllenes |
| CBG | 0.43 | | | | |
| CBLA | 0.10 | | | | |
| CBNA | <0.03 | | | | |
| CBN | <0.03 | | | | |

BRO5

Description of Breeding Stock.

Inflorescences were obtained for a landrace of Haze and seeds from these inflorescences were isolated and put into conditions proper for their germination.

The seeds which germinated grew identically, being short and squatty with purple leaves and 'sweet' scent, with one exception which was tall and stretchy with a savory and musty scent. There was absolutely no sweetness in the smell of BRO5. Testing proved that its effects were the most enjoyable and virtually mycrene free. The lack of mycrene and presence of pinene and limonene is quite rare and sets this variety apart from most *cannabis* varieties.

Upon flower onset, the seedlings were selected for being short and squatty with purple leaves and 'berry' scent to create BRO5, a variety classified into the Gold Class.

Hypothesized Genetics.

"NL#5×Haze×inbred Thai"

Propagation and Vegetative Growth.

Cuttings from BRO5 are marked by 9-finger very thin leaflet sets with internode buds asymmetrically located on alternate sides on main shoot. In particular, the internode space of this variety tends to be extremely large. Stems are tall, frail and stretchy. Cuttings roots appear within 10-14 days. The BRO5 grows tall and stretchy with flimsy stems. It possesses the classic narrow-leafleted morphology associated with 1970's Haze cultivars that were inherited from Haze's tropical drug *cannabis* parents, including Colombian and Thai varieties.

BRO5 grows with asymmetrical bud and leaf sets. Vegetative growth is marked by a lightened green (Munsell ID) hue with lime green thin stalks. Leaflets are longer and narrower than most of drug *cannabis* varieties.

BRO5 displays vigorous hybrid character.

There is little or no purple on this plant until the final weeks of flowering. Leaves turn deep purple with flowers silvering up as time goes on. Stalks radiate a 'hazy' or musty urine scent. Canopy extremely sparse and topping near flowering is encouraged for even growth.

Onset of Flowering and Inflorescences.

Leaves are 9 and 7 leaflet patterns with 7 being predominant and overall decreasing to 1 and to none in the presence of female flowers. In particular, flower onset is very slow with this variety. 'Hairy' flowers are not very dense. Female flowers are spread apart due to the large internode spacing.

Upon flower set, buds and supporting structures (stems, leaves, etc.) take longer than most to become covered with trichome bodies. Everything about this plant takes longer. As inflorescences mature, they become more hardened and dense. In particular, the oily character of these flowers was the driving force for selection.

Description of Finished Flower.

BRO5 defines heady, hazy medicine with highly functional mental effects. This variety has the structure and scent of the BRO5 lines famous around the world. With aromas of spice and anise, the hashish flavor when smoked is enlightening.

BRO5 is noted for mood elevation, inspiration and creativity and is also likely to improve home hygiene.

Chemotype Description for Patient.

Relative potency: strong. Headspace Terpenes: pinenes, limonene. Caryophyllene content: high.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield determined on a 'per plant' basis and determined by specified cultivation techniques employed. In this case, indoor CEA technique following the protocol described elsewhere herein. Flower onset was initiated with 12/12 day/night at approximately 16" in vegetative height. Organic mix of soil in fabric pots, a regimen of nutrients following standard NPK feeding schedules and addition of proprietary mixture. Flower onset was initiated with 12/12 day/night when plant reached approximately 16" in vegetative height..

Potential Uses of this Line.

Potential uses of BRO5 include but are not limited to medical applications, extractions, commercial raw material (chemical), fiber and pulp.

Patient Testimonials/Comments and Visual Observations.

Patients rave about the great experience of using BRO5. The effects are mind stimulating with some visual 'crispness'. The patients often comment that this variety is good for the 'new' user because of its lower THC concentration and the 'clarity' of the experience.

Chemical Analysis.

Low MW Terpene Analysis (136). Sesquiterpene Analysis (204). Cannabinoid Analysis (>284).

WHI2

Description of Breeding Stock.

Inflorescences were obtained for a proprietary breeding program and seeds from these inflorescences were isolated and put into conditions proper for their germination. The seeds which germinated grew identically. The resulting plants were then crossed with GO13 plants and seeds were planted and germinated for selection based on oil content of the plants. Plants with higher oil content were selected to create WHI2.

Hypothesized Genetics.

"*Cannabis* indica ssp. *afghanica* WLD "SB Purple" x *C. indica* ssp. indica NLD x *C. indica* ssp. kafiristanicaNLDA"

Propagation and Vegetative Growth.

Cuttings from WHI2 are marked by 5-finger leaflet sets with internode buds asymmetrically located on alternate sides on main shoot. In particular, the internode space of this variety tends to be longer and stalks thinner (~4-8" veg, decreasing flower onset). Plants are tall, stretchy and productive. Roots of the cuttings appear within 10-14 days.

The WHI2 grows tall and stretchy and exhibits little or no apical dominance.

WHI2 grows with asymmetrical bud and leaf sets. Vegetative growth is marked by a lavish green (Munsell ID) hue with green undersides and hard wood like stalks. When healthy, fan leaves are extremely jagged and serrations are very pronounced.

The stems are strong and fibrous, but extremely thin. The standout quality of WHI2 is the amount of trichomes and their density. The flower sets look 'frosty' before most other varieties.

Stalks are vanilla spice scent.

Canopy is extremely sparse with clustered bud formation. Topping extremely encouraged.

Onset of Flowering and Inflorescences.

Leaves are 5 leaflet patterns with 5 being predominant and overall decreasing to 1 and to none in the presence of female flowers. In particular, flower onset is fast by comparison to most varieties.

Trichome density and smell are almost immediate. Female flowers are spear-shaped, dense and thick although relatively large internode lengths. Again, this variety tends to be more densely covered with trichome bodies than most other varieties.

The flowers are compact and well-formed in the shape of small pinecones. As inflorescences mature, the density compact sets compound to form bright orange and silver flowers that give way to yellow and purple sun leaves.

Plants are marked by unusually high oil mass content and extremely dense small resinous buds.

Apical inflorescences are often smaller than lowers. Inflorescences particularly are resistant to fungal infestation due to compact oil flowers.

Description of Finished Flower.

WHI2 (a.k.a., internally known as 'Heiress' or "Oily Heiress) was bred from a dream team of medical *cannabis* genetics: Northern Lights x Haze, Santa Barbara Purps, a Midwest G-13 and the aforementioned GO13. The chemotype of this variety is indicative of this diverse genetic heritage. The aroma consists of vanilla, grapefruit, and even has petroleum notes, but a rich creamy vanilla flavor emerges when smoked. Noted for its rare combination of clarity and profound potency, it delivers functional and long lasting inspiration and positivity.

Chemotype Description for Patient.

Relative potency: very strong. Headspace Terpenes: pinenes, myrcene, limonene, ocimene, linalool, terpineol. Caryophyllene content: very high Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that one is actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~120 g, finished flowers ~40 g, and/or ~30 g of seed per plant.

Potential Uses of this Line.

Potential uses of WHI2 include but are not limited to medical applications, extractions, commercial raw material (e.g., chemical), fiber and pulp.

Patient Testimonials/Comments and Visual Observations.

Very interesting from an organoleptic standpoint (sweet Amsterdam flavor) and a caryophyllene content standpoint. WHI2 produces a happy laughing high, with the classic combusted aroma of 1990's landrace varieties of the same *cannabis* class.

Chemical Analysis.

Low MW Terpene Analysis (136). Sesquiterpene Analysis (204). Cannabinoid Analysis (>284). Chemical analysis for WHI2 plants is summarized in Tables 7 and 8.

TABLE 7

Chemical analysis of flower samples for WHI2 for Sample # 2785-6:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.45 | ND | 18.97 | <0.1 | ND | <0.1 | <0.1 |
| Total content for unheated flower sample, mg/g | | | | | | |
| 4.5 | ND | 189.7 | <0.1 | ND | 0.7 | 0.1 |

TABLE 7-continued

Chemical analysis of flower samples for WHI2 for Sample # 2785-6:

| THC | | | CBD | | | CBN |
|---|---|---|---|---|---|---|
| Average | Maximum | THCA | Average | Maximum | CBDA | Maximum |
| Estimated total content for ideally heated flower sample, % by wt. | | | | | | |
| ND | 12.1 | ND | ND | <0.1 | ND | <0.1 |

ND = Not determined.
Note:
Most of the acid cannabinoids (e.g., THCA) readily converts to their neutrals (THC) upon heating, giving different properties.

TABLE 8

The cannabinoid and terpene profiles, unheated, % by wt for Sample #: 2785-6

| Cannabinoid Profile % by wt | | Terpenoid Profile % by wt | |
|---|---|---|---|
| THCA | 18.97 | Terpinolene | 0.02 |
| $\Delta^9$-THC | 0.45 | Myrcene | <0.01 |
| $\Delta^8$-THC | <0.03 | Limonene | <0.01 |
| THCA-C4 | 0.04 | Linalool | 0.30 |
| THCVA | 0.08 | Caryophyllene Oxide | <0.01 |
| THCV | <0.03 | Beta-Caryophyllene | 0.44 |
| CBDA | 0.07 | Phytol | <0.01 |
| CBD | <0.03 | alpha-pinene | 0.16 |
| CBCA | 0.07 | | |
| CBC | <0.03 | | |
| CBGA | 0.39 | | |
| CBG | 0.21 | | |
| CBLA | <0.03 | | |
| CBNA | <0.03 | | |
| CBN | <0.03 | | |

SIL4

Description of Breeding Stock.

Inflorescences were obtained for a landrace of SIL4 and seeds from these inflorescences were isolated and put into conditions proper for their germination. The seeds which germinated grew fairly similarly. However, upon flower onset, the seedlings were selected for trichome density, leaflet width and root vigor to create SIL4.

Hypothesized Genetics.

"*Cannabis* indica ssp. *afghanica* WLD"

Propagation and Vegetative Growth.

Cuttings from SIL4 are marked by 7-finger leaflet sets with internode buds asymmetrically located on alternate sides on main shoot. In particular, the internode space of this variety tends to be greater than that of other Silver varieties and stems harden more slowly. In particular, the cutting roots more rapidly than other Silver varieties. In fact, the root bodies of the plant are the most robust and vigorous of all *cannabis* plants tested in our laboratory. Root time varies with nodes appearing within 7-10 days and roots within 10-14 days.

The SIL4 grows medium in stature with stocky branches and stalks. Even growth throughout with asymmetrical bud and leaf sets. Vegetative growth is marked by a deep blue-green (Munsell ID) hue with lime green thin stalks. Leaflets are fat and exhibit classic recreational 'indica' look. These broad leaflets are indicative of this variety. Petioles are marked by purple pointillism increasing on sides exposed to light and the end closest to palm of the leaflet set. Root bodies are typically full and bright white. Stalks radiate a pungent smell of bubble gum coffee and green class. Canopy extremely sparse and apical dominance can be clearly observed and removal of apical meristem often results in stunted growth. Main stems may also exhibit purpling, and inflorescences sets are large, but spread out.

Onset of Flowering and Inflorescences.

Leaves are 7 and 5 leaflet patterns with 3 being predominant and overall decreasing to 1 and to none in the presence of female flowers. Female flowers are spread out due to the large internode spacing.

Upon flower set, buds and supporting structures (stems, leaves, etc.) are quickly covered with an extremely dense field of trichome bodies. Again, this variety tends to be more densely covered with trichome bodies than its parent and other Silver varieties. In fact, the inflorescences are very dense and have large calyxes covered in highly resinous glands that exhibit this variety's distinct lemon Pine-Sol scent after only 7-10 days.

As inflorescences mature, the dense and compact calyx clusters or flower sets give way to foxtailing and 'reaching' by individual calyxes, resulting in an overall increase in surface area dedicated to trichome production. In particular, the oily character of these flowers set SIL4 apart from its parent and other Silver varieties. Textures are extremely sticky and fibrous. Stems do not 'break' they tear, but remain attached via intense fiber strands.

Description of Finished Flower.

SIL4 has descended from the great Afghan hashish *cannabis* cultivars and is a nearly perfect choice for vaporization. The resin content delivers a range of tastes and effects with each draw.

The aroma consists of coffee, spice and exotic incense. This variety is noted for its ability to mellow without sedation or fatigue, excellent analgesic effects and deep introspection.

Chemotype Description for Patient.

Relative potency: mild. Headspace Terpenes: pinenes, myrcene, limonene, linalool. Caryophyllene content: medium Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not the 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein.

Flower onset was initiated with 12/12 day/night at approximately 12" in vegetative height. Total biomass ~120 g, finished flowers ~30 g, and/or ~15 g of seed per plant.

Potential Uses of this Line.

Potential uses of SIL4 include but are not limited to medical applications, extractions, commercial raw material (e.g., chemical), fiber and pulp.

Patient Testimonials/Comments and Visual Observations.

Patients rave about the coffee flavor and 'oily' and 'silver' composition of SIL4. In fact, besides the mellow effects, SIL4 is particularly noted for treating pain and inspiration.

Chemical Analysis.

Low MW Terpene Analysis (136). Sesquiterpene Analysis (204). Cannabinoid Analysis (>284). Chemical analysis for SIL4 plants is summarized in Tables 9 and 10.

TABLE 9

Chemical analysis of flower samples for SIL4 for Sample # 2651-3:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.35 | ND | 17.42 | <0.1 | ND | <0.1 | <0.1 |
| Total content for unheated flower sample, mg/g | | | | | | |
| 3.5 | ND | 174.2 | <0.1 | ND | 0.8 | 0.1 |
| Estimated total content for ideally heated flower sample, % by wt. | | | | | | |
| ND | 11.0 | ND | ND | <0.1 | ND | <0.1 |

ND = Not determined.
Note:
Most of the acid cannabinoids (e.g., THCA) readily converts to their neutrals (THC) upon heating, giving different properties.

TABLE 10

The cannabinoid and terpene profiles, unheated, % by wt for Sample #: 2651-3

| Cannabinoid Profile % by wt | | Terpenoid Profile % by wt | |
|---|---|---|---|
| THCA | 17.42 | terpinolene | 0.07 |
| $\Delta^9$-THC | 0.35 | myrcene | <0.01 |
| $\Delta^8$-THC | <0.03 | Limonene | <0.01 |
| THCA-C4 | 0.04 | Linalool | 0.19 |
| THCVA | 0.09 | Caryophyllene Oxide | <0.01 |
| THCV | <0.03 | Beta-Caryophyllene | 0.25 |
| CBDA | 0.08 | Phytol | <0.01 |
| CBD | <0.03 | alpha-pinene | 0.01 |
| CBCA | 0.06 | | |
| CBC | <0.03 | | |
| CBGA | 0.31 | | |
| CBG | 0.06 | | |
| CBLA | <0.07 | | |
| CBNA | <0.03 | | |
| CBN | <0.03 | | |

BLU8

Description of Breeding Stock.

Inflorescences were obtained from a DJ Short's Flo (a.k.a. DJ's Flo) pollinated by a hermaphroditic Hawaiian plant and seeds from these inflorescences were isolated and put into conditions proper for their germination.

The seeds which germinated grew very uniformly in appearance. However, the seedlings were selected for vigorous phenotype with highest trichome density and 'oily' feel of resin glands to create BLU8.

Hypothesized Genetics.

"1995 Hawaiian Bag Seed x Thai".

Propagation and Vegetative Growth.

Cuttings from BLU8 are marked by 7-finger leaflet sets with internode buds asymmetrically located on alternate sides on main shoot. In particular, the internode space of this variety tends to be medium-stretchy (~4" veg, decreasing flower onset). Plants are tall, robust and lanky. Cuttings root within 10-14 days.

The BLU8 grows tall and stout with mixed apical dominance.

BLU8 grows with asymmetrical bud and leaf sets. Vegetative growth is marked by a deeper off green (Munsell ID) hue with deep purple strong hollow stalks.

When healthy, sun leaves are gigantic with magenta and purple under side coloring. Plants have super vigor and hybrid character. BLU8's stand-out quality feature is the high amount of trichomes and the high amount of oil. Stalks have a pungent 'medical' scent.

Plant canopy is dense with large cola formation. Topping encouraged.

Onset of Flowering and Inflorescences.

Leaves are 7 leaflet patterns with 7 being predominant and overall decreasing to 1 and to none in the presence of female flowers. In particular, flower onset is medium-fast by comparison to most varieties. Trichome density and smell are almost immediate. Female flowers are clustered to do decreased internode spacing. Again, this variety tends to be more densely covered with trichome bodies than its parents and other varieties. In fact, the inflorescences are very dense and have large calyxes covered in highly resinous glands that exhibit this variety's distinct blueberry pine medicine/medicinal scent after only 7-10 days.

As inflorescences mature, the density compact sets compound to form bright green and extremely oily buds. In particular, the oily character of these flowers set this its parent and phenotypes.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins.

The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Potential Uses of this Line.

Potential uses of BLU8 include but are not limited to medical applications, extractions, commercial raw material (e.g., chemical), fiber and pulp.

Patient Testimonials/Comments and Visual Observations.

BLU8 is very interesting from an organoleptic standpoint and it is unique in almost all visual categories.

Chemical Analysis.

Low MW Terpene Analysis (136). Sesquiterpene Analysis (204). Cannabinoid Analysis (>284).

RED2

Description of Breeding Stock.

Inflorescences were obtained from a random mislabeled dispensary clone, and selfed seeds from these plants were germinated. The seeds which germinated grew very similarly. The resulting seedlings were selected for vigor.

Hypothesized Genetics.

"Cannabis indica ssp. afghanica WLD "Cherry Afghan" x C. indica ssp. indica NLD hybrid Propagation and Vegetative Growth.

Cuttings from RED2 are marked by 7-finger leaflet sets with internode buds asymmetrically located on alternate sides on main shoot. In particular, the internode space of this variety tends to be medium-stretchy (~4" veg, decreasing flower onset). The plants are tall, robust and lanky. Cuttings root within 10-14 days.

The RED2 grows tall and strong with little apical dominance. RED2 grows with asymmetrical bud and leaf sets.

Vegetative growth is marked by a lighter shade of green (Munsell ID) hue with deep purple strong hollow stalks. When healthy, sun leaves are point upward toward light source.

The stems are strong and fibrous. The plants are super vigorous and hybrid in character. The stand-out quality is the high amount of trichomes and the high amount of oil. Stalks have a sweet scent. Canopy is dense with large cola formation. Topping encouraged.

Onset of Flowering and Inflorescences.

Leaves are 7 leaflet patterns with 7 being predominant and overall decreasing to 1 and to none in the presence of female flowers. In particular, flower onset is medium-fast by comparison to most varieties.

Trichome density and smell are almost immediate. Female flowers are clustered to do decreased internode spacing. Again, this variety tends to be more densely covered with trichome bodies than its parents and other varieties. In fact, the inflorescences are very dense and have large calyxes covered in highly resinous glands that exhibit this variety's distinct blueberry pine medicine/medicinal scent after only 7-10 days.

As inflorescences mature, the dense and compact calyx clusters or flower sets form bright green and extremely oily buds. In particular, the oily character of these flowers set this variety apart from its parent and phenotypes.

Description of Finished Flower.

RED2 combines a beautifully sweet cherry WLD Afghan with a NLD to deliver a strong, cheerful, dreamy psychoactivity. This variety produces a pleasant silliness and a 'where'd I put my keys!?' memory effect and obliterates most patient troubles.

Aroma consists of cherry cough drops, fresh strawberries and just a hint of spice. RED2 is often noted for long-lasting effects and positive mood impact.

Chemotype Description for Patient.

Relative potency: strong. Headspace Terpenes: pinenes, myrcene, limonene, and linalool. Caryophyllene content: high Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~180 g, finished flowers ~60 g, and/or ~50 g of seed per plant.

Potential Uses of this Line.

Potential uses of RED2 include but are not limited to medical applications, extractions, commercial raw material (e.g., chemical), fiber and pulp.

Patient Testimonials/Comments and Visual Observations.

Noted as being very interesting from an organoleptic standpoint. RED2 is unique in almost all visual categories.

Chemical Analysis.

Low MW Terpene Analysis (136). Sesquiterpene Analysis (204). Cannabinoid Analysis (>284). Chemical analysis for RED2 plants is summarized in Tables 11 and 12.

TABLE 11

Chemical analysis of flower samples for RED2 for Sample # 2785-4:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.26 | ND | 17.10 | <0.1 | ND | <0.1 | <0.1 |
| Total content for unheated flower sample, mg/g | | | | | | |
| 2.6 | ND | 171.0 | <0.1 | ND | 0.7 | 0.1 |
| Estimated total content for ideally heated flower sample, % by wt. | | | | | | |
| ND | 10.8 | ND | ND | <0.1 | ND | <0.1 |

ND = Not determined.

Note:
Most of the acid cannabinoids (e.g., THCA) readily converts to their neutrals (THC) upon heating, giving different properties.

TABLE 12

The cannabinoid profiles, unheated, % by wt for Sample #: 2785-4
Cannabinoid Profile % by wt

| | |
|---|---|
| THCA | 17.10 |
| $\Delta^9$-THC | 0.26 |
| $\Delta^8$-THC | <0.03 |
| THCA-C4 | 0.03 |
| THCVA | 0.21 |
| THCV | <0.03 |
| CBDA | 0.07 |
| CBD | <0.03 |
| CBCA | 0.06 |
| CBC | <0.03 |
| CBGA | <0.03 |
| CBG | 0.39 |
| CBLA | <0.03 |
| CBNA | <0.03 |
| CBN | <0.03 |

GRE1

Description of Breeding Stock.

Inflorescences were obtained and isolated and put into conditions proper for their germination.

The seeds which germinated grew identically. However, the seedlings were selected for the phenotype that is more densely covered in trichomes, where the oil content of the gland heads was higher than other phenotypes of this variety.

Hypothesized Genetics.

"*Cannabis* indica ssp. *afghanica* WLD "Afghan #1" x *C. indica* ssp. indica NLD hybrid Propagation and Vegetative Growth.

Cuttings from GRE1 are marked by 9-finger very thin leaflet sets with internode buds asymmetrically located on alternate sides on main shoot. In particular, the internode space of this variety tends to be extremely large. Plants are tall, frail and stretchy. Cuttings root appears within 10-14 days.

GRE1 grows tall and stretchy with flimsy stems and embodies what it means to be a true hybrid.

GRE1 grows with asymmetrical bud and leaf sets. Vegetative growth is marked by a lush green (Munsell ID) hue with lime green thin stalks.

Leaflets are longer and thinner than varieties. Plants have a vigorous hybrid character. GRE1 has little or no purple color on the plant. The stand-out quality is the high amount of trichomes and the high amount of oil. Plant stalks have a sweet citrus 'creamsicle' scent.

Plant canopy is dense and even topping near flowering is encouraged for even growth.

Onset of Flowering and Inflorescences.

Leaves are 9 and 7 leaflet patterns with 7 being predominant and overall decreasing to 1 and to none in the presence of female flowers. In particular, flower onset is fast by comparison to most varieties.

Trichome density and smell are almost immediate. Female flowers are clustered to do decreased internode spacing. Again, this variety tends to be more densely covered with trichome bodies than its parent and other green class varieties. In fact, the inflorescences are very dense and have large calyxes covered in highly resinous glands that exhibit this variety's distinct green class creamsicle scent after only 7-10 days. As inflorescences mature, the density compact sets compound to form orange and bright green extremely oily buds. In particular, the oily character of these flowers set this green class apart from its parent and other green class varieties.

Description of Finished Flower.

GRE1 defines sweet, delicious medicine/medicinal with functional mental effects. This variety has resin production akin to Afghan and psychoactivity reminiscent of original Green class.

GRE1 has aromas of citrus, brown sugar, and banana nut bread combine to produce a fantastic fruity hashish flavor when smoked. It is noted for mood elevation and daytime bursts of energy that provide for short-term pain relief.

Chemotype Description for Patient.

Relative potency: Strong. Headspace Terpenes: pinenes, myrcene, limonene, and ocimene. Caryophyllene content: Medium.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein.

Flower onset was initiated with 12/12 day/night at approximately 16" in vegetative height. Total biomass ~160 g, finished flowers ~50 g, and/or ~50 g of seed per plant.

Potential Uses of this Line.

Potential uses of GRE1 include but are not limited to medical applications, extractions, commercial raw material (e.g., chemical), fiber and pulp.

Patient Testimonials/Comments and Visual Observations.

Patients rave about the great experience of using this plant. The flowers of GRE1 consistently produce approximately 2.0% CBGA in finished flowers. Its wonderful smell/taste is patient's major reason for appeal.

Chemical Analysis.

Low MW Terpene Analysis (136). Sesquiterpene Analysis (204). Cannabinoid Analysis (>284). Chemical analysis for GRE1 plants is summarized in Tables 13 and 14.

TABLE 13

Chemical analysis of flower samples for GRE1 for Sample # 2651-4:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.74 | ND | 20.52 | <0.1 | ND | <0.1 | <0.1 |
| Total content for unheated flower sample, mg/g | | | | | | |
| 7.4 | ND | 205.2 | <0.1 | ND | 0.9 | 0.2 |
| Estimated total content for ideally heated flower sample, % by wt. | | | | | | |
| ND | 13.3 | ND | ND | <0.1 | ND | <0.1 |

ND = Not determined.
Note:
Most of the acid cannabinoids (e.g., THCA) readily converts to their neutrals (THC) upon heating, giving different properties.

TABLE 14

The cannabinoid and terpene profiles, unheated, % by wt for Sample #: 2651-4

| Cannabinoid Profile % by wt | | Terpenoid Profile % by wt | |
|---|---|---|---|
| THCA | 20.52 | terpinolene | <0.01 |
| Δ⁹-THC | 0.74 | myrcene | <0.01 |
| Δ⁸-THC | <0.03 | Limonene | <0.01 |
| THCA-C4 | 0.04 | Linalool | 0.12 |
| THCVA | 0.18 | Caryophyllene Oxide | 0.02 |
| THCV | <0.03 | Beta-Caryophyllene | 0.22 |
| CBDA | 0.09 | Phytol | <0.01 |
| CBD | <0.03 | alpha-pinene | 0.17 |
| CBCA | 0.16 | | |
| CBC | <0.03 | | |
| CBGA | 1.48 | | |
| CBG | 0.28 | | |
| CBLA | 0.15 | | |
| CBNA | <0.03 | | |
| CBN | <0.03 | | |

PUR3

Description of Breeding Stock.

Inflorescences were obtained for a landrace of purple class pollinated with a hermaphroditic purple class variety and seeds from these inflorescences were isolated and put into conditions proper for their germination.

The seeds which germinated grew very uniformly in appearance. However, upon flower onset, the seedlings were selected for the two phenotypes that most smelled like 'grape and dank', and producing flowers with the highest trichome density and robust examples of these two phenotypes were subsequently crossed to create PUR3.

Hypothesized Genetics.

"2007 SB PUP1×2009 PPS7".

Propagation and Vegetative Growth.

Cuttings from PUR3 are marked by 7-finger leaflet sets with internode buds asymmetrically located on alternate sides on main shoot. In particular, the internode space of this variety tends to be decreased. Short, squatty and bushy. Cuttings root within 10-14 days.

The PUR3 grows stout in the traditional 'Christmas tree' shape. PUR3 grows with asymmetrical bud and leaf sets. Vegetative growth is marked by a deeper off green (Munsell ID) hue with lime green thin stalks. Leaflets are longer and thinner than varieties. When healthy, sun leaves are gigantic. It has vigorous hybrid character. The stand-out quality is the high amount of trichomes and the high amount of oil. There is an extremely high cannabinoid content in PUR3. Stalks have a sweet 'dank' scent. Canopy dense and do not need to top.

Onset of Flowering and Inflorescences.

Leaves are 7 leaflet patterns with 7 being predominant and overall decreasing to 1 and to none in the presence of female flowers. In particular, flower onset is fast by comparison to most varieties.

Trichome density and smell are almost immediate. Female flowers are clustered to do decreased internode spacing. Again, this variety tends to be more densely covered with trichome bodies than its parents and other purple varieties. In fact, the inflorescences are very dense and have large calyxes covered in highly resinous glands that exhibit this variety's distinct grape lollipop scent after only 7-10 days. As inflorescences mature, the density compact sets compound to form deep purple and dark green extremely oily buds. In particular, the oily character of these flowers set this purple apart from its parent and other green class varieties.

Description of Finished Flower.

PUR3 defines sweet, delicious grape flavored medicine with functional mental effects and pain relief. This variety has resin production akin to Afghan and psychoactivity reminiscent of the PUR3. PUR3 has aromas of grape, sweet sugar, and dank which all combine to produce a fantastic grape flavor when smoked. It is noted for mood elevation, short-term pain relief and hunger stimulation.

Chemotype Description for Patient.

Relative potency: very strong. Headspace Terpenes: pinenes, myrcene, and limonene. Caryophyllene content: high.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein.

Flower onset was initiated with 12/12 day/night at approximately 16" in vegetative height. Total biomass ~160 g, finished flowers ~50 g, and/or ~50 g of seed per plant.

Potential Uses of this Line.

Potential uses of PUR3 include but are not limited to medical applications, extractions, commercial raw material (e.g., chemical), fiber and pulp.

Patient Testimonials/Comments and Visual Observations.

Patients rave about the great experience. This flower consistently produces approximately 2.0% CBGA in finished flowers. Its wonderful smell/taste is patient's major reason for appeal.

Chemical Analysis.

Low MW Terpene Analysis (136). Sesquiterpene Analysis (204). Cannabinoid Analysis (>284).

YEL3

Description of Breeding Stock.

Inflorescences were obtained from an unknown landrace., Seeds from these inflorescences were isolated and put into conditions proper for their germination. The seeds which germinated grew uniformly in appearance. However, the seedlings were selected for their narrow-leafleted tropical cannabis morphology and pinene production to create YEL3.

Hypothesized Genetics.

"Cannabis indica ssp. indica NLD "Thai" x C. indica ssp. indica NLD "Highland Mexican."

Propagation and Vegetative Growth.

Cuttings from YEL3 are marked by 9-finger leaflet sets with internode buds asymmetrically located on alternate sides on main shoot. In particular, the internode space of this variety tends to be lengthy and stretchy (~4" veg, decreasing flower onset). The plants are tall, robust and lanky. Cuttings root within 10-14 days.

The YEL3 grows tall and strong with pronounced apical dominance. YEL3 grows with asymmetrical bud and leaf sets. Vegetative growth is marked by a lighter dark green (Munsell ID) hue with purple undersides and strong hollow stalks. When healthy, sun leaves are point upward toward light source at twisted angles. The stems are strong and fibrous. The stand-out quality is the high amount of trichomes and the high amount of oil. YEL3 has stalks with a sweet scent. Plant canopy is sparse with scattered bud formation. Topping encouraged.

Onset of Flowering and Inflorescences.

Leaves are 9 leaflet patterns with 9 being predominant and overall decreasing to 1 and to none in the presence of female flowers. In particular, flower onset is fast by comparison to most varieties.

Trichome density and smell are almost immediate. Female flowers are sparse due to large internode spacing. Again, this variety tends to be more densely covered with trichome bodies than its parents and other varieties. The flowers are not compact or well-formed. Inflorescences are spirals of individual foxtails that form a 'coral' looking structure. Although buds are made of individual spirals, the inflorescences are dense and tightly packed. As inflorescences mature, the density compact sets compound to form bright green and extremely oily buds.

Description of Finished Flower.

YEL3 has descended from the great Oaxacan and Thai cannabis landrace plants of the 1970's. This variety delivers an intense "up" stimulating effect that can be great for countering the debilitating aspects of many medical conditions. A complex aroma of spicy spruce and lemon peel release a cornucopia of sweet and spicy piney flavors when smoked. It is often characterized by a clear head, accompanied by mood elevation.

Chemotype Description for Patient.

Relative potency: very strong. Headspace Terpenes: pinenes, myrcene, limonene, ocimene, and terpinolene. Caryophyllene content: medium.

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days). Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying.

Slow drying followed by a one to two month curing process.

Yield Data.

Yield was determined on a 'per plant' basis using the specified cultivation techniques employed. In this case, indoor CEA technique following the protocol described elsewhere herein. Flower onset was initiated with 12/12 day/night at approximately 16" in vegetative height. Total biomass ~120 g, finished flowers ~40 g, and/or ~30 g of seed per plant.

Potential Uses of this Line.

Potential uses of YEL3 include but are not limited to medical applications, extractions, commercial raw material (e.g., chemical), fiber and pulp.

Patient Testimonials/Comments and Visual Observations.

Plants have a very interesting from an organoleptic standpoint and are unique in almost all visual categories.

Chemical Analysis.

Low MW Terpene Analysis (136). Sesquiterpene Analysis (204). Cannabinoid Analysis (>284). Chemical analysis for YEL3 plants is summarized in Tables 15-17.

TABLE 15

Chemical analysis of flower samples for YEL3 for Sample # 2788-1:

| THC | | | CBD | | CBN | |
|---|---|---|---|---|---|---|
| Average | Maximum | THCA | Average | Maximum | CBDA | Maximum |
| Total content for unheated flower sample, % by wt. | | | | | | |
| 0.17 | ND | 18.51 | <0.1 | ND | 0.16 | <0.1 |
| Total content for unheated flower sample, mg/g | | | | | | |
| 1.7 | ND | 185.1 | <0.1 | ND | 1.6 | <0.1 |
| Estimated total content for ideally heated flower sample, % by wt. | | | | | | |
| ND | 11.5 | ND | ND | 0.1 | ND | <0.1 |

ND = Not determined.

Note:
Most of the acid cannabinoids (e.g., THCA) readily converts to their neutrals (THC) upon heating, giving different properties.

TABLE 16

The cannabinoid and terpene profiles, unheated, % by wt for Sample #: 2788-1

| Cannabinoid Profile % by wt | | Terpenoid Profile % by wt | |
|---|---|---|---|
| THCA | 18.51 | terpinolene | <0.01 |
| $\Delta^9$-THC | 0.17 | myrcene | 0.16 |
| $\Delta^8$-THC | <0.03 | Limonene | <0.01 |
| THCA-C4 | 0.03 | Linalool | 0.02 |
| THCVA | 0.07 | Caryophyllene Oxide | <0.01 |
| THCV | <0.03 | Beta-Caryophyllene | 0.25 |
| CBDA | 0.16 | Phytol | <0.01 |
| CBD | <0.03 | alpha-pinene | 0.06 |
| CBCA | 0.56 | | |
| CBC | <0.03 | | |
| CBGA | 1.13 | | |
| CBG | 0.82 | | |
| CBLA | <0.03 | | |
| CBNA | <0.03 | | |
| CBN | <0.03 | | |

TABLE 17

Chemical analysis of flower samples for YEL3 for Sample # 2785-1:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.22 | ND | 19.23 | <0.1 | ND | 0.13 | <0.1 |
| Total content for unheated flower sample, mg/g | | | | | | |
| 2.2 | ND | 192.3 | <0.1 | ND | 1.3 | 0.2 |
| Estimated total content for ideally heated flower sample, % by wt. | | | | | | |
| ND | 12.0 | ND | ND | <0.1 | ND | <0.1 |

ND = Not determined.

Note:
Most of the acid cannabinoids (e.g., THCA) readily converts to their neutrals (THC) upon heating, giving different properties.

WHI3

Description of Breeding Stock.

Inflorescences were obtained for an unknown landrace. Seeds from these inflorescences were isolated and put into conditions proper for their germination. The seeds which germinated grew uniformly in appearance. However, the seedlings were selected for trichome density and hybrid leaf morphology to create WHI3.

Hypothesized Genetics.

"*Cannabis* indica ssp. *afghanica* WLD "Afghan #1" x *Cannabis* indica ssp. indica NLD "Brazilian" x *C. indica* ssp. indica NLD "Indian."

Propagation and Vegetative Growth.

Cuttings from WHI3 are marked by 5-finger leaflet sets with internode buds asymmetrically located on alternate sides on main shoot. In particular, the internode space of this variety tends to be shorter and stout (~2-4" veg, decreasing flower onset). The plants are short, robust and bushy. Cuttings root within 10-14 days.

The WHI3 grows short and bushy with classic 'Christmas tree' apical dominance. WHI3 grows with asymmetrical bud and leaf sets. Vegetative growth is marked by a dark green (Munsell ID) hue with green undersides and hard wood like stalks. When healthy, sun leaves are point upward toward light source and 'reach'. The stems are strong and fibrous. The stand out quality is the high amount of trichomes and the high amount of oil. The flower sets look 'white' before most other varieties. Stalks are sweet scent. Plant canopy is dense with clustered bud formation. Topping discouraged.

Onset of Flowering and Inflorescences.

Leaves are 5 leaflet patterns with 5 being predominant and overall decreasing to 1 and to none in the presence of female flowers. In particular, flower onset is fast by comparison to most varieties.

Trichome density and smell are almost immediate. Female flowers are dense and thick due to relatively small internode lengths. Again, this variety tends to be more densely covered with trichome bodies than other varieties in the white class. The flowers are compact and well-formed in the shape of pinecones. Pistils are fat and of high density. As inflorescences mature, the density compact sets compound to form bright neon-green flowers that give way to red-orange hair. It is marked by unusually high sesquiterpene content and extremely resinous buds. Inflorescences are subject to fungal infestation due to large size and extreme density.

Description of Finished Flower.

WHI3 produces prodigious amounts of psychoactive resin. This variety was derived from Brazilian, Indian, and Afghan gene pools. Its aroma of green classy, balsamic, pineapple gazpacho delivers a sweet, hashy flavor when smoked. It is noted for fast-onset psychoactivity reminiscent of traditional *cannabis* experiences that will leave you right where it found you. Happiness induced pain relief and considerable relaxation.

Chemotype Description for Patient.

Relative potency: very strong. Headspace Terpenes: pinenes, myrcene, limonene, humulene, and naphthalene. Caryophyllene content: very high

Description of Planting, Harvesting and Processing of the Plants.

This variety is asexually propagated via taking cuttings of shoots and putting them in rock wool cubes. These cubes were presoaked with pH adjusted water and kept warm (~80° C.). Full trays were covered, left under 18 hours of light and allowed to root (7-14 days).

Upon root onset, the plantlets were transplanted into rigid 1 gallon containers filled with a proprietary soil mix A and remain in 18 hours of daylight for another 14-21 days. Once root bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and plant dismantled to result in approximately 12" branches covered in inflorescences and trichomes. The goal in harvesting is to realize that we are actually harvesting trichome heads but not 'buds'. Thus, great care is taken not to disturb the trichome heads and as much of the plant remains intact as possible to promote even and slow drying. Slow drying followed by a one to two month curing process.

Yield Data.

Yield was determined on a 'per plant' basis and determined by specified cultivation techniques employed. In this case, indoor CEA technique following the protocol described elsewhere herein. Flower onset was initiated with 12/12 day/night at approximately 16" in vegetative height. Total biomass ~140 g, finished flowers ~50 g, and/or 50 g of seed per plant.

Potential Uses of this Line.

Potential uses of WHI3 include but are not limited to medical applications, extractions, commercial raw material (e.g., chemical), fiber and pulp.

Patient Testimonials/Comments and Visual Observations.

Very interesting from an organoleptic standpoint (sweet Amsterdam flavor) and a caryophyllene content standpoint. Happy laughing high. WHI3 has the burnt scent of 1990's landraces.

Chemical Analysis.

Low MW Terpene Analysis (136). Sesquiterpene Analysis (204). Cannabinoid Analysis (>284). Chemical analysis for WHI3 plants is summarized in Tables 18 and 19.

TABLE 18

Chemical analysis of flower samples for WHI3 for Sample # 2651-2:

| THC | | | CBD | | | CBN |
|---|---|---|---|---|---|---|
| Average | Maximum | THCA | Average | Maximum | CBDA | Maximum |
| Total content for unheated flower sample, % by wt. | | | | | | |
| 0.27 | ND | 18.96 | <0.1 | ND | <0.1 | <0.1 |
| Total content for unheated flower sample, mg/g | | | | | | |
| 2.7 | ND | 189.6 | <0.1 | ND | 0.9 | 0.1 |
| Estimated total content for ideally heated flower sample, % by wt. | | | | | | |
| ND | 11.9 | ND | ND | <0.1 | ND | <0.1 |

ND = Not determined.
Note:
Most of the acid cannabinoids (e.g., THCA) readily converts to their neutrals (THC) upon heating, giving different properties.

TABLE 19

The cannabinoid and terpene profiles, unheated, % by wt for Sample #: 2651-2

| Cannabinoid Profile | | Terpenoid Profile | |
|---|---|---|---|
| | % by wt | | % by wt |
| THCA | 18.96 | terpinolene | <0.01 |
| $\Delta^9$-THC | 0.27 | myrcene | <0.01 |
| $\Delta^8$-THC | <0.3 | Limonene | <0.01 |
| THCA-C4 | 0.04 | Linalool | 0.07 |
| THCVA | 0.09 | Caryophyllene Oxide | <0.01 |
| THCV | <0.03 | Beta-Caryophyllene | 0.15 |
| CBDA | 0.09 | Phytol | <0.01 |
| CBD | <0.03 | alpha-pinene | 0.31 |
| CBCA | 0.08 | | |
| CBC | <0.03 | | |
| CBGA | 0.19 | | |
| CBG | 0.16 | | |
| CBLA | 0.04 | | |
| CBNA | <0.03 | | |
| CBN | <0.03 | | |

CBD5

TABLE 19.1

CBD5 cannabinoid profile

| | Cannabinoids (UHPLC) | | | | | | | | | | | | |
|---|---|---|---|---|---|---|---|---|---|---|---|---|---|
| | THCA | | CBDA | | CBGA | | THC | | CBD | | CBG | | D8-THC | |
| Sample | Wt % | 95% CI | Wt % | 95% CI | Wt % | 95% CI | Wt % | 95% CI | Wt % | 95% CI | Wt % | 95% CI | Wt % | 95% CI |
| CBD5 | 5.24% | 0.19% | 10.77% | 0.83% | 0.30% | 0.14% | 0.20% | 0.13% | 0.14% | 0.02% | 0% | 0% | 0.11% | 0.02% |

| | Cannabs by HPLC | | THCA:CBDA by HPLC | | Cannabs/Terps (HPLC) | |
|---|---|---|---|---|---|---|
| Sample | Wt % | 95% CI | Wt % | 95% CI | Ratio | 95% CI |
| CBD5 | 16.76% | 0.74% | 0.49 | 0.04 | 10.41 | 1.53 |

TABLE 19.2

CBD5 terpene profile.

| | Terpenes (GC-FID) | | | | | | | | |
|---|---|---|---|---|---|---|---|---|---|
| Sample | terpinolene Wt % | alpha phellandrene Wt % | beta ocimene Wt % | carene Wt % | limonene Wt % | gamma terpinene Wt % | alpha pinene Wt % | alpha terpinene Wt % | beta pinene Wt % | fenchol Wt % |
| CBD5 | 0% | 0% | 0.00122% | 0% | 0.07% | 0% | 0.46% | 0% | 0.12% | 0.23% |

| | Terpenes (GC-FID) | | | | | | | |
|---|---|---|---|---|---|---|---|---|
| Sample | camphene Wt % | alpha terpineol Wt % | alpha humulene Wt % | beta caryophyllene Wt % | linalool Wt % | caryophyllene oxide Wt % | myrcene Wt % | Total identified oil (wt%) Wt % |
| CBD5 | 0% | 0% | 0.0009% | 0.23% | 0.09% | 0.01% | 0.36% | 1.64% |

Example 2. Development of Medical *Cannabis* Varieties

In another objective of the present invention, the Classes of *Cannabis* Varieties of Example 1 are used in *cannabis* breeding programs to develop Medical *Cannabis* plants and varieties. Furthermore, the Medical *Cannabis* varieties developed according to the present invention have specific flavor(s) in accordance with one of the classes of Classes of *Cannabis* Varieties as discussed above.

The general idea behind this approach was in response to the fact that currently available *cannabis* varieties have been skewed towards THC production, which has increased the likelihood of adverse effects from the elevated levels of psychoactivity that these high-THC varieties produce.

Contemporary illicit "recreational" marijuana cultivars have been exclusively bred and selected primarily for their THC acid content, secondarily for their terpenoid aroma and flavor chemistry, and rarely for their production of the other cannabinoid acids, such as CBDA.

Cannabidiol (CBD), a cannabinoid that is rare in contemporary medical *cannabis* varieties, has been shown to reduce and modulate the psychoactivity of THC and also reduce some of THC's other adverse effects including tachycardia, anxiety, memory effects, etc. There is some evidence that CBD may reduce the buildup of tolerance to the effects of THC and also reduce the likelihood of *cannabis* dependency.

The breeding programs of the present invention were designed to combine lower THC with higher CBD so as to produce medical *cannabis* varieties. Furthermore, the medical *cannabis* varieties of the present invention were additionally selected for their ability to produce fragrant terpenoids that are appealing to patients and that may also provide a pharmacological activity that modifies, enhances or ameliorates the effects of THC. In contrast, publicly-available contemporary hemp varieties that are high in CBD do not produce the pleasing organoleptic attributes of contemporary high-THC marijuana cultivars. Thus, an objective of the present invention is to combine lower THC with higher CBD so as to produce medical *cannabis* varieties with these pleasing aromas and flavors.

Varieties of medical *cannabis* with 'determined' cannabinoid content and increased essential oil content are designed according to the present invention so as to reduce the adverse effects of THC and smoking while increasing organoleptic appeal.

One embodiment of the present invention is to produce medical *cannabis* varieties with high essential oil content, in particularly, mono- and sesquiterpenes. While THCA is of importance, the entourage effects of these terpenoids in concert with proper dosage of cannabinoids are a focus of the present invention. The breeding objectives of the present invention are opposite to the face of modern recreational marijuana breeding strategies which have focused almost solely on breeding for higher levels of THCA content alone.

According to the present invention a Class variety is crossed to a CBD line to produce F1 seed which were grown to produce F1 progeny. Five CBD lines were chosen to use in the initial breeding program: CBD1, CBD2, CBD3, CBD4 and CBD5. According to the present invention, each of these CBD lines is crossed to one or more *cannabis* varieties in a specific Class. So, for example, one or more GOLD Class varieties are crossed to each of CBD1, CBD2, CBD3, CBD4 and CBD5 to produce five F1 populations per Class variety to create GOLD Class x CBD combinations. Table 20 is a list of the iterations for each of the Class x CBD crosses.

TABLE 20

List of Class X CBD crosses.

| CBD1 Crosses | CBD2 Crosses | CBD3 Crosses | CBD4 Crosses | CBD5 Crosses |
| --- | --- | --- | --- | --- |
| GOLD X CBD1 | GOLD X CBD2 | GOLD X CBD3 | GOLD X CBD4 | GOLD X CBD5 |
| BRONZE X CBD1 | BRONZE X CBD2 | BRONZE X CBD3 | BRONZE X CBD4 | BRONZE X CBD5 |
| WHITE X CBD1 | WHITE X CBD2 | WHITE X CBD3 | WHITE X CBD4 | WHITE X CBD5 |
| FUSCIA X CBD1 | FUSCIA X CBD2 | FUSCIA X CBD3 | FUSCIA X CBD4 | FUSCIA X CBD5 |
| ORANGE X CBD1 | ORANGE X CBD2 | ORANGE X CBD3 | ORANGE X CBD4 | ORANGE X CBD5 |
| RED X CBD1 | RED X CBD2 | RED X CBD3 | RED X CBD4 | RED X CBD5 |
| YELLOW X CBD1 | YELLOW X CBD2 | YELLOW X CBD3 | YELLOW X CBD4 | YELLOW X CBD5 |
| SILVER X CBD1 | SILVER X CBD2 | SILVER X CBD3 | SILVER X CBD4 | SILVER X CBD5 |
| PURPLE X CBD1 | PURPLE X CBD2 | PURPLE X CBD3 | PURPLE X CBD4 | PURPLE X CBD5 |
| GRAY X CBD1 | GRAY X CBD2 | GRAY X CBD3 | GRAY X CBD4 | GRAY X CBD5 |
| JADE X CBD1 | JADE X CBD2 | JADE X CBD3 | JADE X CBD4 | JADE X CBD5 |
| BLUE X CBD1 | BLUE X CBD2 | BLUE X CBD3 | BLUE X CBD4 | BLUE X CBD5 |
| BLACK X CBD1 | BLACK X CBD2 | BLACK X CBD3 | BLACK X CBD4 | BLACK X CBD5 |
| GREEN X CBD1 | GREEN X CBD2 | GREEN X CBD3 | GREEN X CBD4 | GREEN X CBD5 |
| MISC X CBD1 | MISC X CBD2 | MISC X CBD3 | MISC X CBD4 | MISC X CBD5 |

In one representative version of this breeding regime the resultant F1 progeny can be selfed to produce F2 seed which are grown to produce F2 progeny. Selection for desirable phenotypes and/or genotypes can be conducted within the F2 progeny since the selections can be maintained (i.e., fixed) via asexual reproduction. Alternatively, the F2 progeny can be crossed among themselves to produce a bulked F3 population from which desired progeny can be selected and/or further generations of crossing can be conducted. Regardless of the exact selfing/selection procedure, selected lines can be chosen so as to have a total THC content ≥2% but ≤90.0%, a total CBD content ≥1.5%, and an aroma and flavor(s) typical of its class. In another version of the present invention, regardless of the exact selfing/selection procedure, selected lines can be chosen so as to have a total THC:CBD ratio of 8:1 and approaching 1:1, and an aroma and flavor(s) typical of its class.

The lines can also be further selected for a specific content of certain other cannabinoids and/or of certain terpenes/terpenoids, and/or for additional phenotypic and genotypic characteristics. Desirable phenotypic characteristics include but are not limited to larger plant size (i.e., greater bulk or biomass), higher production of flower buds, larger flowers, more trichomes, shorter plant stature, ability to tolerate lower and/or higher growing temperatures, greater germination percentage, greater seedling vigor, more efficient water usage, disease resistance, pest resistance, and other desirable agronomic and production traits. For an overview of diseases and pests of importance to *cannabis* production see Clarke et al. (2000) *Hemp Diseases and Pests: Management and Biological Control: An Advanced Treatise* (CABI Publishing).

In an alternative version of this breeding regime the selected F2 progeny are backcrossed to the Class variety as the recurrent parent. Selection for desirable phenotypes and/or genotypes can be conducted after this initial backcross, after any subsequent backcross (e.g., progeny obtained after 2, 3, 4, 5, 6, 7, 8, 9 or more backcrosses). Selected lines will have a total THC content ≥2% but ≤90.0%, a total CBD content ≥1.5%, and an aroma and flavor(s) typical of its class. In another version of this breeding scheme selected lines can be chosen to have a total THC:CBD ratio of 8:1 and approaching 1:1, and an aroma and flavor(s) typical of its class. The lines can also be further selected for a specific content of certain other cannabinoids and/or of certain terpenes/terpenoids, and/or for additional phenotypic and genotypic characteristics.

The progeny resulting from any selection stage of either the selfing or backcrossing versions of the breeding regimes of the present invention can be asexually reproduced so as to fix and maintain the desirable THC content, CBD content, the aroma and flavor(s) typical of the desired class, and the other desirable phenotypic and/or genotypic characteristics. The resultant selected lines will be designated as classical medical *cannabis* varieties.

The progeny resulting from any stage of either the selfing or backcrossing versions of this regime can also be crossed to other *cannabis* plants/varieties within, between or among the various classes of *cannabis* so as to produce additional plants for selection and maintenance through asexual reproduction. In this way, medical *cannabis* varieties with various, desired flavor combinations can be produced and subsequently maintained through asexual reproduction.

The resultant medical *cannabis* plants of the present invention also generally have more oil content per plant than contemporary marijuana varieties. More oil per plant means less plant matter is required per treatment/administration, thereby also further minimizing any health risks for medical *cannabis* smokers.

Breeding plants with increased CBDA content will alleviate most of the commonly recognized real and perceived adverse effects of high THC *cannabis*. A direct result of increased CBDA is lower THC content because THCA synthase and CBDA synthase are allelic. Thus, another objective of the present invention is to create medical *cannabis* varieties with an 'optimal' dose of THCA and resulting in the most efficacious ratio of CBDA:THCA.

According to the present invention, it is possible to apply dosage data to creating custom blended granular mixes for rolled delivery, pellets for bowls and house one-hitters, extracts for dabs, etc. with the flowers of these highly resinous newly-developed varieties with designed cannabinoid content so as to reduce adverse effects associated with THC.

Gold Class Breeding Regime

Basic Breeding Scheme.

The initial cross for the Gold Class Breeding Regime that will be conducted is as follows: P1 (GOLD Line (GO13)×P2 (CBD Line (CBD1201). The hybrid cross between Parent 1 (P1) and Parent 2 (P2) could only be achieved by induction of staminate flowers on the pistillate plants by an exogenous application of the chemical silver thiosulfate. This process allows otherwise pistillate (female) plants to be coaxed to produce staminate, pollen bearing flowers. During this process, to investigate and exclude the possibility of maternally inherited genetic factors, reciprocal crosses will be made where both P1 will be induced to produce pollen and fertilize P2 (Line 1A), and P2 will be induced to produce pollen and fertilize P1 (Line 1B).

These crosses will result in the production of two F1 populations=CBD-GOLD Lines 1A, 1B. Individuals from the F1 lines of each F1 population will be analyzed via GC/MS to determine their respective chemotypes. It is expected that the F1 populations will comprise individuals that show a Chemotype II cannabinoid distribution, with intermediate levels of both tetrahydrocannabinol (THC) and cannabidiol (CBD).

Plants with suitable terpene contents and profiles will be 'self-fertilized' to create a series F2 segregating populations or families; all non-desirable lines will be rejected from the breeding regimen. In this way, a series of F2's will be created=1AF2a, 1AF2b, 1AF2c, 1BF2a, 1BF2b, 1BF2c, etc.

F2 families will be propagated and screened via GC/MS to determine individual chemotypes; it is expected that in the F2 segregating populations we will see chemotype I, chemotype II, and chemotype III plants. Chemotype I and II plants will be discarded and only chemotype III plants will be retained and again screened by GC/MS to evaluate their suitability in terms of terpene content and profile.

These selected chemotype III plants can be self fertilized or mated inter se and will retain the chemotype III cannabinoid profile within the population. It may also be desirable to mate selected F2 lines via a backcross scheme to the P1 GO13 to reinforce the GOLD genetic background, although doing so will re-introduce B(t) alleles (i.e., the alleles that encode for THC production) into the breeding population, resulting in a population of chemotype II plants which will again require self fertilization to create a segregating population, and subsequent screening of the segregating population to eliminate chemotype I and chemotype II plants, only retaining the chemotype III plants that approach the ideotype.

Backcross Breeding Scheme.

The following backcross breeding procedure will also be accomplished according to the present invention:

P1 (GOLD Line (GO13)×P2 (CBD Line (CBD1201)

The hybrid cross between P1 and P2 can only be achieved by induction of staminate flowers on the pistillate plants by an exogenous application of the chemical silver thiosulfate. This process allows otherwise pistillate (female) plants to be coaxed to produce staminate, pollen bearing flowers. During this process, to investigate and exclude the possibility of maternally inherited genetic factors, reciprocal crosses will be made where both P1 will be induced to produce pollen and fertilized P2 (Lina 1A), and P2 will induced to produce pollen and fertilize P1 (Line 1B). The resultant F1=CBD-GOLD Lines 1A, 1B.

It should be noted for accuracy that P1 (GO13) is a chemotype I plant, and crossing it to P2 (CBD Line (CBD1201), a chemotype III plant, the resulting population will yield all Chemotype II plants of intermediate THC and CBD levels, in agreement with de Meijer, E P, Bagatta, M, Carboni, A, Crucitti, P, Moliterni, V M, Ranalli, P, Mandolino, G (2003) The inheritance of chemical phenotype in *Cannabis sativa* L. Genetics 163(1):335-346.

Individuals from the F1 lines will be analyzed via GC/MS to determine their respective chemotypes. In accordance with de Meijer (Id) it is expected that the F1 populations will comprise individuals that show a Chemotype II cannabinoid distribution, with both intermediate levels of tetrahydrocannabinol (THC) and cannabidiol (CBD). Plants with suitable terpene contents and profiles from this population will be backcrossed to the P1 parent to reinforce the genetic background of P1; this population will be labelled BC11; (Backcross 1 to P1).

Plants from BC11 will be cannabinoid chemotype I and chemotype II; chemotype I plants will be discarded, and chemotype II plants approaching the desired terpene profile will be self crossed to yield an F2 population. The BC11F2 population will be grown, and again analyzed via GC/MS to reveal the chemotype of the plants in the population. This population will yield 25% chemotype I plants, 50% chemotype II plants, and 25% chemotype III plants; only chemotype III plants will be kept for further terpene analysis, all others will be discarded. Suitable chemotype III plants approaching the desired terpene profile will be mated via a backcross scheme to the P1 plant (GOLD Line (G013)). This population will be labeled BC21; Backcross 2 to P1).

BC21 will produce chemotype II plants. Individuals will be screened for desired terpene profile and content, and desirable plants will again be self-fertilized, to yield a population producing plants in the expected ratio of 25% chemotype I, 50% chemotype II, and 25% chemotype III. Chemotype III plants will be retained for further terpene profiling and analysis, all other plants will be discarded. After terpene analysis, selected plants from the chemotype III individuals will again be backcrossed to the P1 plant (GOLD Line (GO13)). This population will be labeled BC31; Backcross 3 to P1).

From this mating, the resulting population will be comprised of only chemotype II plants, and it is expected that plants of the desired terpene profile will be isolated after analysis for terpene profile and content.

Silver Class Breeding Regime

Using the procedures described above for the Gold Class Breeding Regime, the initial cross for the Silver Class Breeding Regime will be as follows: P1 SILVER Line (SIL4)×P2 CBD Line (CBD1201). The basic and backcross selection and breeding procedures for this class are as described above for the Gold Class Breeding Regime.

Green Class Breeding Regime

Using the procedures described above for the Gold Class Breeding Regime, the initial cross for the Green Class Breeding Regime will be as follows: P1 GREEN Line (GRE1)×P2 CBD Line (CBD1201). The basic and backcrossing selection and breeding procedures for this class are as described above for the Gold Class Breeding Regime.

Yellow Class Breeding Regime

Using the procedures described above for the Gold Class Breeding Regime, the initial cross for the Yellow Class Breeding Regime will be as follows: P1 YELLOW Line (YEL3)×P2 CBD Line (CBD1201). The basic and backcrossing selection and breeding procedures for this class are as described above for the Gold Class Breeding Regime.

Purple Class Breeding Regime

Using the procedures described above for the Gold Class Breeding Regime, the initial cross for the Purple Class Breeding Regime will be as follows: P1 PURPLE Line (PUR3)×P2 CBD Line (CBD1201). The basic and backcrossing selection and breeding procedures for this class are as described above for the Gold Class Breeding Regime.

Example 3. Tracking of *Cannabis* Plants During Production, Processing and Use

Medical *cannabis* must be easily distinguished from recreational *cannabis* and hemp, allowing it to be tracked from seed to plant to processing to sale ("seed to sale" tracking). This can be accomplished by tagging the seeds, harvested material, and marketed product in a variety of different ways. According to the present invention it is possible to provide instantaneously the use of forensic-style forensic audit capabilities to indoor horticulture. For example, the compositions and methods of the present invention can be used to track medical *cannabis* plants, medical *cannabis* plant parts, ground medical *cannabis* plant material, compressed medical *cannabis* plant material, etc. Thus, according to the present invention, one can track the chemotype for an individual plant or group of plants from seed to flower and beyond.

First, the seeds and plants may be implanted with a tracking device, such as via radio-frequency identification (RFI)) using an RFID tag or chip, a telometric thread, a microchip, or a magnetic tag, which will allow real-time identification of the seed, plant, harvest, or final product.

In one non-limiting example, the seeds and plants are implanted with a very small active RFID tag or chip which will emit a unique address for each seed and/or plant to a reader. REFID is a wireless data collection technology that uses electronic tags for storing substantial amounts of data that can be used for tracking individual items. There are two basic types of RFID tags: passive and active. "Passive" tags have no power source but use the electromagnetic waves from a reader (e.g., the receiver) up to approximately 15 feet away to transmit back their contents. "Active" tags use a battery to transmit up to about 1,500 feet. The RFID tags are read when they are within the proximity of two-way radio transmitter-receivers, or readers, which send a signal to the tag and read its response. The handheld devices can easily be used to track the RFID tags integrated into the *cannabis* seeds, plants, and/or product.

Alternatively, the medical *cannabis* plants can be tagged by recombinantly engineering them to express a phenotypic trait unique to the strain. For example, a strain can be stably transformed to express bio-markers, generally proteins, that directly, or on contact with suitable substrates, yield a characteristic color, optical density, light emission, or fluorescence, Fluorescent bio-markers can include green fluorescent protein, red fluorescent protein, yellow fluorescent protein, blue fluorescent protein, or variants thereof that, when expressed, will emit a color under a particular wavelength. Detection devices for fluorescent bio-markers can have one or more excitation light sources for emitting light of a wavelength or a range of wavelengths suitable for inducing the fluorescence. In a non-limiting example, an expression cassette comprising red fluorescent protein is stably transformed into the plant cells using standard laboratory techniques. This protein will be expressed by the seed and/or plant, and when excited by a particular wavelength produced by a simple device, such as a hand-held light, can be easily identified by the red color.

Example 4. CBD Enhancement Dosage Technologies

While it is beneficial to increase the ratio of CBD:THC in medical *cannabis*, this typically is accompanied by a loss of the terpenoid constituents responsible for the aroma and flavor found in high THC *cannabis*. We can apply the optimum CBD:THC ratios discovered from studying the effects of the inhaled hybrids to blends, pellets, plugs, edibles, and all other medical *cannabis* products. The *cannabis* compositions and dosage technologies disclosed herein can be used to improve the dosage consistency and standards of raw flowers, blends, hashes or any other *cannabis* and *cannabis*-containing products provided by the present invention.

Blends comprising the *cannabis* strains of the present invention can be made by combining the plant material from a high CBD:THC strain in amounts calculated to deliver the proper dose of each compound to the patient with the plant material from a strain comprising high amounts of the desired terpenoids. The final blend contains CBD and T-IHC in the optimum dose described herein and also an amount of terpenoids adequate to provide a pleasant flavor and taste.

Alternatively, purified terpenoid extracts can be added to the plant matter from a high CBD:THC strain in a concentration so that the final product contains CBD and THC in the optimum dose and an amount of terpenoids adequate to provide a pleasant flavor and taste.

Finally, a purified cannabinoid extract, such as CBD extract, can be added directly to the plant matter from a *cannabis* strain comprising the desired terpenoids so that the final product contains CBD and THC in the optimum ratio/dose and an amount of terpenoids adequate to provide a pleasant flavor and taste.

These compositions can be used to make any type of desired medical *cannabis* product including, but not limited to, pellets, plugs, and edibles.

Example 5. Blended Bubble Pack Doses

It is important that the medical *cannabis* of the present invention be stable and possesses a long shelf-life when prepared for distribution to patients. This is achieved through proper drying and curing of the processed medical *cannabis* product. However, the shelf-life can be increased by proper airtight packaging such as in a bubble pack or a blister pack.

The longevity (i.e., shelf-life) of the packaged *cannabis* can be further extended by Modified Atmosphere Packaging (MAP), a technique used for prolonging the shelf-life of fresh or minimally processed foods. In this preservation technique, the air surrounding the product in the package is removed by vacuum or modified to contain different levels of nitrogen, oxygen, and carbon dioxide.

The *cannabis* products of the present invention, including the blended *cannabis* compositions described herein, can be packaged in a bubble pack in either multi- or single-dose units to increase product longevity. Each single-dose unit packaged in the bubble pack will comprise the optimum CBD:THC dose identified by the instant invention. In one embodiment, the compositions of the invention are packaged as single-dose units to ensure the patient receives a correct, standardized dose and to protect the product integrity.

Example 6. Use of the Invention as Expectorant

When vaporized and inhaled, the medical *cannabis* varieties of the present invention are an effective expectorant. Use of the high CBD containing *cannabis* varieties described herein can be used, for example, in the treatment of congestion and upper respiratory diseases.

One mechanism through which medical *cannabis* may act as an expectorant is through the activity of terpin hydrate, a precursor to terpineol which has been identified in several *cannabis* strains (See, Ross and ElSohly, (1996). J. Nat. Prod. 59:49-51 and Fischedick et al., (2010) Phytochemistry 71:2058-2073). The presence of terpineol, instead of terpin hydrate, in the samples after the *cannabis* is dried and heated may be due to a dehydration reaction of terpin hydrate to terpineol under thermal conditions. This chemical process may not occur if the *cannabis* is exposed to the lower heat of a vaporizer.

Inhalation of the vapors produced by high CBD containing medical *cannabis* exposed to a lower heat can act as an effective expectorant and can be useful in the treatment of congestion. Terpin hydrate was commonly used in the treatment of acute and chronic bronchitis, but it was removed from the market by the FDA, which cited a lack of efficacy (See, Code of Federal Regulations, Title 21, Volume 5, Apr. 1, 2009). However, the formulations studied were oral formulations comprising terpin hydrate, not vaporized, inhaled terpin hydrate which may prove more effective.

Example 7. Pelletization of Blended Ground Flowers for Bowls and Pipes

CBD Enhancement Dosage Technologies were used to create medical pre-pressed bowls of blended and pelletized *cannabis*. Novel design and pellet density were used to optimize dosage for vapor and combusted cannabinoid delivery. The purpose of this invention is to maximize the exposed surface area of the pelletized material to maximize contact with heated air to achieve optimal vaporization. The preferred embodiment is likely a very thin 'coin' shape.

Example 8. Plugs for Vaporization Technique (Specifically Dabbing)

CBD Enhancement Dosage Technologies were used to create medical pre-pressed gelatin-like balls for hot nail vaporization. The present invention provides novel designs and pellet density that is optimized for dosage and vaporization in pens and dab rigs. The purpose of this invention is to provide a precision pre-packed dose of *cannabis* oil for vaporization in an e-cigarette type device or using a hybrid glass or metal pipe that has been modified to operate at below combustion temperature levels.

Example 9. Horticultural Practice (Consistency)

All *cannabis* germplasm and cuttings of *cannabis* germplasm are established in identical environmental conditions (~80'C, 80% Humidity, CO2 variable, 3000 k lighting). Once roots are established, plants are transplanted into 1 gallon pots using a proprietary soil mix #1 heavily laded with beneficial microbes, nematodes and predator mites. Our soil system is crucial to establish consistent growth patterns and secondary metabolite production.

Plants are grown under 18 hours of light with 50% Metal Halide & 50% High Pressure Sodium Light bulbs generating the spectrum. The environmental conditions, distance from light, pots and soil are all proprietary.

Once roots are bound, or plants are approximately 12"-18", they are transplanted into 3 gallon pots with proprietary soil mix #2. Again, microbial content of soil and beneficials are a crucial contributor to the consistent production of medicine.

Plants are induced into flowering by undergoing a period of 72 hours of darkness which is followed by the light cycle of 12 hours of light and 12 hours of dark (20% Metal Halide and 80% High Pressure Sodium). Plants are trimmed, pruned and topped similar to fruit tree industry (I.e., a healthy number of budding sites distributed evenly throughout the canopy). The specific techniques employed are cultivar specific.

Environmental conditions, pots, distance from light, trellising techniques, carbon dioxide concentration and nutrient regimen are all proprietary.

Flowering period can last between fifty and ninety days. While plants can exceed 5' in height, canopies are 'shaped' in row crop tradition and kept at 18"-24".

Plants are culled if they are showing expressing stress genes and/or if they are showing any signs of variations. Ripeness is specifically determined by genetics.

Example 10. Feedback-Based Cultivation System

Some embodiments of the present invention are directed to systems, apparatuses, and methods for feedback-based cultivation of the herbal medicines described herein. FIG. 1 illustrates a system 100 for feedback-based cultivation of the herbal medicines described herein, according to some embodiments. The system 100 includes at least a computing apparatus 102, an environment management system 104, and a patient management system 106. The various components of the system 100 can be in communication as indicated by lines in FIG. 1 via a network (wherein a dotted line indicates an optional connection), which may be any type of network (e.g., a local area network or LAN, a wide area network or WAN, a virtual network, a telecommunications network, the internet and/or the like) implemented as a wired network and/or a wireless network. Any or all communications may be secured (e.g., encrypted) or unsecured, as is known in the art.

The environment management system 104 can be configured for production of the herbal medicines disclosed herein. In some embodiments, the environment management system 104 can be configured for managing a controlled environment for production of the herbal medicines disclosed herein. The controlled environment can include one or more software and/or hardware components monitored and/or controlled by the environment management system 104 including, but not limited to, one or more sensors, one or more controllers, one or more fertigation systems, and/or the like. For example, in some embodiments, the environment management system 104 can include controlled environment grow rooms, sensors, fertigation devices, and further computer networks and interfaces for monitoring/control of these aspects. In this manner, the disclosed embodiments are configurable to implement a smart grow room, where sensor technology and artificial intelligence-based software combine to assist cultivators to monitor the dozens of parameters that must be optimized to grow the highest quality and healthiest plants producing consistent levels of secondary metabolites (as will be described in more detail later). In some embodiments, the sensors can include soil sensors for taking soil measurements such as, but not limited to, soil moisture, electrical conductivity (EC), available soil moisture, potential gravity, temperature, and/or the like.

In some embodiments, where grow rooms are employed, multiple sensors per room can be employed. For example, the total density or number of sensors in each 'cell' (or room with five 4'×16' rows, ~150 plants, 15 plants per 4'×8' table) can vary from 2-4 per room. The number of sensors in a room can be dictated by the density of plants in each table. Two sensors are needed for each density, whether it is 15 or 21 plants per table, one on a boundary plant and one on a middle plant. Additional pairs of sensors can be added for a specific cultivar if it is known to have substantially different water usage than surrounding plants in the cell.

In some embodiments, the sensors can include sensors for air particulate/contamination measurements. In some embodiments, the sensor(s) includes a Thermo Scientific TEOM 1405 continuous particulate monitor. In some embodiments, the air sensor(s) can include environmental controllers having sensors associated therewith, such as the Sentinel CHHC-4 that measures, in real time, temperature, relative humidity, and carbon dioxide content. In such embodiments, the controller can also be employed for environmental control. For example, the CHHC-4's ability to hold a set point within a certain range of accuracy can be exploited.

In some embodiments, water and/or fertigation parameters can be measured by a variety of sensors, including pH, EC, flow rate, TDS, NPK, ppm of certain compounds, and/or others if desired. Some of these parameters can be determined via direct measurements, while other, such as ppm of some compounds, can be determined via dilution calculations. In some embodiments, water and/or fertigation parameters can be controlled using systems such as, but not limited to, the Hanna Instruments computerized fertigation system (Model HI 10000) that allows for mixing of four nutrient zones and one acid/buffer zone for pH control, and uses reliable and accurate Dosatron D8R venturi style injectors. The HI 10000 can also be hooked to a reservoir style system or in-line flow mixing, where the preferred method is likely reservoir for compost teas and inline for fertigation.

In some embodiments, the environment management system 104 can be configured to track active ingredients from their concentrations on the plant in the field, through production and processing. In some embodiments, the environment management system 104 can be configured to measure the production of key secondary metabolites and/or monitor their flux in concentration over time to better understand and control the mechanisms underlying their biosynthesis. In this manner, aspects of the environment management system 104 overcome challenges associated wit the production of herbal medicines that have multiple active ingredients, where consistent production of these active ingredients typically varies from crop to crop. Additional benefits are realized when a highly monitored controlled cultivation environment can be utilized in conjunction with timely chemical fertilizers that trigger the plants to produce these metabolites at the desired concentration. As a result, harvesting at the optimal time can guarantee consistent medicine. In some embodiments, the environment management system 104 can be further configured to optimize for individual metabolites of interest with troubleshooting mechanisms to identify issues before they impact a plant's primary or secondary metabolite production.

In some embodiments, the environment management system 104 can be structured in a multi tier manner and particularly in a three tier manner, with the primary order being a central control center/database, second order being an on-site pc interface station, and third order being an individual station such as a tablet interface. The data processing and analysis can be carried out by the more powerful control center computers, which can be equipped with the latest microcomputer needed for bidirectional data transmission, allowing them to communicate with the on-site PC stations and/or to the individual stations. The bidirectional data transmission between different facets of the network, such as the individual stations and on-site PCs, can be accomplished in the manner outlined in FIG. 2, which illustrates an exemplary and non-limiting embodiment of the environment management system 104.

Figure 2:
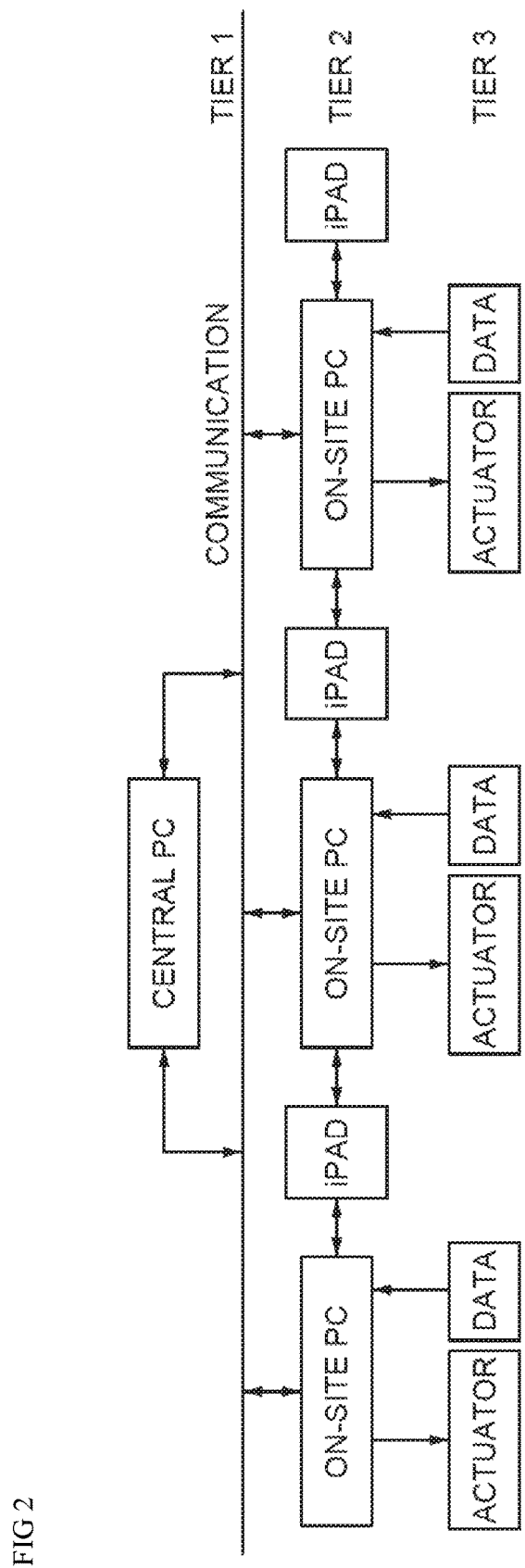
FIG. 2—Illustrates an exemplary and non-limiting embodiment of the environment management system 104

As illustrated in FIG. 2, environmental sensors ("actuator") sense environmental parameters and take in raw data ("data") from their respective system and location therein.

This data is then location and time stamped and sent to the on-site PC station ("on-site PC").

The raw sensor data can then be received at the on-site PC. Decision making data analysis may be done on the on-site PC, and/or at the central control center ("central PC"), and/or other network computers as well. The data received at the central PC is sent to the control center, and changes to the data can be made by the on-site PC in conjunction with the applicable system hardware.

Figure 3:
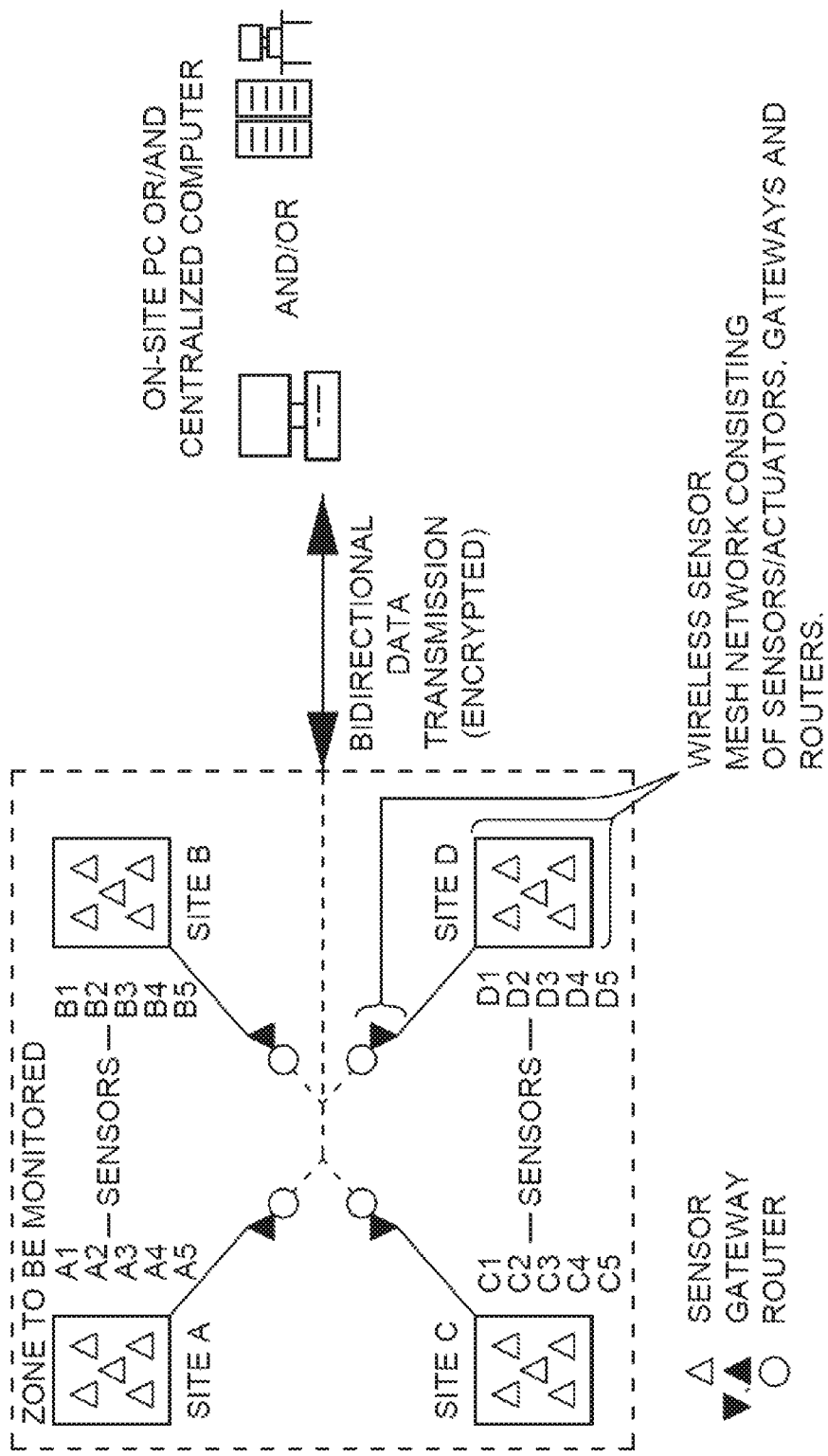
FIG. 3—Illustrates sensor-to-PC communication, a wireless mesh network of sensors can be employed that feedback to a centralized pc system.

In some embodiments, a wireless system of sensor-to-PC communication can be used. In some embodiments, as best illustrated in FIG. 3, a wireless mesh network of sensors can be employed that feedback to a centralized pc system.
The wireless system can contain at least three main components; intelligent sensors/actuators, wireless mesh network of routers and gateways with intelligent routing algorithms, and control and actuation.

In some embodiments, functionality and/or data associated with the environment management system 104 can include, but is not limited to, one or more of the following: number of plants put into veg (date, variety); assign lot and plant number; track development—ability to ascertain Inventory of plants at any given time; assign date of flowering (date flowering initiated, variety, lot #, plant #, location); track feeding schedule during flowering (date, six nutrient fields); track environmental conditions (linked to various sensors in the room: soil moisture, temperature, humidity, CO2 level, and Light intensity); cultivator notes field (Date, Note field for cultivator to make notes on specified date, i.e., 'lights were mistakenly left on form 0200 until 2300'); cannabinoid/terpenoid testing log (results, testing date, point in flowering); harvest (date, B&T weight); processing (trim date, weights); bulk packaging; transit; acquisition from MPC—lot #, variety, production reimbursement, total weight, form; receipt (entity, name, date); safety screening results (pass/fail)—molds, pesticides, aflatoxins, microbial; weighing; assembly (units); allocation information (amount, avg. allocation, reimbursement); and popularity indices (rank, velocity, potency/reimbursement—via cross-references with "Patient" data). Tables 23 and 24 illustrate exemplary and non-limiting embodiments of the cultivation-related information that can be collected.

Referring again to FIG. 1, the patient management system 106 can be configured to acquire patient data in any suitable manner. In some embodiments, the patient management system 106 can be configured to record patient data within the context of a method as illustrated in FIG. 1.

Tables 21 and 22 illustrate exemplary and non-limiting embodiments of the patient-related information that can be collected, including prescribing physician information.

In some embodiments, functionality and/or data associated with the patient management system 106 can include, but is not limited to, one or more of the following: standardized and compliance messaging to visitors (clients, elected officials, healthcare providers and media) by using recorded images/messages transmitted electronically via tablet (this can include all agreements and consents); collect biographical, contact, health history, and prior non-*cannabis* treatments electronically (currently collected on handwritten forms); set up patient record automatically; immediately upon completion of registration process, prior to first transaction; assign patient ID automatically and associate that ID with all future activities related to the patient; swipe driver's license upon subsequent visits—swipe can bring up patient's record and enable dispensary staffer to immediately see "attached" scans of physician recommendation, photo ID as well as recommendation expiration date; recommendation date can be color coded to quickly draw attention if out-of-date or if within X days of being out of date so that dispensary staffer can inform patient on the spot that either the recommendation is no longer valid or that it will be invalid in X days/weeks/months and that s/he should take steps to renew it; information regarding allocations to specific patient can be captured (date, variety, amount, $, lot) and accessible by staff by doing a patient "name" query; feedback regarding prior allocations can be captured (noted effects) and ratings of medicines; follow up, correspondence to physicians can be prepared automatically by pulling data from allocation database fields; the ability to query database by age, gender, strain, lot #, feedback (feedback itself and/or condition), etc. . . . and cross reference with production fields below; and the ability to predict/recommend medicine based upon prior ratings/preferences cross-referenced with strain chemistries.

System access can be a concern in such multiuser environments. Accordingly, embodiments directed to system access will be described with respect to the system 100, and unless explicitly stated otherwise, are understood to be directed to aspects of operation of the environment management system 104 (also referred to as the production side), and/or the patient management system 106 (also referred to as the patient side), and/or the computing apparatus 102. In some embodiments, system access (production side and patient side) can include four components of hierarchy; master administrator, regional manager, on-site manager, and cultivator (production side)/counselor (patient side). Communication structure can be cloned from one tier to the next, e.g. from cultivators to master administrators. In some embodiments, the communication structure can include alerts, decision tree confirmations, and/or other clearance restrictions-most restrictive at the cultivator level and least at the master control level. This 'overlapping' of communication in each sector can bring continuity between the chain of command so that major decisions are always cleared on multiple levels. Integrating with the on-site PC and individual PC can condition operation patients to use open communication that they know is backed by system-checked accountability.

The on-side PCs and the individual PCs can have a private communication system therebetween, such as encrypted IM and/or some form of closed/private network. In some embodiments, emails are encrypted for patients that can send notifications to users' email of choice when a new email arrives in their encrypted box.

PC Computer Terminal Interface
Master Administrator Platform:

In some embodiments, the master administrator platform (e.g. the central PC) can be characterized in the following exemplary and nonlimiting manner: access to all real-time databases, archived data sets/analysis results, patient information, cameras, etc. No access restrictions, access can be heavily encrypted and access codes can be very limited in number, only to key company patients for example. Access to certain aspects of the master platform can be partitioned off for limited access to other manager(s) if needed. For example, lab managers can have access to analysis data, certain production managers have access to some production data, etc.

Regional Manager Platform

In some embodiments, the regional manager platform allows for control over a number of sites, and over selected parameters that can be delegated by the master administrator platform. For example, the person responsible for formulating fertigation solutions in the lab can have regional access over the fertigation/soil water parameters, but not full 'master' access to all sites. This access can be restricted further to be allowed from on-site network computers.

Site Manager Platform

In some embodiments, the site manager platform (e.g. the on-site PC) provides an access point for data compilation/entry, Excel, Word, system specific software, and/or the like. System access/control will encompass control over master 'filtered' parameters such as fertigation time series/allocation and/or the like. Any independent changes made by the site manager either via their individual PC interface would be sent back to the necessary upper management in the form of an email, IM, and/or other chosen alert method. In some embodiments, a two method minimum, and preferably three alert methods are preferred for adequate redundancy and accountability.

In some embodiments, no cultivator/counselor access is permitted to on-site PCs or otherwise, and cultivator interaction can take place through the individual PC only. Counselor access will take place through a separate individual PC intended to provide product information to inform counselors and, through the counselors, consumers.

Individual PC Platform

The individual PC will serve different needs for different levels of management and operators, but the main purpose can be for use as a company specific interface and communication tool. At all levels users can populate, manage, and track their tasks, as well as enter data and notes. In some embodiments, all users can also send and receive messages to other users within their realm. At higher levels, users can track data trends, view real time data, and analyze various data components in different graph formats and analysis methods of their choosing. This analysis will tap data on the master database for all sites, allowing regional manager and master administrators to track multiple site data from one device.

The level of interaction at each level can happen via applications in some embodiments, some shared by all users and others only for those with special permissions. A majority of these applications can be specific need-based adaptations of preexisting native apps (i.e.: notepad) or proprietary apps.

Master Access platform: Data input for all areas of production and/or patient side. In some embodiments, the master access platform allows viewing of each site(s) critical data 'at a glance'. The 'at-a-glance' data can be changed in both content and form. For example, one patient may want to compile yield data for all sites that are displayed in a monthly time series linear graphs over a prior year, with a year-to-date production trend graph for comparison (underlined portions represent changeable variables in the at-a-glance screen). Any analysis done by algorithms could also be accessible at the individual PC level, but not necessarily as in depth as is available at the on-site PC level. In some embodiments, the master access platform includes the ability to make changes/overrides that update to selected individual PCs (i.e. a master access change to nighttime temperature schedule for a certain cell would send notifications of the change, if desired, and create a permanent change). In some embodiments, the master access parameter set points, and other system parameter elements that are outside of the regional manager/site manger security clearance will require an encrypted password to change. If needed, this would allow master administrators to grant lower management access to certain elements on per case basis.

In some embodiments, the master access platform includes the ability to access patient records, surveys, survey group data, blood sample data, and all other aspects of the patient side of the system. At-a-glace home screen for patient data will have the ability to show output of algorithmic data mining. A patient system example would be when a patient's makes their first visit and submits their information into the patient database, that information is cross-referenced with an array of other patient 'data points' (such as ailment, age, gender, survey responses, chemovar preference, etc.). Based on the results of one or a few simple data mining algorithms, tailored recommendations can be made and generated on the counselor's individual PC in real time (e.g. a recommendation engine can be implemented).

In some embodiments, the master administrator platform can include the ability to set the recommendation parameters for the algorithm's decision process, but whatever chemovar recommendation parameters are chosen, in some embodiments, they can remain constant for all new patients. In this manner, a consistent reliable database can be built over time, which will increase the 'accuracy' of the system. This ability for the system to 'learn' using AI (artificial intelligence) software programming, likely with evolutionary algorithms, will require a certain amount of time of patient response data to be entered before the programs(s) can discern which decision pattern yields the favorable result a statistically significant amount of times. The eventual result of this system component at the patient/counselor interaction level can be an accountable and consistent decision tree process that is tied in to all levels of management, removing counselor recommendation variance from one to the other and possible misinformation. Although this example pertains to chemovar recommendation, it is understood that it can also be applied to other patient/counselor interactions such as patient/POA (point of allocation) and others.

Regional Manager Platform: The individual PC regional manager platform can allow RMs to have at-a-glance data viewing/comparison capabilities similar in function to that of the master administrator, but restricted in content to that which is job/project related or delegated otherwise. Data input/analysis and system monitoring can be the main use of the individual PC for RMs. Selective control over certain 'master delegated' system parameters could be altered by RMs via the individual PCs similar to the way it would be on the on-site PC, but via a comparatively 'deconstructed/refined' tablet interface.

Site Manager Platform: Can allow for site overview and management of multiple cultivators or cultivation teams.

Cultivator/Counselor platform: Can allows for cultivator notes to be entered into the system, and the system can digitally 'tag' the notes with date, time, batch number, plant number, etc. in the system to be referenced at a later point if needed. Cultivators will need to have fields in the notation application that will be filled out with the appropriate information to create a track record for the entry tag.

Having described system access, referring again to FIG. 1, embodiments directed to software tools will be described with respect to the system 100, and unless explicitly stated otherwise, are understood to be directed to aspects of operation of the environment management system 104 (also referred to as the production side), and/or the patient management system 106 (also referred to as the patient side), and/or the computing apparatus 102.

Decision Tree Analysis Help Tool—

Designed with the cultivator/counselor in mind, this application can serve both as a communication pathway between managers and cultivators/counselors as well as a help tool for them as well. A troubleshooting function is in the form of a series of searchable common issues that arise either in daily procedure or possibly on rare occasions. If such an issue arises that someone doesn't know the correct flow of action for a particular task, they can reference this application to see a decision tree/flow chart on how it should be done according to management.

This application can become a communication tool when the managers, whether transitory regional or permanent on-site, choose to upload decision trees into the system. For example, if a regional manager comes through and makes changes to operating procedure or wants to reiterate procedure, they can quickly create a simple decision tree chart (possibly pre-formatted entry fields) while on-site and upload that system onto the network. Once uploaded, it is available for others to view when needed, and managers could even make it into a checklist format in which operators must check off steps in the process until proficient.

Data Entry Portal—

The data entry portal can be the data entry application for the individual PC that will have different 'forms' for different operator positions. For example, patient-based entry fields (i.e.: POA data, patient feedback data, etc.) for counselors and plant-based entry fields (i.e.: plant number, lot number, package number, etc.) for cultivators.

Data Analysis Tool—

The data analysis tool can allow managers and technicians the ability to alter their at-a-glance home screens and run other analysis on their data in the field. The range of this analysis can be limited in comparison to the pc interface. The results of such an informatics system can be directed and displayed in many ways, to be chosen by the user.

Genetics—Terpene Profiles—

System is designed to analyze, characterize and codify the subtleties in terpene differences across a large number of separate genetic groups (as per the color coded system), different populations within those groups, and time series analysis tracking where applicable (i.e.: terpene ratio and/or quantity variation during final weeks of flower development). Individuals will be grouped into different color groups based initially on some qualitative characteristics such as 'nose' (piney, fruity, etc.), and later quantitatively. Quantitative analysis will allow for each individual to be profiled into the database.

Chemotype Profiles—

These can have the same framework as the terpene program, but can include cannabinoids and other secondary metabolites of interest.

Bioinformatics—

The use of evolutionary algorithms to run computer models of mass breeding programs that can allow for increased efficiency in parent material selection as well as accurately estimating required population sizes for field trials.

Algorithms for Data, Systems and Decision Making—

Numerous algorithms can be used at any point either singularly, simultaneously or in conjunction to produce new data, maintain system functionality and/or optimization, compilation and execution of fuzzy control programs, analyzing and/or processing data, making system updates and 'intelligent' decision/changes, and monitoring system components/sensors to name a few. Some of the algorithms used to address dynamic data sets and problems can include, but are not limited to; least squares algorithms, direct and/or indirect control evolutionary algorithms, pattern recognition algorithms, data fusion and/or data clustering algorithms.

Referring to FIG. 1 again, the computing apparatus 102 (also referred to as the "central computer", the "central PC", etc. See FIGS. 2 and 3) can handle the acquisition, processing, and analysis of data from different components of the system 100, including the environment management system 104 and the patient management system 106. In some embodiments, the computing apparatus 102 can be configured to track both crop and patient trials of chemotypes of potential interest. For example, the computing apparatus 102 can be configured to track the production of metabolites of interest in a crop, while also being configured to track the metabolism of those eventual plant-produced metabolites as they are metabolized by consumers. Thus, active ingredients can be tracked from their concentrations on the plant in the field, through production and processing, to the eventual concentrations as metabolites in the blood of patients, post consumption. In this manner, aspects of operation of the computing apparatus 102 can define the complete chemical relationship between plant and human. In some embodiments, this defined chemical relationship can be used to create maps, multi-dimensional scatter plot to examine and/or analyze patterns within a host of metabolic variables throughout the incredibly complex system.

In some embodiments, once data is received at the computing apparatus 102 any number of actions can be taken, based on a user's needs and based on a user's associated system access parameters as discussed above (i.e. a user of the computing apparatus 102, of the environment management system 104, and/or of the patient management system 106). In some embodiments, the computing apparatus 102 can be configured to implement one or more algorithms to analyze various types and forms of information including, but not limited to; genetic data, breeding data, tissue culture data, field trial data, all computer system-related data, greenhouse data, indoor grow data, environmental sensor-sourced data, environmental data from other sources, all patient-related/sourced data, allocation/reimbursement data, and all other types/forms of proprietary sourced data.

The resulting information can then be transmitted back to the user that requested it in the form of their choosing via bidirectional data transmission. This transmission, either wireless or wired in signal, can be routed through the network (not shown), and/or can be encrypted. The user can then choose to make changes or updates to the controllable/accessible aspects of the system 100, if applicable. For any alterations to system parameters or any other significant system aspect, a feedback system can exist for alerts, timestamps, updates to current/future computational processes, referenced data sets, and other signals.

In this manner, patient feedback data can fuel the production of medicines. For example, the patient feedback data can be used to optimize pharmacologically active plant oil content through a host of breeding and cultivation techniques. In some embodiments, the computing apparatus 104 can be configured to monitor market trends and identifies products' appeal, efficacy, and sell-through as the products' chemotype evolves over time refined by consumer feedback and research studies. In some embodiments, the feedstock that is used to create these products can be selected in response to real-time feedback collected by this system from consumers. The coupling of chemotype development and selection with consumer feedback can enable the identification of market trends of selected chemotypes at the earliest possible stage in product deployment. For example, principal component analysis can be used to identify synergies between groups of pharmacologically active constituents that are gaining traction with consumers for their medicinal effectiveness, their aesthetic appeal or combination of both.

TABLE 21

Exemplary patient table patient collective (list) (relates to Collective Table)
patient join date (xx/xx/xx)
patient referred-by last name
patient referred-by first name
patient last name
patient first name
patient street name and number
patient address designation: avenue/drive/street/none
patient birthdate (xx/xx/xxxx)
patient apartment number up to 4 digits)
patient zip code (5 digit)
patient home phone (10 digit)
patient cell phone (10 digit)
patient scanned id (yes/no)
patient recommendation date (xx/xx/xxxx)
patient recommendation scanned attachment (yes/no)
patient state id card date (xx/xx/xxxx)
patient recommending physician last name (relates to Recommending Physician Table)
patient recommending physician first name (relates to Recommending Physician Table)
patient consent to share data with physician (yes/no)
patient consent to share data with physician scanned attachment (yes/no)
patient condition 1
patient condition 1 prior treatment medication (list?)
patient condition 1 prior treatment medication feedback (ranking)
patient condition 2
patient condition 2 prior treatment medication (list?)
patient condition 2 prior treatment medication feedback (ranking)
patient condition 3
patient condition 3 prior treatment medication (list?)
patient condition 3 prior treatment medication feedback (ranking)
patient cannabis experience (list)
patient unit allocation date (xx/xx/xxxx)
patient unit allocation date
patient unit allocation date quantity (standard unit measurement?)
patient unit allocation date feedback (survey) (correlate to prior treatment medication feedback)
patient unit allocation date feedback survey date (xx/xx/xxxx)

TABLE 22

Exemplary Recommending Physician Table recommending physician last name (relates to Patient Table)
recommending physician first name (relates to Patient Table)
recommending physician street name and number
recommending physician address designation: avenue/drive/street/none
recommending patient suite number up to 4 digits)
recommending physician zip code (5 digit)
recommending physician business phone (10 digit)
recommending physician business name
Condition Table(s) . . .

TABLE 23

Exemplary Lot Table lot identifier (relates to Collective Table and Patient Table)
lot location identifier
lot plant identifier (relates to Plant Table)
lot date began veg
lot date began flowering
lot feeding date(s)
lot feeding date(s) nutrients (six fields)
lot environmental condition(s) (dates) (soil moisture, temperature, humidity, CO2, light intensity)
lot cultivator notes
lot cannabinoid/terpenoid testing (results, testing date, point in flowering)
lot safety screening results (pass/fail)
lot harvest date

TABLE 23-continued

Exemplary Lot Table lot harvest date weight
lot trim date
lot trim date weight
lot bulk packaging date
lot bulk packaging date weight
lot transit departure date/time
Plant Table(s) . . .

TABLE 24

Exemplary Collective Table collective lot arrival date/time
collective lot identifier (relates to Lot Table)
collective break lot up into units date
collective units inventory
patient unit allocation date
patient unit allocation identifier
patient unit allocation reimbursement
Seed to Plasma Constituent Analysis Example 11. Multiplexed *Cannabis* Medicines To make multiplexed *cannabis* medicines that are designed to be effective in a particular disease or disorder, base extracts which have not undergone much manipulation are mixed with stock fortifying extracts that have undergone extensive manipulation. These mixtures provide stocks of materials that are rich in either THC, CBD, CBG, limonene, pinene, myrcene, linalool, beta-caryophyllene, phytol, terpinolene, terpenene, ocimene, caryophyllene oxide, or alpha-humulene or a combination thereof.

Any means commonly used in the art to isolate particular *cannabis* agents may be used may be used to prepare the fortifier stocks. For example, stock cannabinoid fortifiers with high THC (I), CBD (II), and/or CBG (IV) contents, are produced by removing the extract from phenotype I, II, or IV plants that are high in THC, CBD, and/or CBG. The terpenes are distilled from the extract by supercritical extraction to provide a crude sludge, which is then winterized to remove waxes.

To prepare the high terpene (EO) fortifiers, plants are produced that have the desired concentrations of terpenes: these include, but are not limited to, limonene, pinene, myrcene, linalool, beta-caryophyllene, and/or phytol. The high terpene extract is removed from the plants, and is then steam distilled to provide stock terpene fortifiers with high limonene (L), pinene (P), myrcene (M), Linalool (Lo), caryophyllene(C), and/or phytol (P). Since these compounds may extract together it might be necessary to fractionally distill the crude to further enrich for the desired compound.

The *cannabis* base to which the high cannabinoid or terpene fortified stock is added is prepared from any and all of the various strains described herein, or others known in the art, by supercritical extraction. This provides the foundation cannabinoid ratio which retains the subjective qualities of the strain since all the cannabinoids, terpenes, and waxes are still present.

Figure 4:
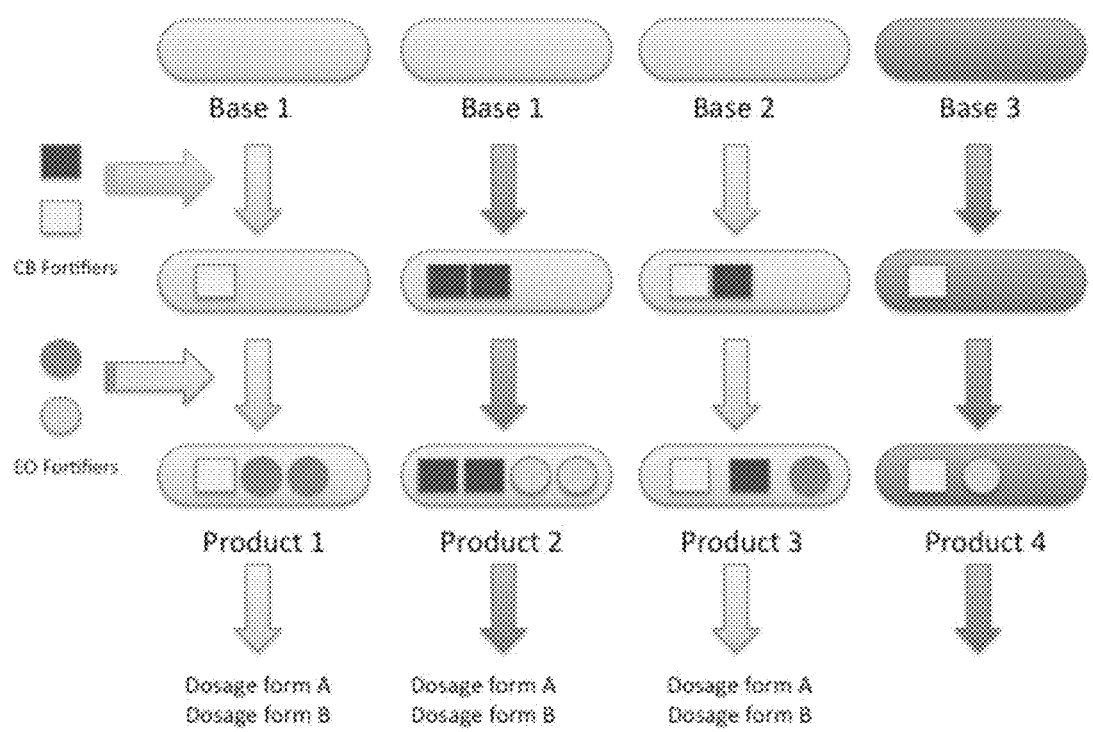
FIG. 4—Illustrates multiplexed *cannabis* medicines.

The concentrations of the various active agents present in the multiplexed *cannabis* medicine will vary depending on what has been determined to be the optimal dosing for any particular disease or disorder being treated. Depending on the condition being treated and the subjective qualities desired, the base is then fortified with high cannabinoid and/or terpene stock to give the final preparation according to the FIG. 4.

Examples of some mixtures that have therapeutic benefit are OG-(I)L (OG with THC and limonene fortifiers), OG-(I)LP (OG with THC, limonene, and pinene fortifiers), OMRA-(II)C (OMRA with CBD and caryophyllene fortifiers), and JJxA-(IV)Lo (JJxA with CBG and linalool fortifiers).

Example 12. Dosing Regimens of Multiplexed *Cannabis* Medicines

Patients

Regardless of the condition being treated, two separate groups of patients are evaluated: one composed of novice *cannabis* users and one composed of experienced *cannabis* users. It is important to know the past *cannabis* use history of patients since tolerance can occur in experienced users, who will therefore experience the therapeutic effects of the multiplexed *cannabis* formulation differently than those with no tolerance. However the rate and duration of tolerance varies with the different effects; a particular individual may have developed tolerance to one *cannabis* agent but not to another. This may actually serve to increase the therapeutic margin depending on the condition. For instance, tolerance to cognitive and psychomotor impairment, the psychological high, tachycardia, and orthostatic hypertension, tends to develop rather quickly and chronic users may not experience these detrimental side effects, while still benefitting from the analgesic or other therapeutic effects of *cannabis*. Conversely, the novice user who has no tolerance, can be slowly subjected to dose escalation (e.g. over 30 days or more) to build tolerance to these effects before given therapeutic doses. Many times the dysphoria experienced by naive users is enough to cause discontinuation of the treatment, and slow dose escalation which helps induce tolerance to the detrimental side effects may alleviate this.

The biodistribution and PK of the *cannabis* active agents administered either orally or through inhalation differ substantially. An acute condition may respond better to an inhaled formulation while a chronic condition may respond better to the prolonged plasma concentrations resulting from oral administration. The higher levels of 11-OH-THC (and presumably CBD) formed from first-pass metabolism after oral formulation administration, which is more potent and has better blood brain barrier penetration than the parent compound, has implications for neurological conditions. The dosing studies described herein evaluate the effects of various doses of the multiplexed *cannabis* formulations when administered either orally or through inhalation.

Formulations

The amounts and types of bases, cannabinoid and terpene fortifiers are designed to have a synergistic effect on the conditions being treated. The multiplexed signaling resulting from the synergy of the components may be more effective than any single component alone and are tailored to achieve the desired effects. For instance, analgesia has been shown to be mediated by the $CB_1$, $CB_2$, TRPV-1, and $\alpha_2$-AR receptors, which suggests a component mixture of THC (which acts on $CB_1$ and $CB_2$), TRPV-1 (which acts on CBD), CBG (which acts on $\alpha_2$-AR) and $\beta$-myrcene (which acts on $\alpha_2$-AR) will be therapeutic. Similarly if the cause of the pain is inflammation, which is mediated by TNF-$\alpha$ and PGE-1, then the synergistic effects of a multiplexed medicine comprising CBD-rich extract, which counteracts TNF-$\alpha$ and $\alpha$-pinene, which counteracts PGE-1, proves a more effective therapeutic than extracts not containing both of these compounds. The following Table 25 shows a few examples of the various clinical indications that are treated with *cannabis* formulations, the cannabinoids and terpenoids that are effective therapeutics for each clinical indication, and the pathways each cannabinoid influences.

TABLE 25

Clinical indications that can be treated with *cannabis* formulations.

| Pharmacological Action / Relevant Clinical Indication | Cannabinoid | | | | | | Terpene | | | | |
|---|---|---|---|---|---|---|---|---|---|---|---|
| | THC | CBD | CBG | CBC | CBN | THCV | Limonene | a-pinene | b-myrcene | Linalool | b-caryophyl. |
| Neuroprotective | | | | | | | | | | | |
| Parkinson's | ✓ | ✓ | | | | | | | | | |
| Alzheimer's | Down regulate glutamate | Down regulate [Ca2+] | | | | | | | | | |
| MS | Down regulate [Ca2+] | Down regulate ROS | | | | | | | | | |
| Stroke | anti-oxidant | anti-oxidant | | | | | | | | | |
| Vasorelaxant | | | | | | | | | | | |
| Glaucoma | ✓ (+)PPARg | ✓ (+)PPARg | | | | | | | | | |
| Appetite Stimulant | | | | | | | | | | | |
| Anorexia | ✓ | | | | | | | | | | |
| Cachexia | Down regulate leptin | | | | | | | | | | |
| AIDS wasting | (+)PPARg | | | | | | | | | | |
| Anti-proliferative | (−)TRPM8 | ✓ up[Ca2+] up-ROS (+)CB₂ (−)TRPM8 | ✓ (−)TRPM8 | ✓ (−)TRPM8 | ✓ | | | | | | |
| Intestinal Anti-prokinetic | | | | | | | | | | | |
| Diarrhea | ✓ | (−)Ca₁ Down regulate FAAH | | | | | | | | | |
| Immunosuppressive | | | | | | | | | | | |
| Allergies | Down regulate T-Cells | Down regulate T-Cells | | | | | | | | | |
| MS | Down regulate Cytokines | | | | | | | | | | |
| RA | Down regulate Interleukins | | | | | | | | | | |
| IBS | ✓ | | | | ✓ | | | | | | |
| Anti-Inflammatory | | | | | | | | | | | |
| Pain | ✓ Down regulate IFNg | ✓ Down regulate TNFa | | ✓ (+)TRPA1 | | | | ✓ PGE1 | ✓ PGE2 | | ✓ PGE1 |
| MS | Down regulate Interleukins | Down regulate ADO uptake | | | | | | | | ✓ | |
| Chron's Arthritis | (+)PPARg | | | | | | | | | | |
| Sedative | | | | | | | | | | | |
| Sleep disorders | ✓ | ✓ | | | | | | | | ✓ | |

TABLE 25-continued

Clinical indications that can be treated with cannabis formulations.

| | Cannabinoid | | | | | | Terpene | | | | |
|---|---|---|---|---|---|---|---|---|---|---|---|
| | THC | CBD | CBG | CBC | CBN | THCV | Limonene | a-pinene | b-myrcene | Linalool | b-caryophyl. |
| Anti-epileptic | | | | | | | | | | | |
| Epilepsy | ✓ | ✓ Down regulate [Ca2+] (+)5HT$_{1A}$ | ✓ Down regulate GABA uptake | | | ✓ (−)CB$_1$ Down regulate GABA | | | | ✓ anti-Glu | |
| Anti-emetic | | | | | | | | | | | |
| CIE | ✓ | Down regulate ADO uptake ✓ | | | | | | | | | |
| Anxiolytic | | | | | | | | | | | |
| Panic Disorder | ✓ | (+)5HT$_{1A}$ | Down regulate GABA uptake | | | | 5HT$_{1A}$ | | | ✓ | |
| Social Anxiety Disorder | | | | | | | | | | | |
| Generalized Anxiety Disorder | | | | | | | | | | | |
| PTSD | | | | | | | | | | | |
| Antidepressant | | | | | | | | | | | |
| Depression | ✓ | ✓ | (−)5HT$_{1A}$ | | | | ✓ | | | | |
| Anti-psychotic | ✓ | (+)TRPV1 ✓ | | | | | | | | | |
| Anti-spasmodic | | | | | | | | | | | |
| MS | ✓ | | Down regulate GABA uptake | | | | | | | | |
| Spinal cord injury | | | | | | | | | | | |
| Cerebral palsy | | | | | | | | | | | |
| Analgesic | | | | | | | | | | | |
| MS | ✓ CB$_1$ CB$_2$ (+)TRPA1 | ✓ (+)TRPV1 (+)TRPA1 | ✓ (+)TRPA1 (+)TRPA1 Down regulate GABA uptake a2 blockade | ✓ (+)TRPA1 | ✓ (+)TRPV2 | | | | ✓ | ✓ A$_{2A}$ | |
| Post-operative pain | | | | | | | | | | | |
| Migraine | | | | | | | | | | | |
| Neuropathic pain | | | | | | | | | ✓ | | | |
| Sciatica | | | | | | | | | | | |
| Bronchodialator | | | | | | | | | | | |
| Asthma | ✓ | | | | | | | | | | |
| Sleep-related breathing disorders | | | | | | | | | | | |
| Muscle relaxant | | | | | | | | | | | |
| MS | ✓ | | ✓ Down regulate GABA uptake | | | | | | | | |

The fortifiers of the present invention are chosen to reinforce the treatment for the given clinical condition and to posses an improved therapeutic margin, through synergy of the various pathways involved in the disease or disorder. The above Table 25 is a very brief, and by no means complete, summary of pharmacological effects of the various cannabinoids and terpenoids along with the relevant therapeutic applications. In cases where a mechanism has been proposed this has been included in the table.

Patient Sub-Groups and Controls

Large patient groups (75-100 patients) are studied to evaluate the subjective effects of the *cannabis* formulations. For all studies, patient groups are chosen from several locations and are chosen from various dispensaries and/or solicited, if drug-naïve patients are difficult to find. These patients are subdivided into experienced and novice *cannabis* users, and then if the clinical indication warrants it, further subdivided into those receiving either the oral and inhaled formulations. Due to the extremely variable bioavailability, dosage regimens are tailored to the indication and the patient. All studies are done with the appropriate medical and/or psychological supervision and evaluation. There are several placebo groups, with the patients receiving either complete placebos, a placebo containing no cannabinoids and only terpenes, and placebos containing no terpenes and only cannabinoids. This will serve to establish not only efficacy of the cannabinoids and/or terpenes, but also the synergy. The complete placebo is generated from fats and waxes resulting from cannabinoid extraction and is spiked with terpenes fortifiers for exact and reproducible levels of terpenes to make the placebo without cannabinoids, or it is spiked with cannabinoid fortifiers to make exact and reproducible levels of cannabinoids without the terpenes.

Proposed Clinical Indications

The studies first evaluate the predictable and reproducible plasma levels of *cannabis* active agents both in a patient, and between different patients, who received the multiplexed medicines either orally or through inhalation. Once this is evaluated, the mitigation of adverse effects is studied through dose escalation and/or examining the ratios of active ingredients in the multiplexed *cannabis* formulation. Once this is established, the various clinical indications are examined.

Based on proposed pharmacological mechanisms of action, there are a number of clinical indications that are evaluated for treatment with *cannabis*-based medicines. These include, but are not limited to, Parkinson's, Alzheimer's, MS, stroke, glaucoma, anorexia, cachexia (from AIDS, cancer, Multiple Sclerosis, congestive heart failure), diarrhea, allergies, arthritis, irritable bowel syndrome, Crohn's disease, sleep disorders, epilepsy, chemotherapy induced emesis, panic disorder, social anxiety disorder, generalized anxiety disorder, post-traumatic stress disorder, depression, spinal cord injury, cerebral palsy, post-operative pain, migraine, neuropathic pain, sciatica, asthma, and/or sleep-related breathing disorders.

Terminology

In the studies below, the medicines are referred to by the principal components of the base and fortifiers.

Study 1: Precision of Dosing Regimens and Bioavailability

Traditionally, administration of *cannabis* has resulted in unpredictable bioavailabilities, resulting in frequent occurrences of overdosing and/or underdosing which make it difficult to attain therapeutic blood levels while mitigating adverse events in a predictable manner. Therefore, the ability to provide predictable and consistent blood plasma levels has great utility.

In this study, patients are divided into two groups: one receiving inhaled *cannabis* formulations, and one receiving oral *cannabis* formulations. Those receiving the oral dose of *cannabis* abide by strict pre-dosing dieting. The dose amount is scaled to body weight (0.05 and 0.1 mg/kg) and, since *cannabis* active components are highly lipophillic, the dose amount further scaled based on BMI and/or body fat measurements. For example, the dose based on body weight can be multiplied based on the patient's BMI (e.g. multiplying the dose by 0.9 for BMI <18, 1.0 for BMI=18-25, 1.1 for BMI 25-30, and 1.3 for BMI>30). Each study is performed in triplicate to determine intra-patient variability and each patient first undergoes i.v. dosing with the prescribed amount of drug. The oral formulation is given in a single dose, and to minimize the effect of smoking characteristics, the inhaled formulation is given in tabs of sufficient size to be vaporized and administered in a single dose. Alternatively, the tabs to be vaporized are subdivided into "unit sizes" that are administered in rapid succession. Blood samples are taken at various intervals and assayed for the *cannabis* active agent as well as the appropriate metabolites. From the data biodistribution and appropriate PK parameters are determined.

Study 2: Mitigation of Adverse Effects

This study establishes the development of tolerance to the possible adverse effects of *cannabis*, such as cognitive and psychomotor impairment, the psychological high, anxiety, and tachycardia. This is important as many times the therapeutic dose approaches the intoxicating dose and may cause discontinuation of treatment. Only inhaled formulations are employed in this study since the onset of the drug effect is rapid and the duration is shorter, which provides easier monitoring. Inhalation of the drug formulation is preferably done with a volcano, timed inhalations, timed 10-second breath-holds, and/or timed intermediate duration. Subjective questionnaires and heart-rate monitoring are used for evaluation.

The subjects are divided into a number of groups, and are administered either complete placebo, placebo with only terpenes, THC base, THC:CBD base, or THC base with varying levels and combinations of CBD, CBG, limonene, and/or linalool fortifiers, all of which are suggested to alleviate anxiety. The subjects are administered with 3 mg, 6 mg, or 12 mg of the drug formulation (or dosage levels determined from Study 1). The subjects are further subdivided into those who are administered the maximum dose at the first treatment and those who undergo a slow dose escalation. This establishes the proper dosing regimens and ratios of anxiolytic ingredients in the multiplexed formulations if adverse events are noted in future studies.

Study 3: Pain

Patients are grouped into those suffering from Multiple Sclerosis, post-operative pain, migraine, arthritis, and neuropathic pain (such as sciatica) and then subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered with the placebos, THC base, THC/CBD base, or various amounts of CBD, CBG, myrcene, and/or linalool fortifiers, all of which have been implicated in analgesia. Patients are evaluated via questionnaire and/or medical examination.

Study 4: Anxiety

Patients are grouped into those suffering from generalized anxiety disorder (GAD), seasonal affective disorder (SAD), panic disorder, and post-traumatic stress disorder (PTSD). Patients are subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients with SAD receive a lower dosing regimen. Patients are administered either the placebos, THC base, THC/CBD base, or various amounts of CBD, CBG, limonene, and/or linalool fortifiers, all of which have been suggested to relieve anxiety. Patients are evaluated via questionnaire and/or psychological examination.

Study 5: Depression

Patients are subdivided into those receiving either oral (2.5 mg and 5 mg THC) or inhaled (2.5 mg and 5 mg THC) administration routes. Dosage levels can also be determined based on Study 1. In this study, higher doses are not examined since only low doses of *cannabis* have been implicated in relieving depression. Patients are administered either the placebos, THC base, THC/CBD base, or various amounts of CBD, CBG, and/or limonene, all of which have been suggested to relieve depression. Patients are evaluated via questionnaire and/or psychological examination.

Study 6: Allergies, Rheumatoid Arthritis, Irritable Bowel Syndrome, Pain, MS, Crohn's Disease, Arthritis Patients are grouped into those suffering from allergies, rheumatoid arthritis, irritable bowel syndrome, pain, MS, Crohn's disease, and arthritis and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base, or various amounts of CBD, pinene, myrcene, and/or beta-caryophyllene fortifiers, all of which have been suggested to be inhibit pro-inflammatory and immune response pathways. Patients are evaluated via questionnaire and/or medical examination.

Study 7: Asthma, Sleep Disorders, and Sleep Apnea

Patients are grouped into those suffering from mild asthma, central sleep apnea, and obstructive sleep apnea and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base, or various amounts of pinene, which has been implicated in bronchodillation and of myrcene and linalool, which have been suggested to be sedatives. Patients are evaluated via questionnaire and/or medical examination.

Study 8: Appetite Stimulant

Patients are grouped into those suffering from anorexia, AIDS Wasting Syndrome, and cachexia resulting from MS or CHF and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base, limonene or pinene for associated anxiety, and CBG, or limonene for associated depression. Patients are evaluated via questionnaire and/or medical examination.

Study 9: Neuroprotection

Patients are grouped into those suffering from mild Parkinson's, Alzheimer's, Multiple Sclerosis, and possible recent stroke and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base, limonene or pinene for associated anxiety, and CBG or limonene for associated depression. Patients are evaluated via questionnaire and/or medical examination.

Study 10: Multiple Sclerosis

Patients are subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base, or various ratios of THC fortifiers (associated with neuro-protective, immunosuppressive, anti-inflammatory, anti-spasmodic, analgesic, and muscle relaxant effects), CBD fortifiers (associated with neuro-protective, immunosuppressive, anti-inflammatory, anti-spasmodic, and analgesic effects), CBG fortifiers (associated with anti-spasmodic, analgesic, and muscle-relaxant effects), pinene (associated with anti-inflammatory effects), myrcene (associated with anti-inflammatory and analgesic effects), linalool (associated with analgesic effects), and beta-caryophyllene (associated with anti-inflammatory effects). Patients are evaluated via questionnaire and/or medical examination.

Study 11: Epilepsy/Migraine

Patients are grouped into those suffering from seizure disorders of different classifications and migraine headaches of different classifications, and subdivided into those receiving either oral (2 mg, 5 mg, 10 mg, 15 mg, 20 mg THC) or inhaled (2 mg, 5 mg, 10 mg, 15 mg, 20 mg THC) administration routes. Dosage levels can also be determined based on Study 1. Patients are administered either the placebos, THC base, THC/CBD base and CBD, CBG, or linalool fortifiers, all of which are implicated in anti-epileptic pathways. Patients are evaluated via questionnaire and/or medical examination.

Example 13. Zero-Point Delivery Device and Principles

Vaporization is the process of heating a substance to its boiling point to release vapor containing the active constituents in a gaseous state. This vapor can be inhaled to deliver the active agents in the drug, but without the harmful irritants and carcinogens found in smoke that results from combustion of the plant material, and without the alcohol and preserved water that serves as a base for nebulizer solutions. There is a need for a convenient handheld and/or tabletop vaporization device that vaporizes designer 'sludges' (i.e. material to be vaporized) that are created with predetermined and calculated resistances to work best with the vaporization device. The internal resistance of the sludge, in concert with the high voltage current and the aluminum dosage strip technology described in the next Example below, generates the necessary heat of vaporization to volatilize all of the active components in the sludge.

The vaporization device requires, at its most basic, a source of heat that is emitted when an electric current is passed through a wire or a fluid, and a dosage strip containing the *cannabis* sludge to be vaporized that has been optimized for consumption in the vaporization device. The design of the delivery device comprises components that are similar to that of a basic taser or stun gun, which have been used in the laboratory to vaporize *cannabis* oils or sludges. An example of a sample taser design is shown.

At its simplest, the ergo-dynamic vaporization device described herein comprises a space for depositing the dosage strip, a dose selector switch, a micro-computer which activates any one or more four activation sites present on the dosing strip, an activation switch, a battery, a speaker, a LED light, and an area through which the patient inhales the vapor.

Figure 5:
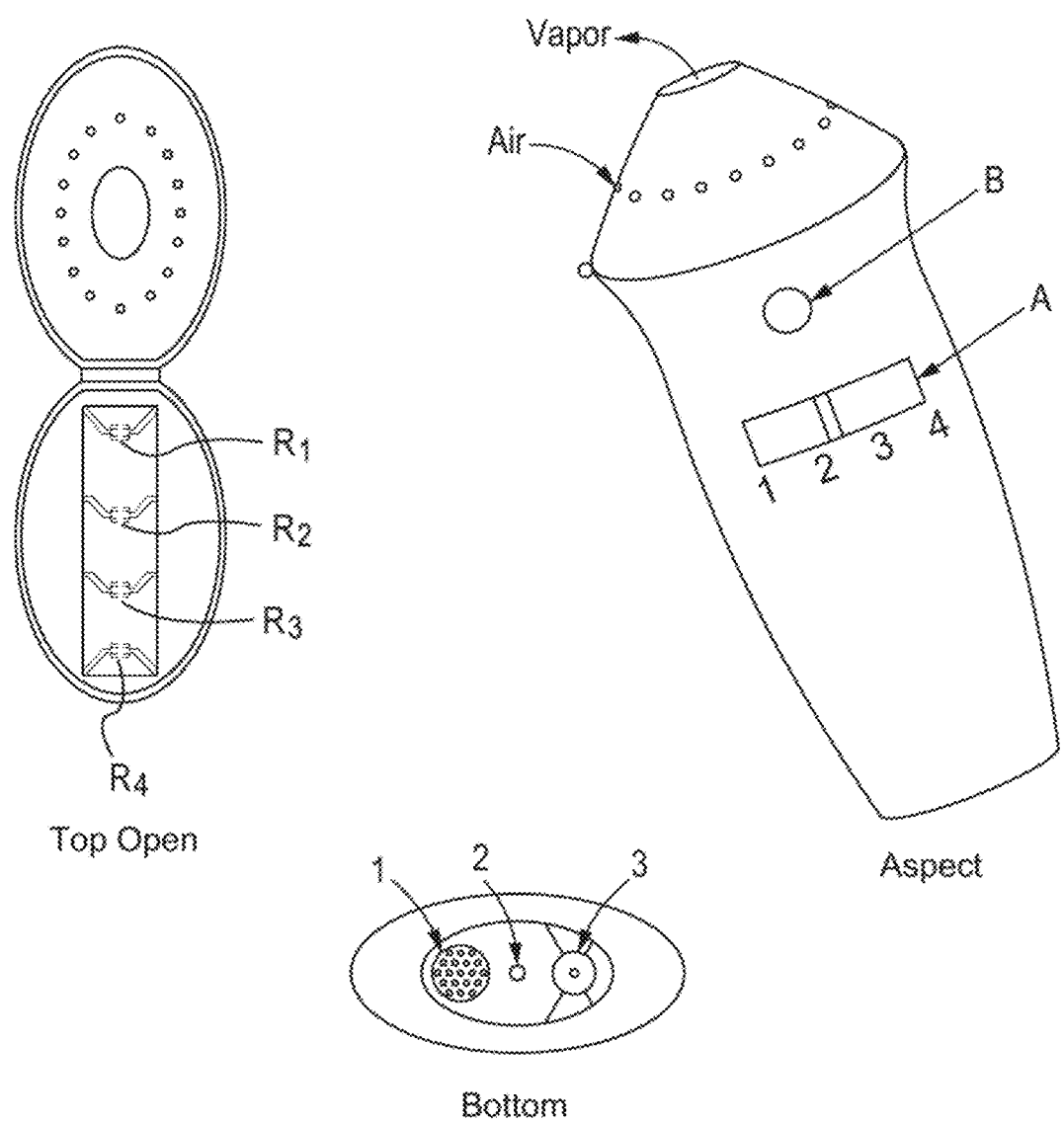
FIG. 5—Example of one manifestation of the vaporizer device.

An example of one manifestation of the vaporizer device is shown in FIG. 5.

The patient chooses the proper dosage on the dose selector switch, and pushes the activation switch, thereby delivering a high voltage current through the aluminum electrodes on the dosage strip to heat and vaporize the sludge. Intake air passes in through small holes located around the central mouth piece. This air flow creates an upward current that allows the essential oil vapor to be inhaled.

The vaporizer may also comprise a selector switch which is designed to select the desired *cannabis* dosage. This switch communicates with the microchip to control how many of the activation sites on the dosing strip are activated and activates the activation sites in any possible combination. In non-limiting examples, the switch activates each of the four sites individually, one, two, three or four of the sites consecutively or serially, or one, two, three, or four sites with a delay between them. The orders in which the activation sites are activated, and/or the delay between the activation of one or more sites, are calculated based on dosage studies.

Example 14. Zero-Point Delivery Doses

Figure 6:
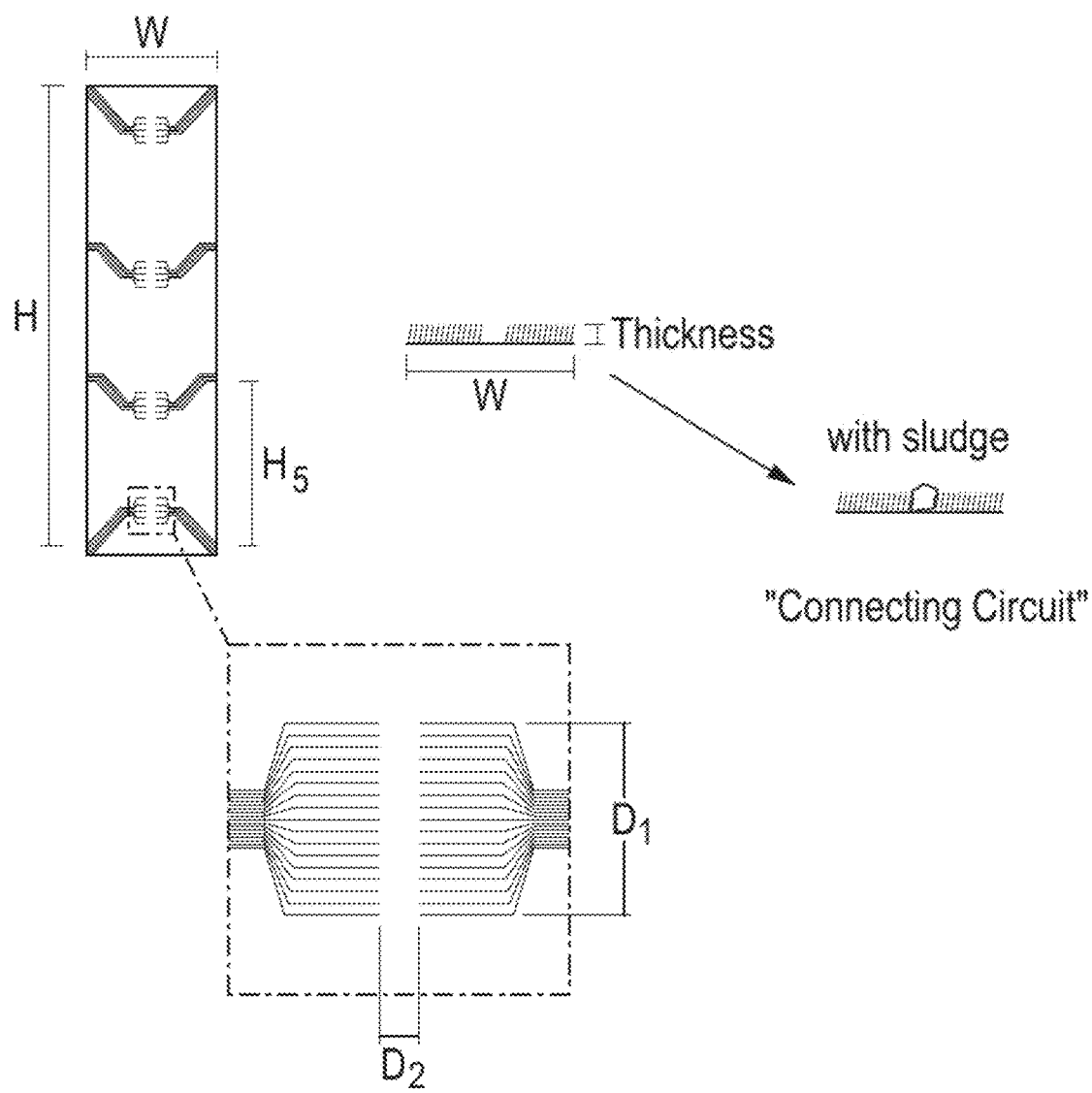
FIG. 6—Example of a dosing strip.

The vaporization device described in the above example is designed to work with dosage strips engineered specifically for efficient vaporization at the particular voltage and current supplied by the device. An example of a dosing strip is shown in FIG. 6.

The strips are composed of a non-conductive material such as ceramic or glass, and contain sludge from a whole plant liquid-gas extract at the particular resistance that is vaporized by the device. The dosage strips comprise an aluminum conductor with four (4) or more resistance sites, each of which consists of bundles of frayed aluminum which conduct the high voltage current produced by the vaporization device to the sludge to vaporize it.

The amount of sludge on each dosing strip is predetermined based on the patient and the disease and/or disorder being treated, to provide accurate and consistent dosing. The solvent-free sludge is extracted via multigas extraction and comprises the refrigerant 134A, butane, iso-butane and propane in a ratio that delivers a very complete and balanced extraction of essential oils.

The predetermined quantity of sludge is applied onto each of four or more ($R_1$-$R_4$) connections (activation sites) on the dosage strip. The dosage strips are inserted into a vaporization device and are activated by the device's microchip at any number of the sludge activation sites on each dosage strip. The amount of dose administered to the patient is selected and altered using the dosing switch on the vaporizer. The settings on the selector switch communicate with the microchip to control how many activation sites on the strip are activated.

The dosing strips and the vaporization device described herein, allow the *cannabis* active compounds to be delivered to the patient in a method that is capable of reproducible and accurate dosing for essential oil and cannabinoid medications.

DEPOSIT INFORMATION

A deposit of the *cannabis* varieties of the present invention, including the Classes of *Cannabis* Varieties, is maintained by the Biotech Institute, LLC 5655 Lindero Canyon Road, Suite 226, Westlake Village, Calif. 91362.

In addition, a tissue sample of one or more varieties of this invention, including deposit 201904001, has been deposited with an International Depositary Authority as established under the Budapest Treaty according to 37 CFR 1.803(a)(1), at the Provasoli-Guillard National Center for Marine Algae and Microbiota (NCMA), Bigelow Laboratory for Ocean Science, located at 60 Bigelow, East Boothbay, Maine 04544. The deposit of twelve cryogenic vials was made on Jul. 3, 2019.

To satisfy the enablement requirements of 35 U.S.C. 112, and to certify that the deposit of the isolated strains (i.e., *cannabis* varieties) of the present invention meets the criteria set forth in 37 CFR 1.801-1.809 and Manual of Patent Examining Procedure (MPEP) 2402-2411.05, Applicants hereby make the following statements regarding the deposited *cannabis* variety deposited as NCMA Accession No. 201904001:

If the deposit is made under the terms of the Budapest Treaty, the instant invention will be irrevocably and without restriction released to the public upon the granting of a patent.

If the deposit is made not under the terms of the Budapest Treaty, Applicant(s) provides assurance of compliance by following statements:

1. During the pendency of this application, access to the invention will be afforded to the Commissioner upon request;
2. All restrictions on availability to the public will be irrevocably removed upon granting of the patent under conditions specified in 37 CFR 1.808;
3. The deposit will be maintained in a public repository for a period of 30 years or 5 years after the last request or for the effective life of the patent, whichever is longer;
4. A test of the viability of the biological material at the time of deposit will be conducted by the public depository under 37 CFR 1.807; and
5. The deposit will be replaced if it should ever become unavailable.

Access to this deposit will be available during the pendency of this application to persons determined by the Commissioner of Patents and Trademarks to be entitled thereto under 37 C.F.R. § 1.14 and 35 U.S.C. § 122. Upon granting of any claims in this application, all restrictions on the availability to the public of the variety will be irrevocably and without restriction or condition removed by affording access to a deposit of the tissue sample of the same variety with the depository.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A regenerable cell from *cannabis* plant designated CBD5, said cell having been deposited under Bigelow NCMA Accession No. 201904001.

2. A *cannabis* plant, or plant part, tissue, or cell thereof produced by regenerating the cell of claim 1, wherein said *cannabis* plant, or plant part, tissue, or cell thereof comprises a cannabinoid profile and a terpene profile as set forth in Tables 19.1 and 19.2, respectively.

3. The *cannabis* plant part of claim 2, wherein said plant part is selected from the group consisting of: stems, trichomes, leaves, and flower buds.

4. A *cannabis* clone regenerated from the *cannabis* plant of claim 2.

5. An edible product comprising the *cannabis* plant, or plant part, tissue, or cell thereof of claim 2.

6. A method of producing an F1 *cannabis* seed, said method comprising crossing the plant of claim 2 with a different *cannabis* plant, and harvesting the resultant F1 *cannabis* seed.

7. The F1 hybrid *cannabis* seed produced by the method of claim 6.

8. An F1 hybrid *cannabis* plant produced by growing the F1 hybrid *cannabis* seed of claim 7.

9. A *cannabis* clone regenerated from the F1 hybrid *cannabis* plant of claim 8.

10. An edible product comprising *cannabis* tissue from the F1 hybrid *cannabis* plant of claim 8.

* * * * *